(12) United States Patent
Phillips

(10) Patent No.: US 11,013,621 B2
(45) Date of Patent: May 25, 2021

(54) PROSTHETIC ENERGY STORING AND RELEASING APPARATUS

(71) Applicant: Van L Phillips, Albion, CA (US)

(72) Inventor: Van L Phillips, Albion, CA (US)

( * ) Notice: Subject to any disclaimer, the term of this patent is extended or adjusted under 35 U.S.C. 154(b) by 0 days.

(21) Appl. No.: 14/348,534

(22) PCT Filed: Oct. 1, 2012

(86) PCT No.: PCT/US2012/058365
§ 371 (c)(1),
(2) Date: Mar. 28, 2014

(87) PCT Pub. No.: WO2013/049852
PCT Pub. Date: Apr. 4, 2013

(65) Prior Publication Data
US 2014/0243998 A1    Aug. 28, 2014

Related U.S. Application Data

(60) Provisional application No. 61/541,041, filed on Sep. 29, 2011.

(51) Int. Cl.
*A61F 2/66* (2006.01)
*A61F 2/60* (2006.01)
*A61F 2/50* (2006.01)

(52) U.S. Cl.
CPC .................. *A61F 2/60* (2013.01); *A61F 2/66* (2013.01); *A61F 2002/5003* (2013.01); *A61F 2002/5007* (2013.01); *A61F 2002/5009* (2013.01); *A61F 2002/5056* (2013.01); *A61F 2002/607* (2013.01); *A61F 2002/6664* (2013.01); *A61F 2002/6671* (2013.01); *A61F 2002/6685* (2013.01)

(58) Field of Classification Search
CPC .. A61F 2/60; A61F 2/66; A61F 2/6607; A61F 2002/607; A61F 2/64; A61F 2/80; A61F 2/644; A61F 2/642
See application file for complete search history.

(56) References Cited

U.S. PATENT DOCUMENTS 5,387,246 A    2/1995  Phillips
5,593,456 A *  1/1997  Merlette ................... A61F 2/60
                                                              623/32
5,766,265 A    6/1998  Phillips
(Continued)

FOREIGN PATENT DOCUMENTS

WO    WO2011/066354    6/2011

*Primary Examiner* — Marcia L Watkins
(74) *Attorney, Agent, or Firm* — J. Steven Svoboda

(57) ABSTRACT

A prosthetic lower leg uses one or more generally C-shaped spring elements between the patient's socket and a footplate assembly. The respective connections between (a) those one or more elements and (b) that socket and that footplate can be configured to provide a lightweight and economic prosthesis that effectively mimics the feel and performance of a normal human foot. The prosthetic spring element is generally C-shaped, and can have a substantially constant thickness along its length, lending itself to being fabricated by automated processes such as filament winding. One or more of the generally C-shaped spring elements can be incorporated into other prostheses and/or other devices.

18 Claims, 98 Drawing Sheets

(56) References Cited

U.S. PATENT DOCUMENTS

| | | | |
|---|---|---|---|
| 5,976,191 A | 11/1999 | Phillips | |
| 6,099,572 A | 8/2000 | Mosler et al. | |
| 6,706,075 B1* | 3/2004 | Laghi | A61F 2/66 623/52 |
| 7,172,630 B2* | 2/2007 | Christensen | A61F 2/66 623/53 |
| 8,535,390 B1* | 9/2013 | Lecomte | A61F 2/66 623/53 |
| 8,771,372 B1* | 7/2014 | Rubie | A61F 2/66 623/52 |
| 2002/0143406 A1 | 10/2002 | Townsend et al. | |
| 2003/0045944 A1* | 3/2003 | Mosler | A61F 2/66 623/52 |
| 2003/0120353 A1 | 6/2003 | Christensen | |
| 2004/0068327 A1* | 4/2004 | Christensen | A61F 2/66 623/52 |
| 2005/0038524 A1* | 2/2005 | Jonsson | A61F 2/66 623/55 |
| 2005/0187640 A1* | 8/2005 | Christensen | A61F 2/66 623/52 |
| 2006/0161267 A1* | 7/2006 | Clausen | A61F 2/5046 623/55 |
| 2007/0198017 A1* | 8/2007 | Tschakaloff | A61B 17/0401 606/326 |
| 2009/0157197 A1* | 6/2009 | Bonacini | A61F 2/76 623/55 |
| 2009/0265019 A1 | 10/2009 | Christensen | |
| 2010/0023135 A1* | 1/2010 | Rubie | A61F 2/66 623/55 |
| 2011/0071650 A1* | 3/2011 | Townsend | A61F 2/60 623/55 |
| 2013/0030549 A1* | 1/2013 | Zahedi | A61F 2/60 623/39 |
| 2013/0268092 A1* | 10/2013 | Karlsson | A61F 2/80 623/43 |

\* cited by examiner

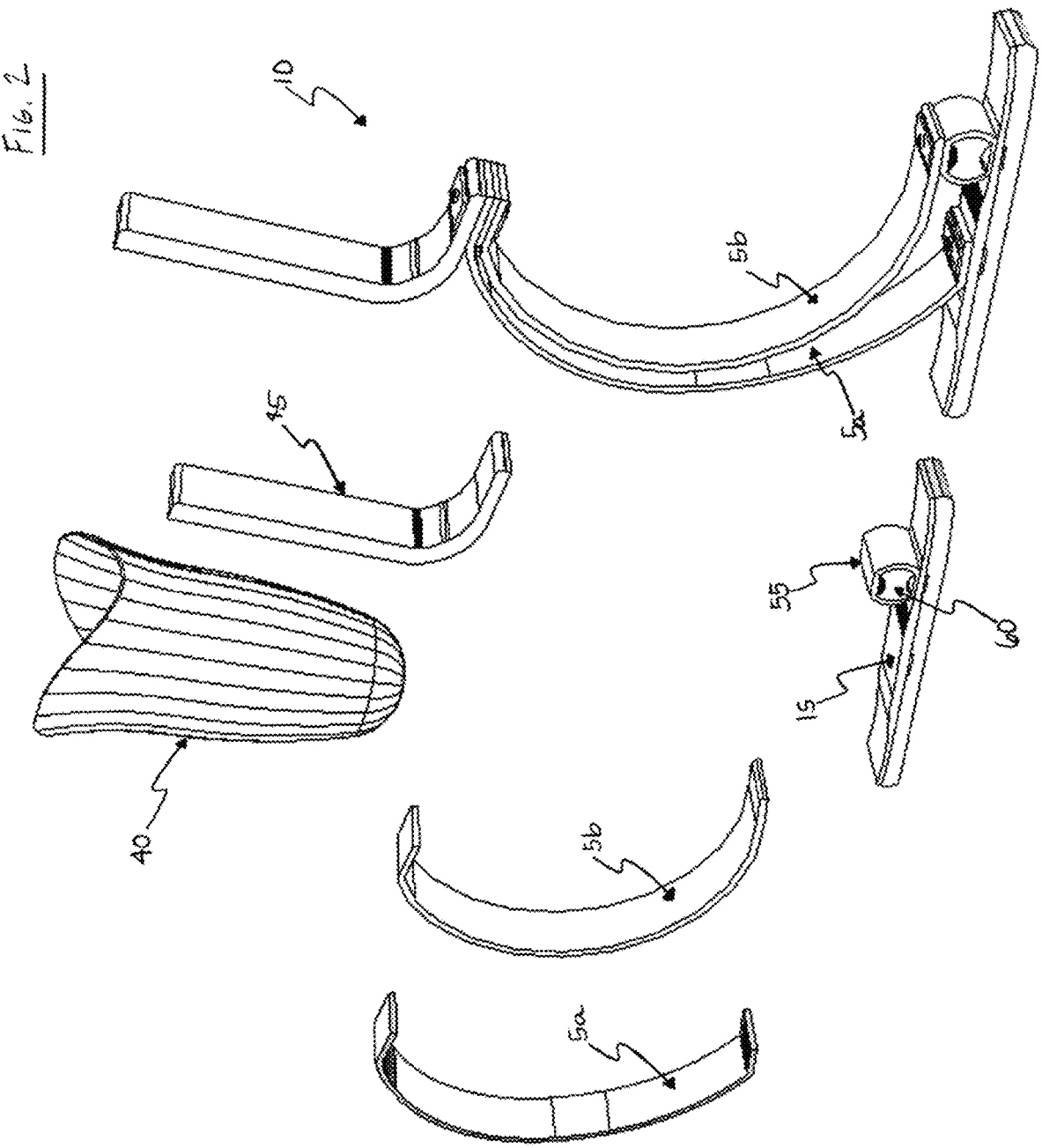

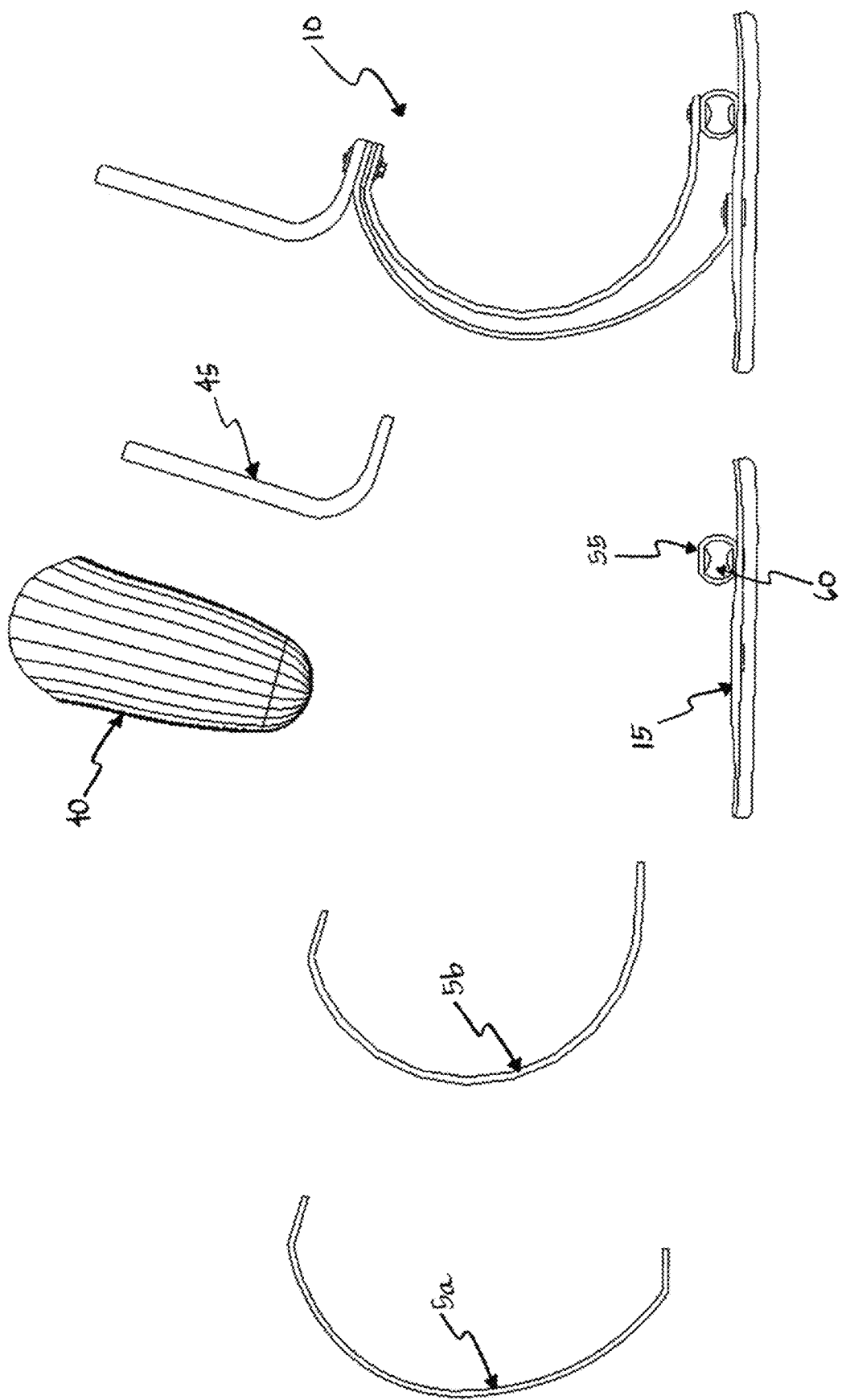

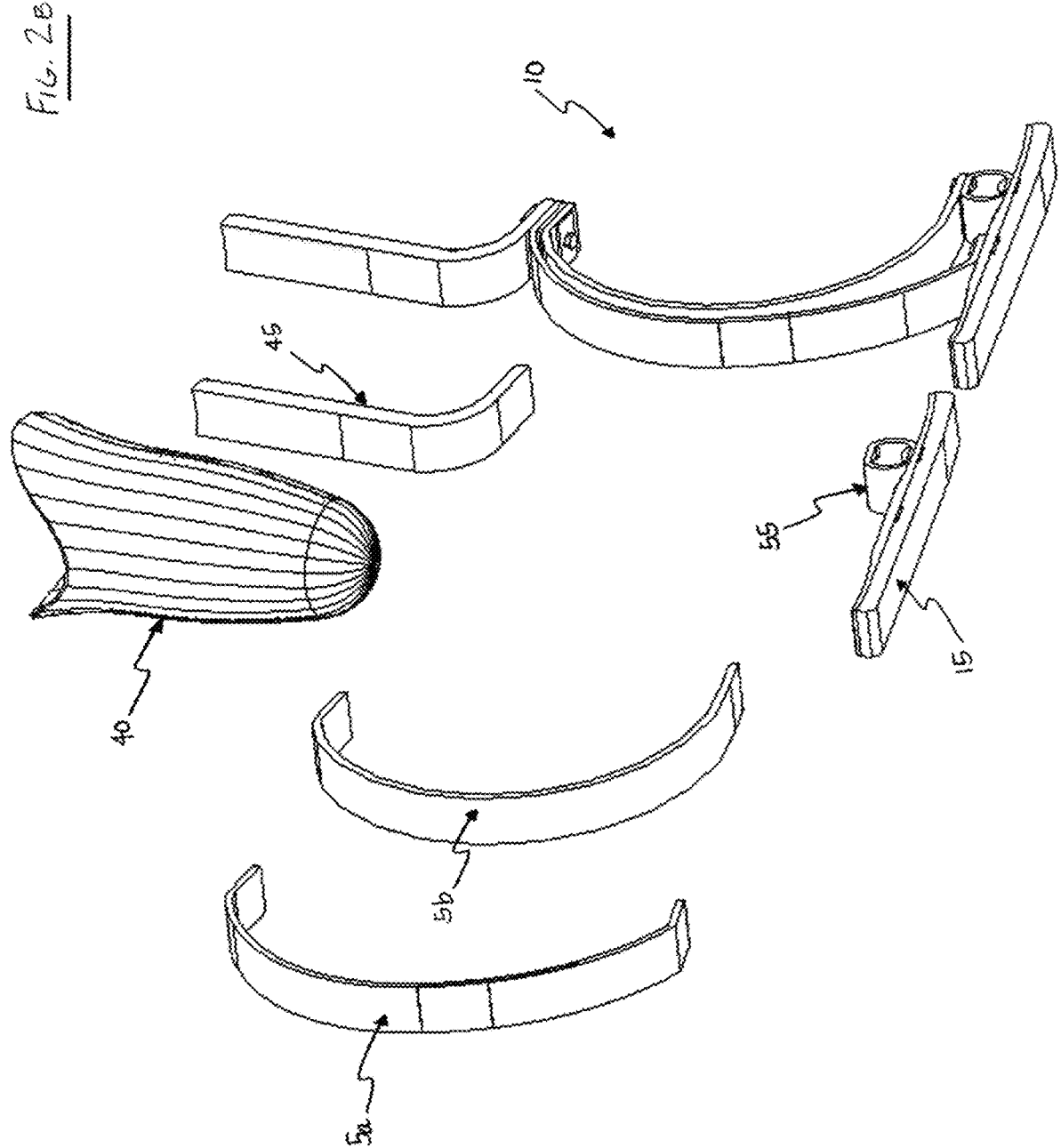

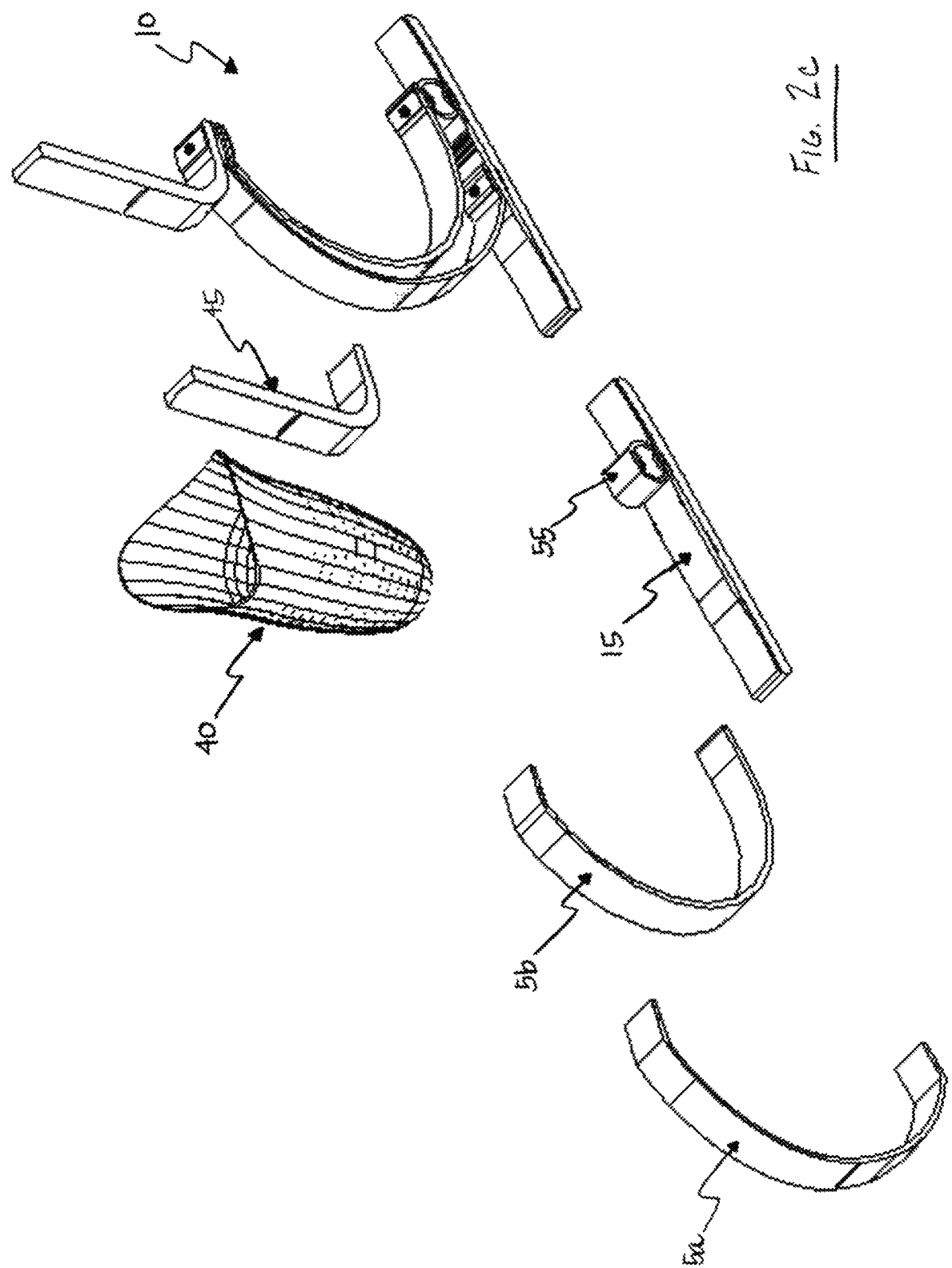

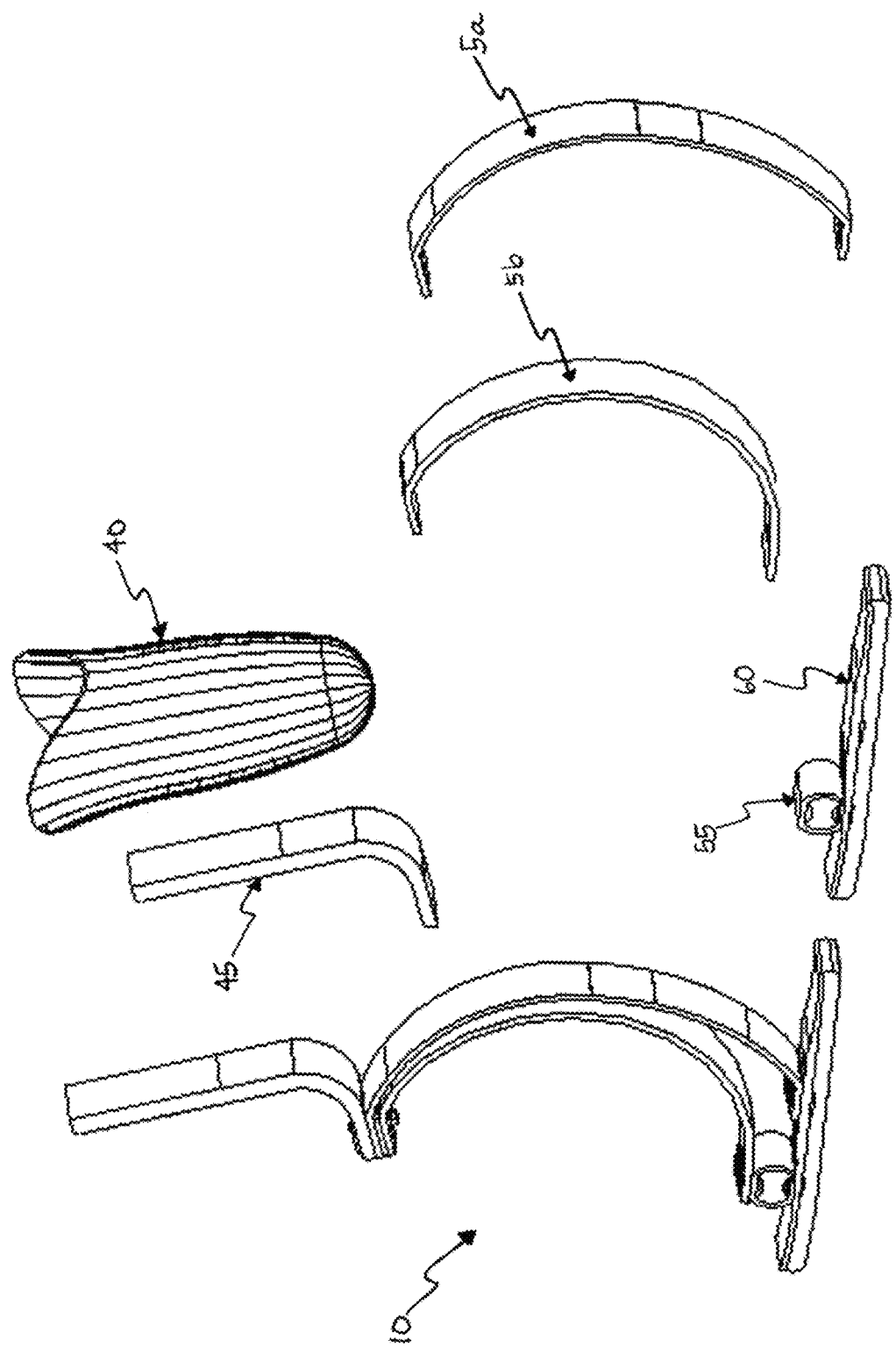

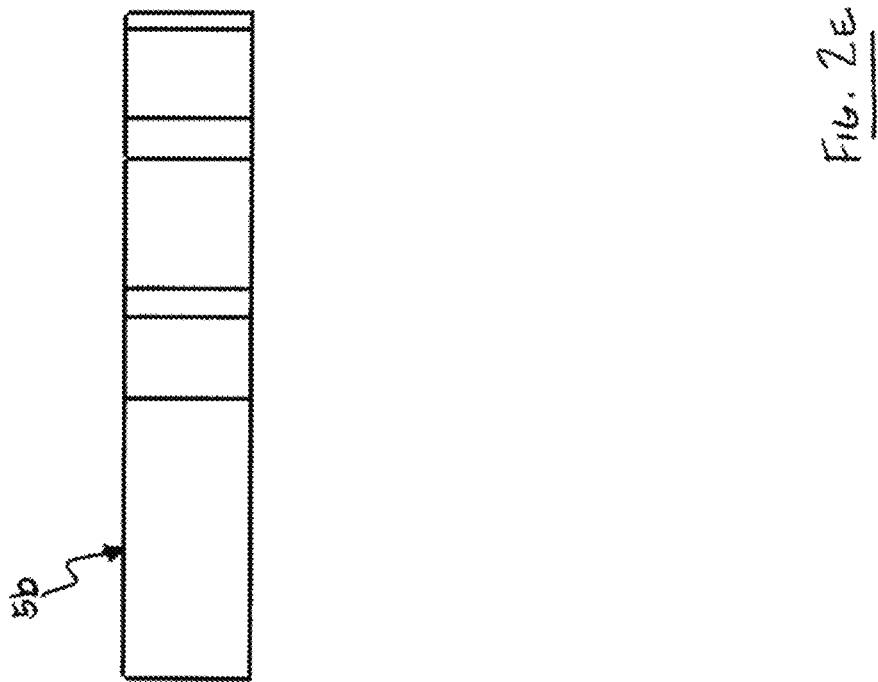
FIG. 2e
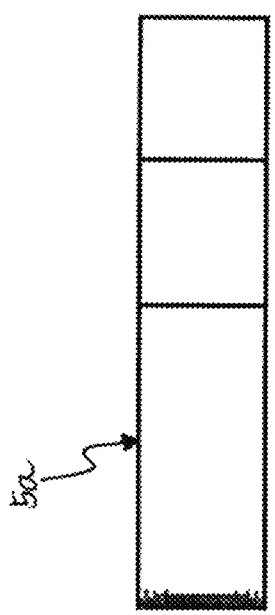

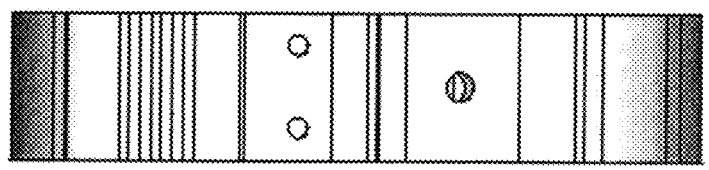
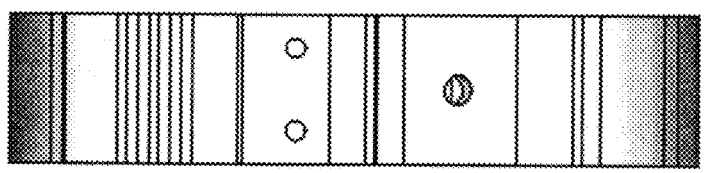
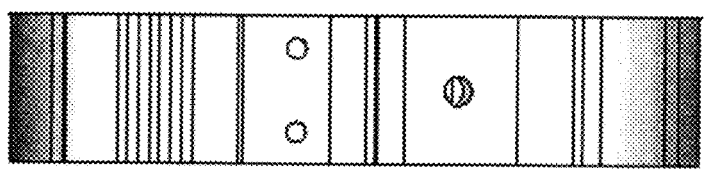
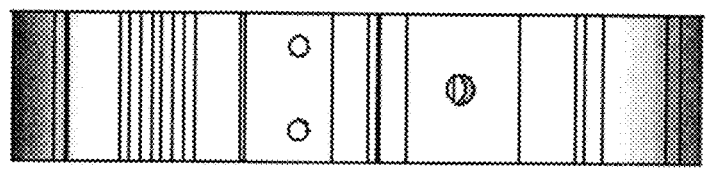
FIG 6F

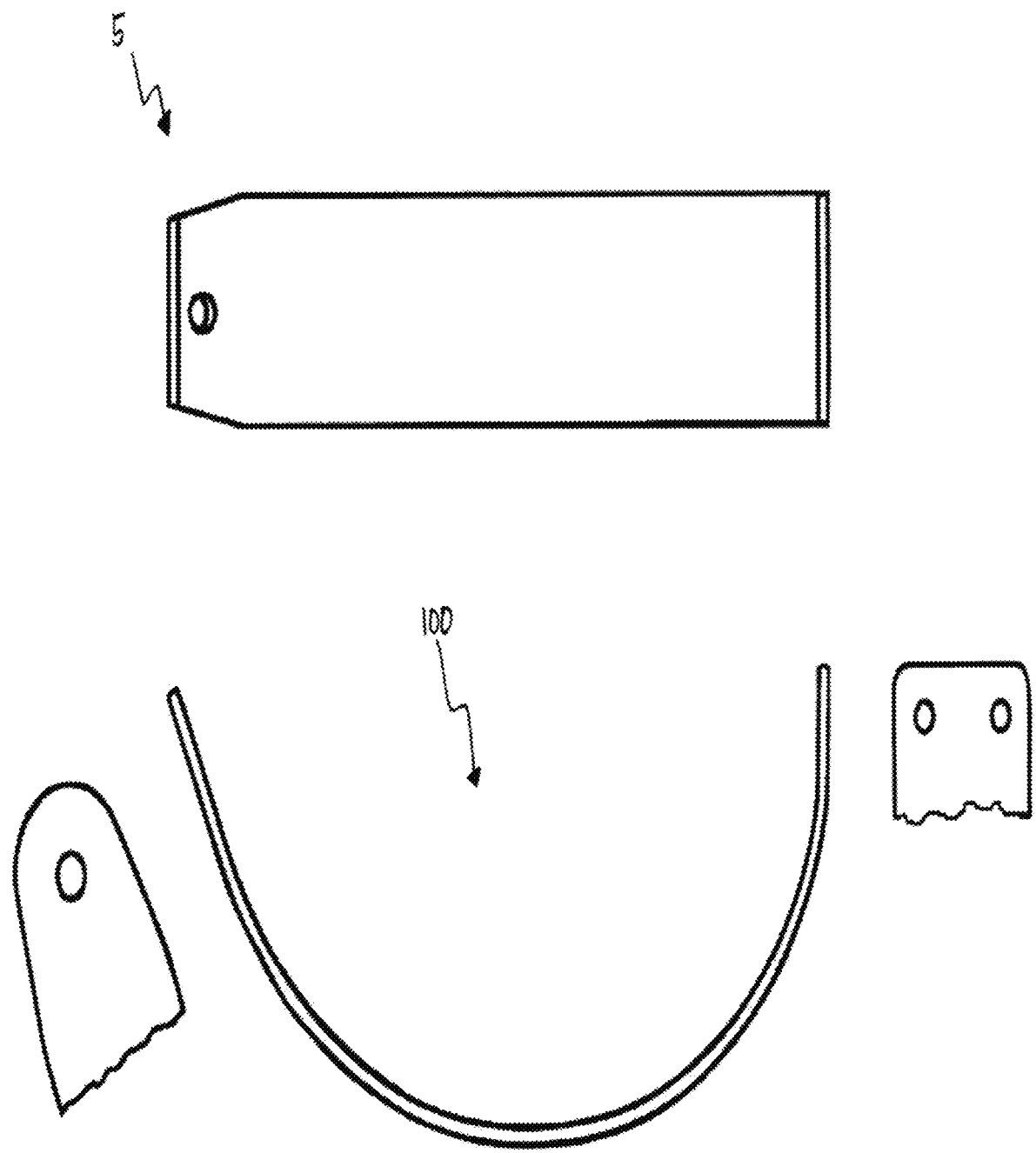

PROSTHETIC ENERGY STORING AND RELEASING APPARATUS

This application is based on and claims the benefits of the filing date of U.S. Provisional Patent Application No. 61/541,041 (filed Sep. 29, 2011).

The present invention is described here with reference to the accompanying Figures, which serve as illustrations of some of the many embodiments in which the invention may be practiced. Generally in those Figures and references (but subject to the context and other factors, including for example the understanding of persons of ordinary skill in the arts relevant to the inventions), similar reference numerals refer to similar or identical elements throughout this description.

Those Figures and references, and the other terminology used in these descriptions, are not intended to be interpreted in any limited or restrictive manner, simply because it is being utilized in conjunction with a detailed description of certain embodiments of the invention. Furthermore, various embodiments of the invention (whether or not specifically described herein) may include one or more novel features, no single one of which (a) is necessarily solely responsible for one or more desirable attributes of the invention or (b) is essential to practicing the inventions described.

DESCRIPTION OF DRAWINGS

FIGS. 2, 2a, 2b, 2c, and 2d are exploded perspective views of an overall prosthetic assembly in accordance with the present invention.

FIG. 2e is a top view of two elongated curved energy-storing/releasing members in accordance with the present invention.

FIG. 6b is a perspective end view of the stack of energy storing and releasing elements shown in FIG. 6a.

FIG. 6c is a perspective elevation view of the stack of energy storing and releasing elements shown in FIG. 6a.

FIGS. 6d and 6e are perspective views of multiple energy storing and releasing elements fabricated by a filament winding process.

FIG. 6f is a top view of the multiple energy storing and releasing elements shown in FIGS. 6d and 6e.

FIG. 6g is an isometric view of a single energy storing and releasing element fabricated by a filament winding process.

FIG. 6l is a bottom view of the single energy storing and releasing element shown in FIG. 6g.

FIG. 7 shows a top and side view of a preferred C-spring element in accordance with the present invention, and a top view of the ends of the C-spring element with holes for connecting the C-spring element at a connection point(s).

In FIG. 26, the sockets at the top of the two drawings have been generally aligned, allowing a comparison of the lower portions of the two prostheses. Among other things, this illustrates how slight modifications to curvature, orientation, and other factors can be used to produce embodiments of the invention that can be used for different amputees and for different purposes and activities.

DETAILED DESCRIPTION OF EMBODIMENTS

Figure 1:
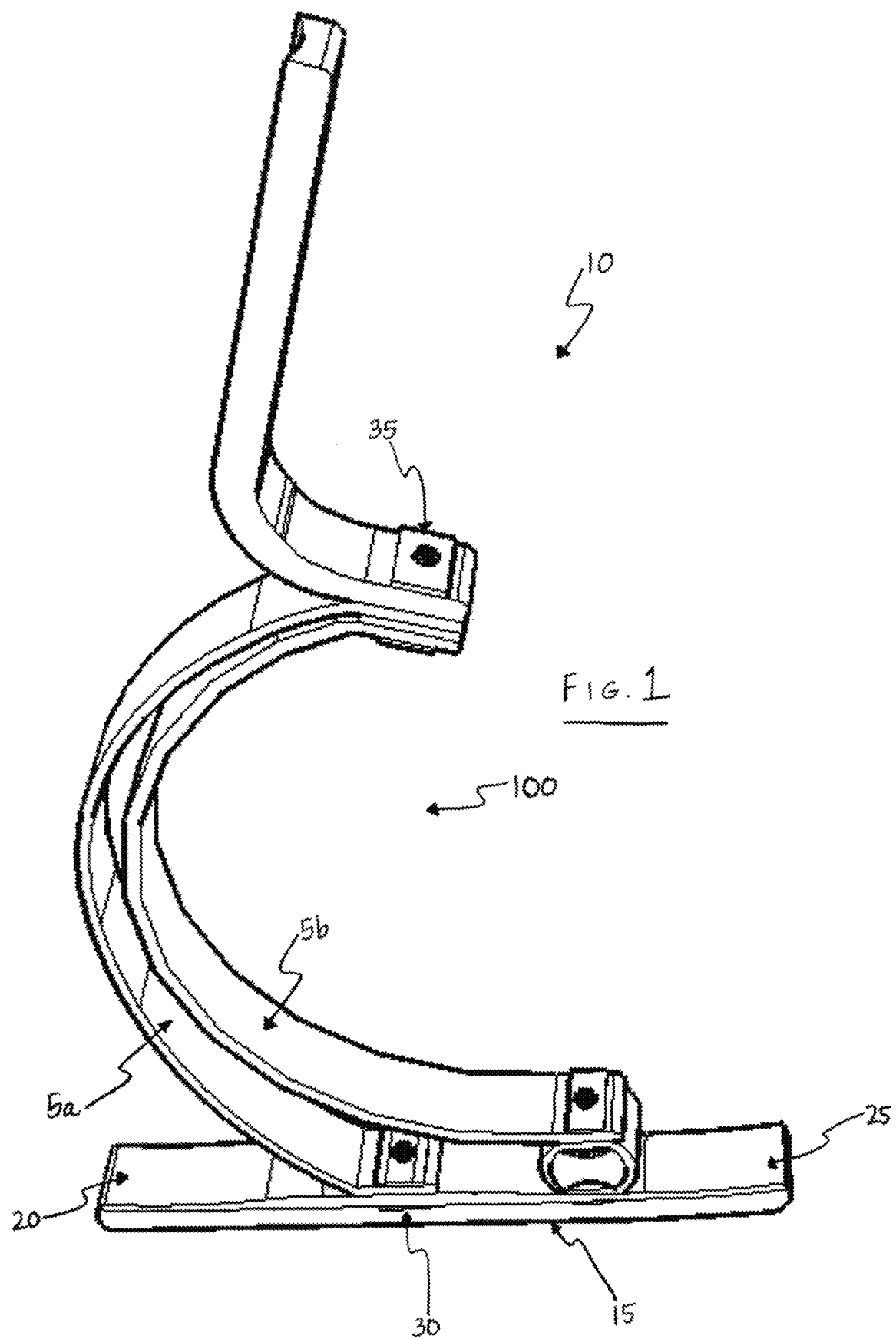
FIGS. 1, 1a and 1b are perspective views of a preferred embodiment of the present invention having two elongated curved energy-storing/releasing members.
Figure 1A:
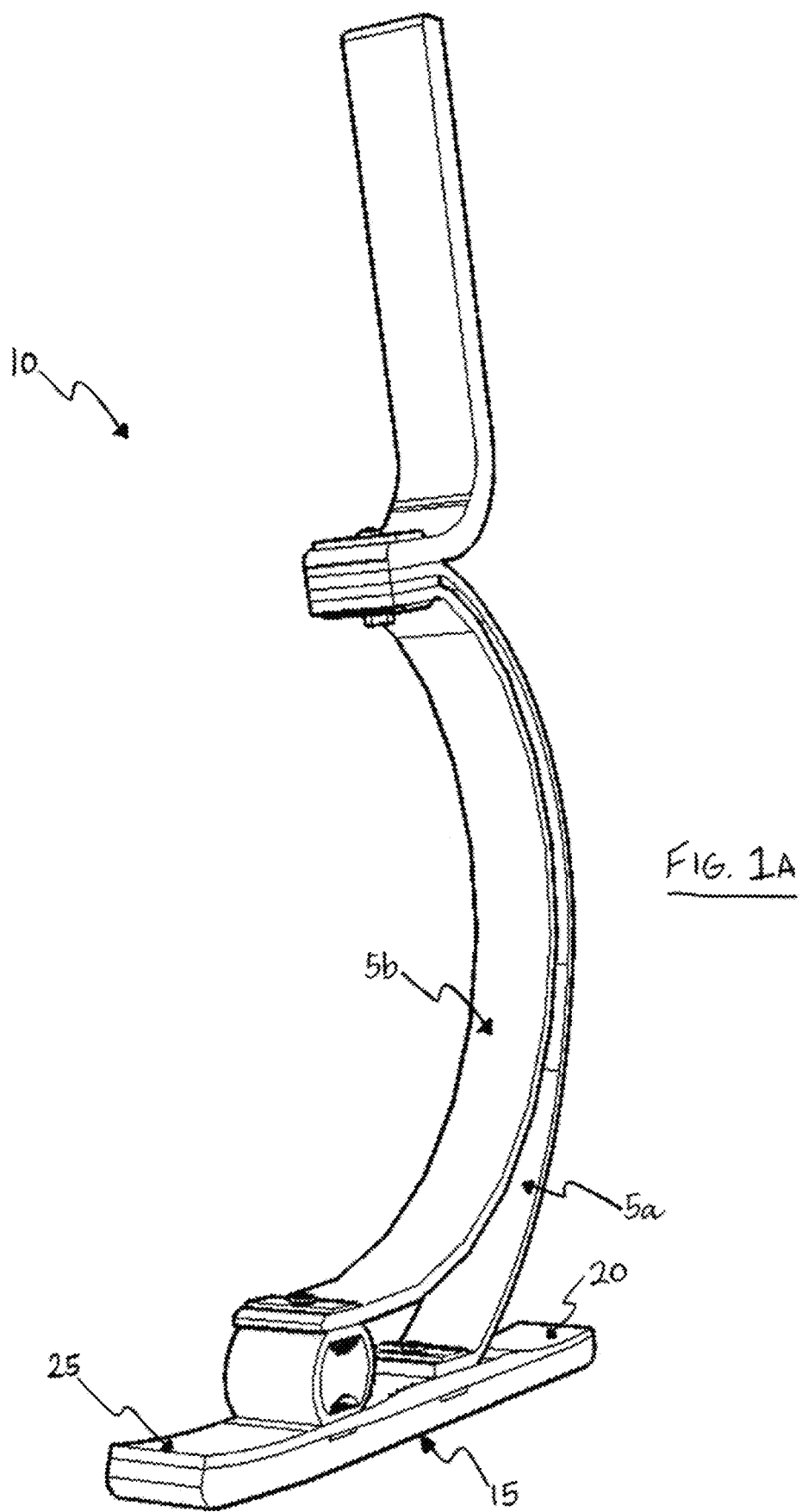
Figure 1B:
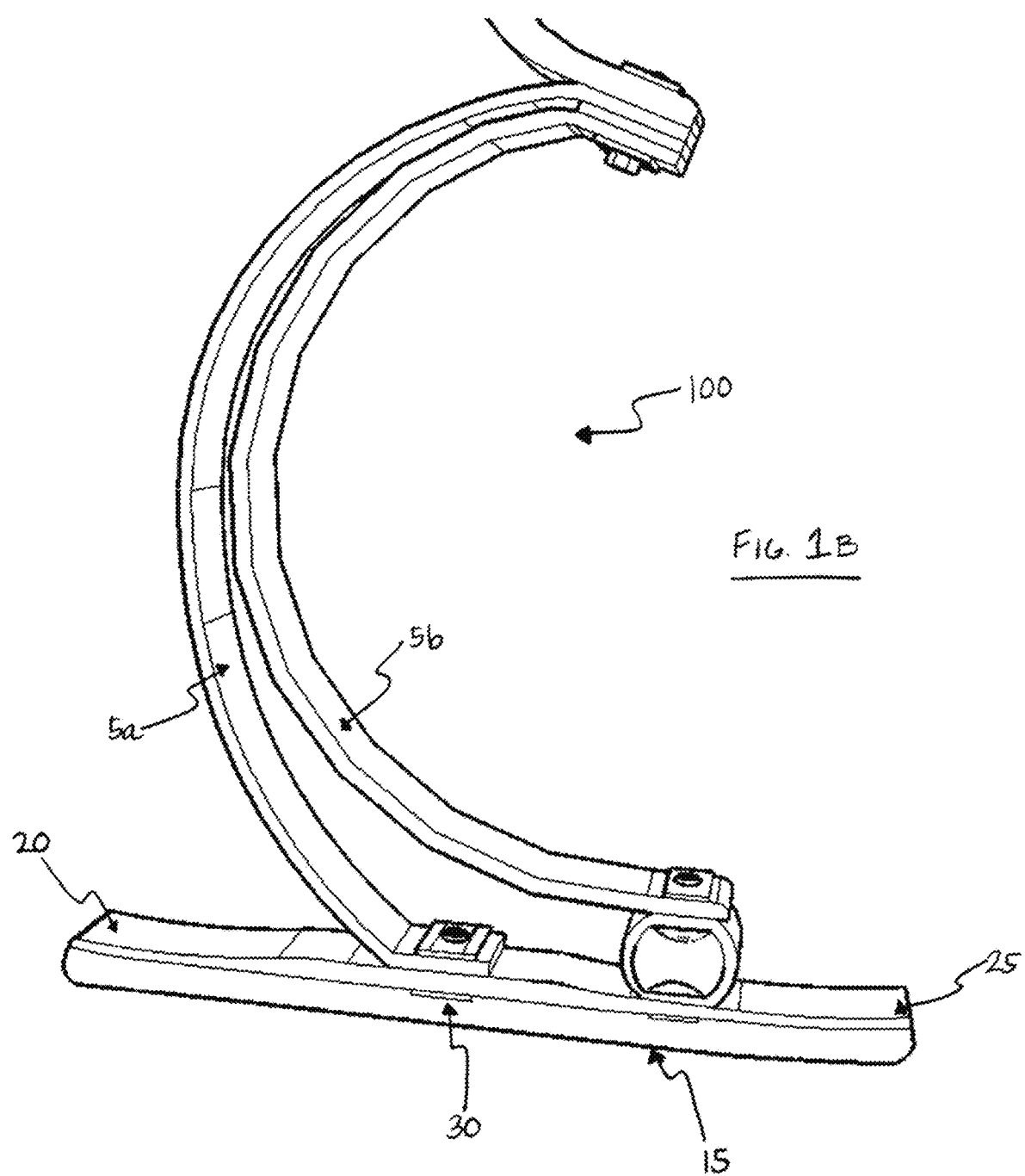
Figure 1C:
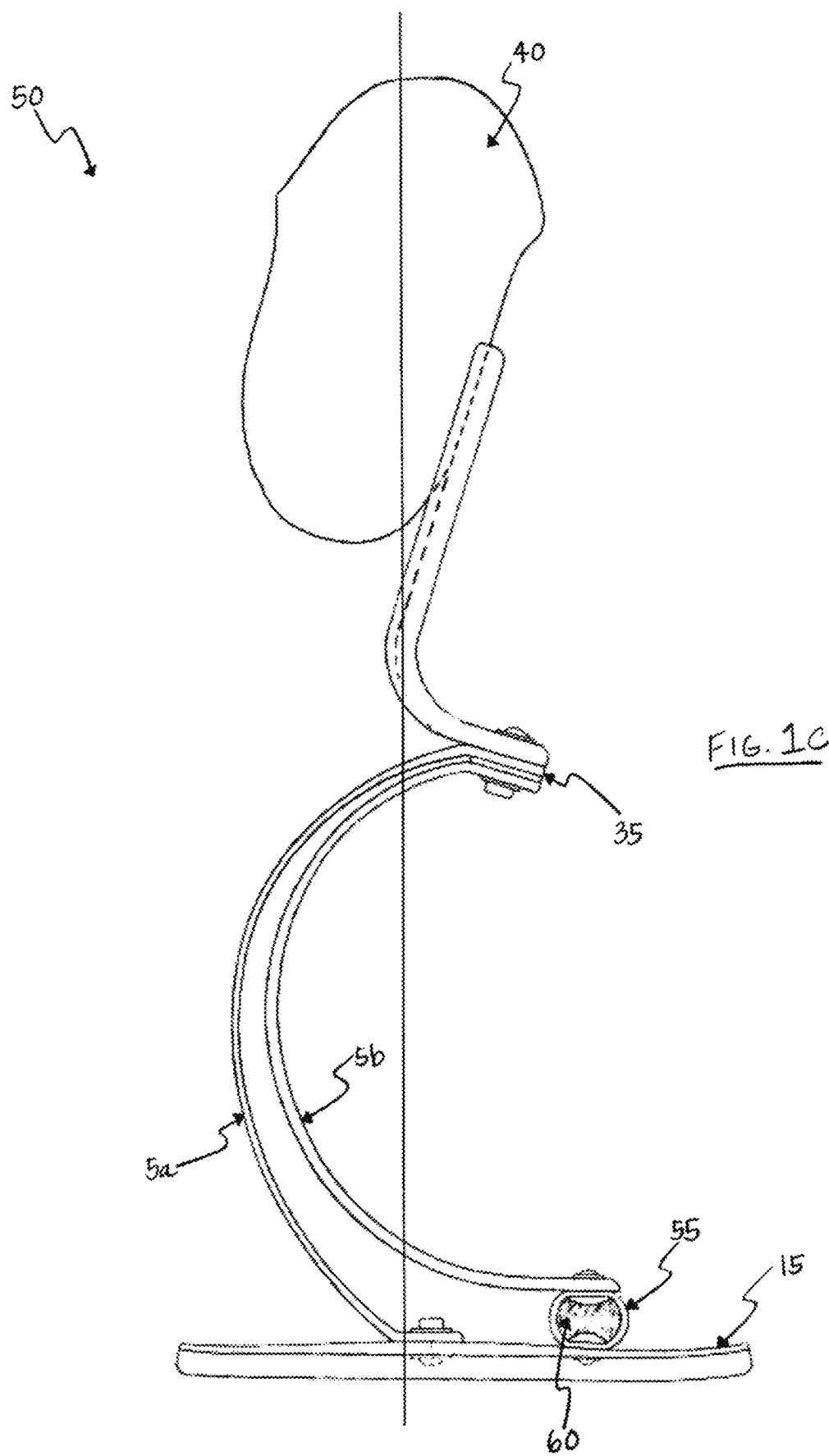
FIG. 1c is an elevation view of an overall prosthetic assembly in accordance with the present invention, including a prosthetic device having two elongated curved energy-storing/releasing members operably connected to a prosthetic socket, and having a compressible element.
Figure 2F:
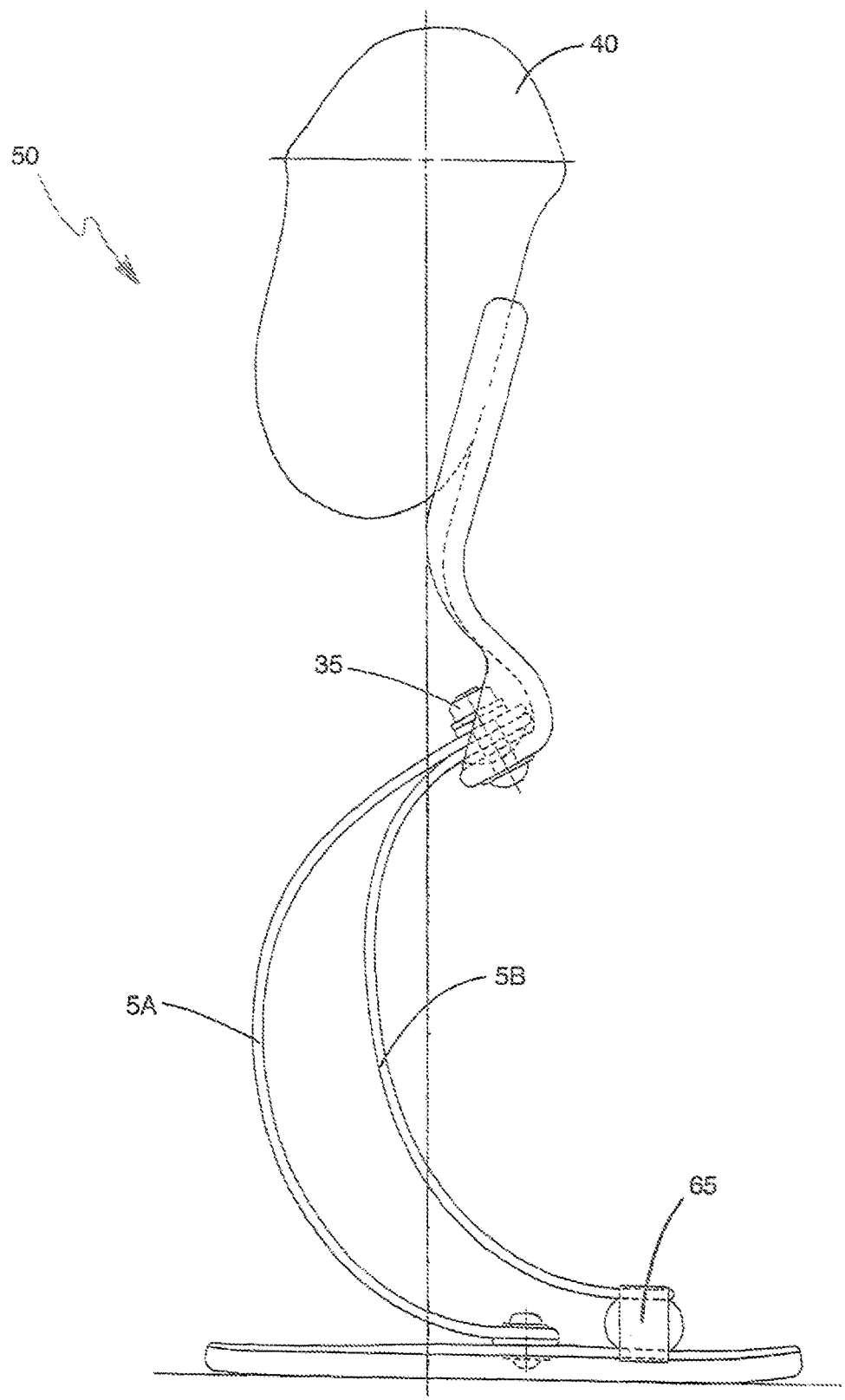
FIGS. 2f and 2g are elevation views of an overall prosthetic assembly in accordance with the present invention, having a connector element in a forward position (FIG. 2f) and a preferred position (FIG. 2g).
Figure 2G:
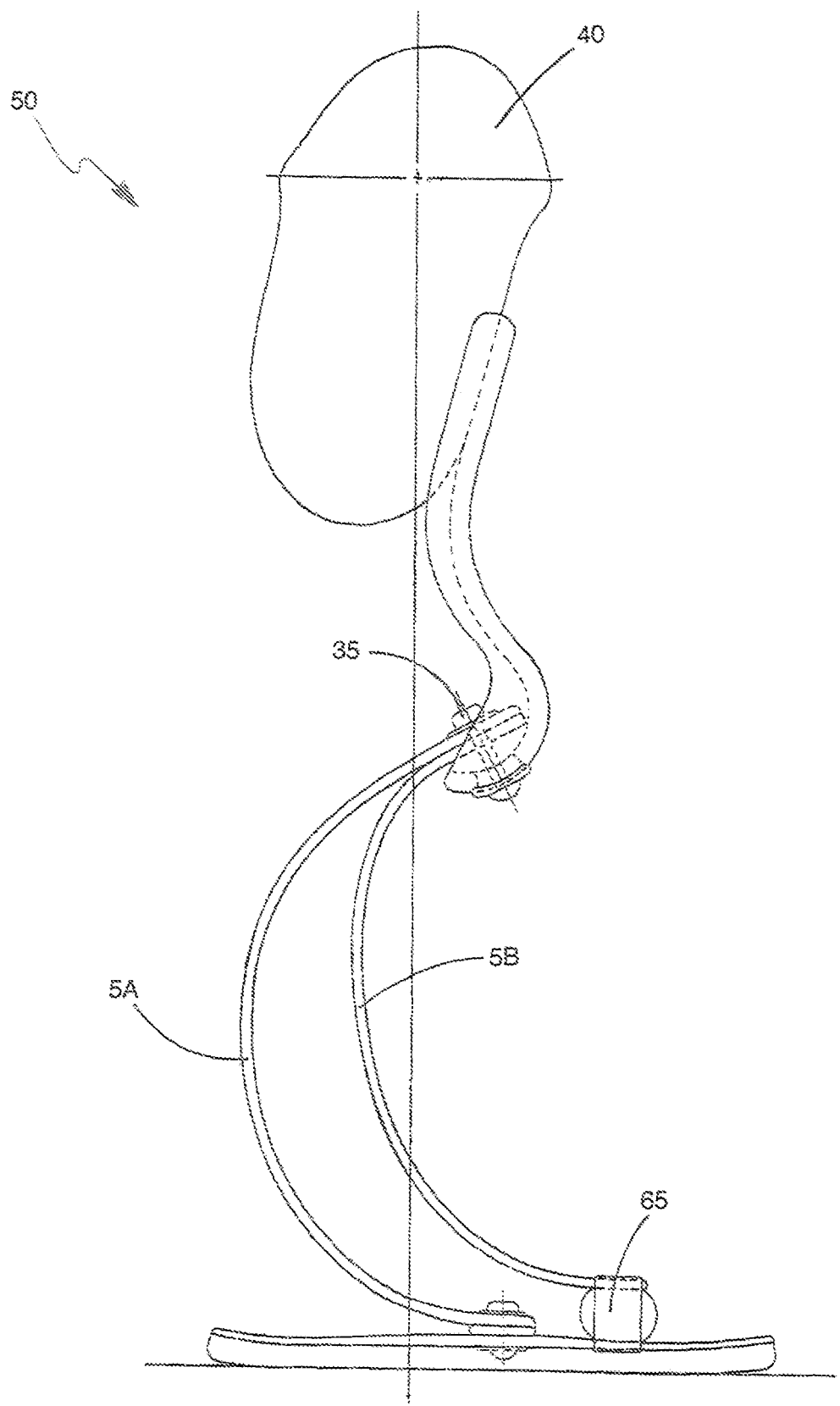

The present inventions preferably include and/or constitute one or more elongated energy storing and releasing elements, usable in lower leg prostheses and other devices and assemblies and methods. In addition, the inventions preferably include various methods of fabricating, assembling, fitting, and otherwise using various prosthetic devices, including devices having single and/or multiple elongated energy storing and releasing elements.

The particular materials, dimensions, and fabrication methods for practicing the invention can be selected from a wide range of possibilities, depending on a number of factors (including those discussed in many of my previous patents, which are incorporated herein by reference). By way of example, these energy storing and releasing elements can be formed by any suitable method(s) and from any suitable material(s), including from resin-impregnated fiber, and by filament winding processes, among others.

Preferably, the invention is practiced in a modular manner, so that the various components (e.g., footplates, connectors, extensions, bolts, C-Shaped Spring elements, and others) are effectively interchangeable with other such components, and may sometimes even be interchangeable between various Single Spring, Two-Spring, and other embodiments of the invention. These components may even be used in retrofitting existing devices. This enables easy customization, maintenance, and repair of an overall prosthetic assembly 50. Depending on the patient and the application, certain components may need to be shaped slightly differently for cosmetic or other reasons, but their functionality preferably is at least substantially unaffected by such changes.

Although the energy storing/releasing member(s) 5 and other parts of the assembly preferably are modular, they can be fabricated in other combinations and sub-combinations, and can be relatively permanently assembled or otherwise utilized, all without departing from the spirit and scope of the invention.

On another aesthetic point, certain of the embodiments below are described as preferably having the connector/attachment/pivot points moved relatively forward toward the toe portion of the prosthesis. Persons of ordinary skill in the art will understand that this may make it more difficult to fit a conventional cosmetic cover and/or a shoe over the prosthesis. However, the relatively forward pivot/connection elements preferably actually can provide some aesthetic benefit. Among other things, those forward elements preferably hold a normal trouser or pant leg out to a "normal" draping position, forward with respect to the wearer's ankle area (or away from the wearer's heel). Without those further-forward features, the pant leg can be pushed abnormally far back by wind resistance or similar force.

Preferred Use in a Lower-Leg Prosthesis:

When incorporated into a lower leg prosthesis, the one or more energy-storing/releasing members of the invention and other aspects of the invention can provide an excellent experience for wearers, including a very smooth and natural stride during walking, running, and similar activities. The Figures and description here focus on examples of prostheses with one and with two such members, but the present inventions may be practiced in other combinations of elements (and other embodiments of prosthetic devices having one- and two-member, or even more such members).

In this description and the related Figures, the cadence of walking and similar activities is described as including the positions of heel strike, then mid-stance, and finally toe-off. Persons of ordinary skill in the art will understand that these are not intended as precise and limiting concepts but instead as a useful framework within which to describe the invention. Among other things, persons of ordinary skill in the art will understand that the inventions will find utility in a broad range of activities other than walking.

Double C Embodiments (Springs 1 and 2)

A preferred embodiment of the invention is illustrated in FIGS. 1, 1a, 1b, and 1c as having two of the elongated curved energy-storing/releasing members 5a, 5b of the invention 10. As used in this description of those drawings, "Spring 1" refers to the radially outermost member 5a (located toward the rear of the prosthesis, in the heel area 20 in the drawings), and "Spring 2" refers to the forward or "radially inner" spring 5b. In certain embodiments, Spring 1 5a is relatively soft to allow ready vertical compression, and Spring 2 5b is relatively stiff, so that it does not allow such ready vertical compression. Persons of ordinary skill in the art will understand that these differences in stiffness and performance characteristics can be achieved by any suitable means, including by varying the number of plies or other material impregnated into each of those respective Springs 1 and 2, and that because of the nature of certain embodiments of the invention (such as for those in which the C-shaped springs are made using resin-impregnated fiber), the springs may be very similar visually (having substantially similar thicknesses, for example) but yet have noticeably different loading/spring/performance characteristics.

Preferably, both Spring 1 and Spring 2 are operably connected to the patient's socket 40 at or near their upper ends. This is discussed further below in connection with a preferred connector element 35, and is illustrated in the drawings as being accomplished by a single bolt placed through holes in both Spring 1 and Spring 2 and then through a ball/sphere support structure that rotatably seats in a confronting socket (not the "socket" into which the patient places his/her stump) on that connector, and through a corresponding hole in that connector. To allow a wide range of angles and orientations at that connection point, various washer elements are provided and at least the hole through the connector element opens to an increasingly larger radius in the general direction of from the patient toward the prosthetic toe portion 25. Persons of ordinary skill in the art will understand that (a) this allows a convenient adjustment and alignment of the prosthetic assembly with respect to the patient (as further discussed below) and (b) many other alternative attachment structures can be used without departing from the scope of the invention. By way of example, each of Spring 1 and Spring 2 can be separately connected to the patient's socket, rather than being joined in a common connection point.

As shown in the drawings, the lower end of Spring 1 preferably is attached to a middle portion 30 of the footplate 15, and in a resting position, the lower end of Spring 2 preferably is spaced above the footplate and relatively forward (toward the toe portion) from that Spring 1 connection point.

As indicated above, preferably both Springs 1 and 2 are fabricated and configured to be capable of energy storage and release as the patient wearing the prosthesis undertakes various activities (such as walking) Preferably, the spring/bending properties of both Springs 1 and 2 urge them to their resting "C" position 100 from either an expanded condition (a more open C) or a compressed condition (a more closed C). Any twisting or other deformation of the elements such as Springs 1 and 2 likewise preferably stores that twisting/other energy and urges the spring element to return to its untwisted "resting" position.

Preferably, Springs 1 and 2 are oriented so that their respective C-shaped portions open toward the front of the wearer. This preferably allows the prosthetic assembly to be enclosed in a cosmetic cover and otherwise fit within the profile of a natural foot and into conventional shoes. In some of the many alternative embodiments of the invention, however, the Springs (especially the interior Spring 2) can be rotated about a generally vertical axis through their upper and lower connection locations, at 180 degrees (so that it opens toward the wearer's heel) or at some other angle, and still provide some or all of the benefits described herein. However, such alternative angles presumably would make it difficult to use a conventional cosmoses over the prosthesis.

Heel Strike

Within the walking cadence terminology mentioned above, "heel strike" refers to that portion of a normal forward stride that includes the initial contact of the heel with the ground or other surface. As discussed below, the continuation of the stride moves the prosthetic foot from heel strike toward the mid-stance position.

In many embodiments, a prosthetic footplate 15 is operably affixed to the lower end(s) of the C-shaped spring members. Although the invention preferably can be practiced with a wide range of sizes and shapes of the footplate (and variations in other features, such as whether it is a single piece or formed from separate heel and toe elements, or otherwise), a convenient and conventional size and shape for such footplates is generally flat, in the shape of the sole of a natural foot, including having a toe portion and a heel portion. Preferably, all or most of the prosthetic footplate is also fabricated as a deformable energy storing/returning element, via filament winding or hand layup or other process.

Just prior to heel strike, as the wearer is stepping forward, the footplate preferably is angled upwardly (approximating the position of a natural foot), with the toe portion at least slightly higher than the heel portion. This means that, at heel strike, the footplate's heel portion preferably is the first part of the footplate to contact the ground or other surface (thus the term "heel strike").

As the patient moves forward through the heel strike position and portion of the stride, the heel portion may deform slightly (storing energy that will be released in later stages of the stride) and an increasing area of the preferred footplate member heel portion preferably contacts the ground or other surface. At least in part, the heel portion deformation or bending is caused by the wearer starting to transfer his or her weight onto that prosthetic heel/foot.

In addition to and/or independently of the heel deformation, that transfer of the patient's generally vertical weight loading preferably immediately engages and begins compressing Spring 1 (again, storing energy that will be released in later stages of the stride). Spring 1 preferably is sufficiently "soft" or energy-compliant that Spring 1 immediately, gradually, and smoothly begins to compress and store that energy, for subsequent spring-back action. As the wearer continues into the step and puts more weight onto that leg/foot, Spring 1 continues to compress and thereby store increasing amounts of energy. In many preferred embodiments, the compression of Spring 1 is on the order of approximately one inch of vertical compression for a 3G vertical load.

As indicated above, the heel strike condition and portion of the stride may bend the heel portion of the footplate relatively upward toward the C-shaped portion(s). The existence of such deformation and its amount and other characteristics can depend on a number of factors (for example, the nature of the loading on the prosthesis, the spring characteristics of Spring 1, the spring characteristics of the footplate, and others). Because the toe portion of the footplate is not yet contacting the ground during heel strike, the heel strike loading preferably also tends to pivot the footplate around the connection point between Spring 1 and the footplate, causing the toe portion of the footplate to plantar-flex (the toe portion is pushed toward the ground). If unchecked, the toe portion might even immediately (and undesirably) "slap" down onto the ground/surface.

Because Spring 1 preferably is relatively so "soft" (to provide the desired vertical compliance), Spring 1 provides relatively little, if any, resistance to that planter-flexion. Instead, a preferred embodiment of the device relies on the inner C (Spring 2) to help limit that plantar-flexion. Preferably, the inner C (Spring 2) is relatively stiffer than Spring 1, and is operably connected at its upper end to the upper end of Spring 1, and at its lower end to the toe portion of the footplate (via a strap 65 or other means, as further discussed herein).

In a preferred configuration, the plantar-flexion of the footplate's toe portion also pulls the strap member 65 toward the ground, and the strap in turn imposes a load on Spring 2. This load urges Spring 2 to "open" into a larger C shape, and depending on the loading and the spring characteristics of Spring 2 and other factors, permits some desirable amount and rate of plantar flexion. As it opens/spreads, Spring 2 preferably stores that energy (proportional to the amount of that expansion), which energy begins urging the toe portion back toward its resting unloaded position relative to the other prosthetic elements.

In various embodiments, and depending on factors such as the loading conditions on the prosthesis, Spring 2 can be so stiff that it does not flex open from its rest position—it instead just acts as a "stop" for plantar flexion/toe loading. Preferably, however, Spring 2 provides some degree of gradual and smooth transition from (a) relative movement of the toe portion away from the C-shaped springs 1 and 2 (plantar flexing) to (b) no further relative movement or plantar flexing (the toe portion is no longer moving "away" from the C-shaped springs).

Thus, during a preferred normal heel strike, while Spring 1 is being compressed as the patient shifts weight onto the prosthesis, the inner C (Spring 2) is being expanded because of the plantar flexion of the toe portion of the footplate. As explained below, the opposite condition preferably exists during the toe off/toe loading portion of the wearer's forward stride: at least the inner C (Spring 2) preferably is being "closed/compressed" into a more tightly curved shape than its normal/resting shape, and the outer C (Spring 1) may be expanded/opened beyond its normal/resting shape, from being pulled open by the heel portion of the footplate being flexed away from the C spring(s). In both of these conditions, the prosthetic assembly preferably stores energy that will urge the assembly back into its normal/resting configuration. As also described herein, the preferred uniform thickness and generally smooth curved shape of Springs 1 and 2 make the various loading/unloading conditions feel very smooth and natural to the patient as he or she moves through his/her stride.

Mid-Stance

Mid-stance can be described as the patient's normal standing/resting position, with the footplate in a generally flat and unbent position.

As the wearer continues his stride from heel-strike and approaches and moves into mid-stance, the softness of Spring 1 allows it to gently compress and cushion the patient's impact on the ground or other surface. Eventually, that compression preferably reaches a point where the wearer's weight preferably begins to at least somewhat vertically compress Spring 2. Among other things, this vertical compression "preloads" or stores energy in the inner C Spring 2, which energy can later help the patient during other portions of the wearer's stride (such as toe-off) or other movements.

To achieve this desired pre-loading of Spring 2, some vertical force must be transmitted between the ground and the lower front end of Spring 2. A wide range of structures and methods can be used to accomplish this energy transmission, including preferred embodiments that have one or more compressible elements 55 positioned between the lower/front portions of Spring 2 and the toe portion of the footplate. These compressible elements can be fabricated from any suitable material and can be in any suitable shape and position within the prosthetic assembly. Preferred examples include bladders (which can be filled with air, liquid, or other substances), rubber or foam elements 60, rods inserted or insertable into other elements, solid/flexible/spring-action connecting members, combinations of these or other elements that are relatively softer/harder (or even incompressible), and others.

Figure 14A:
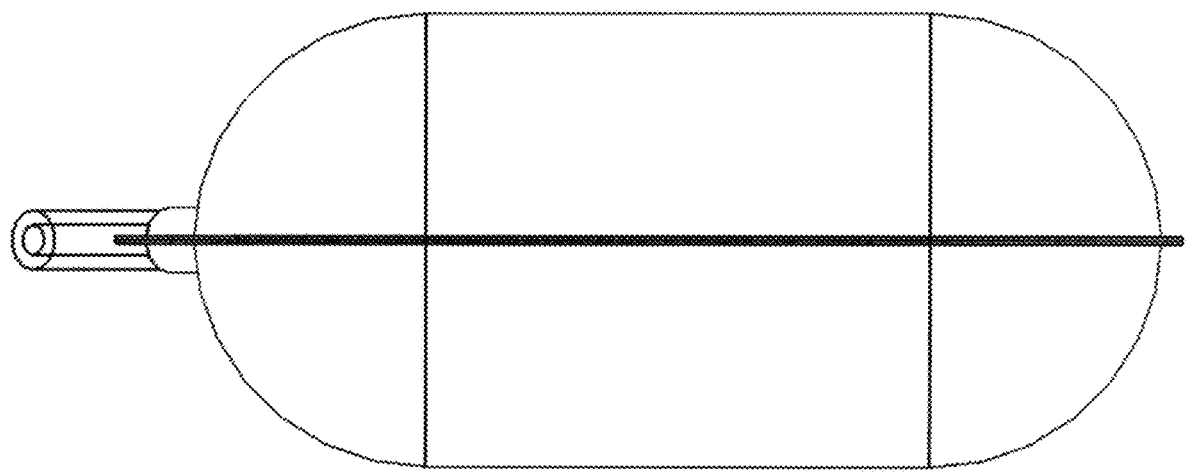
FIGS. 14a and 14b are side views of a bladder element in accordance with an embodiment of the present invention.
Figure 14B:
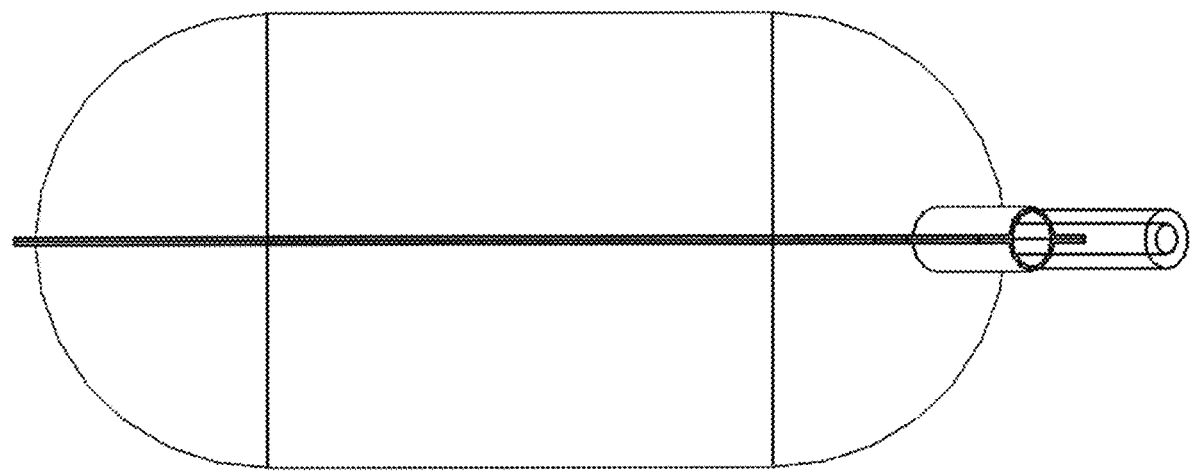
Figure 14C:
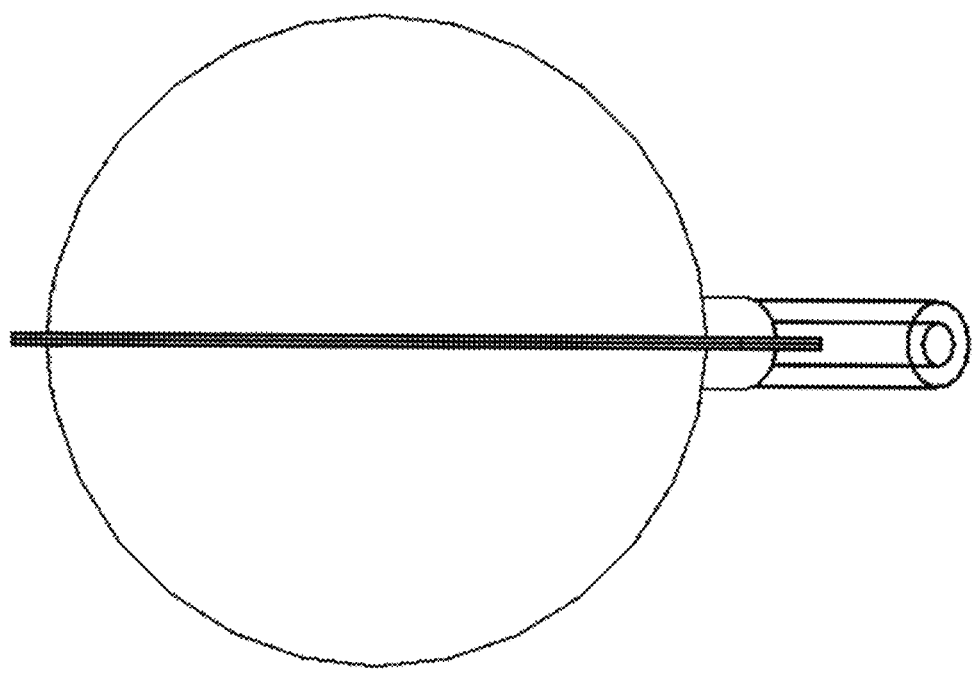
FIG. 14c is an end view of a single bladder having a single tube in accordance with an embodiment of the present invention.
Figure 15A:
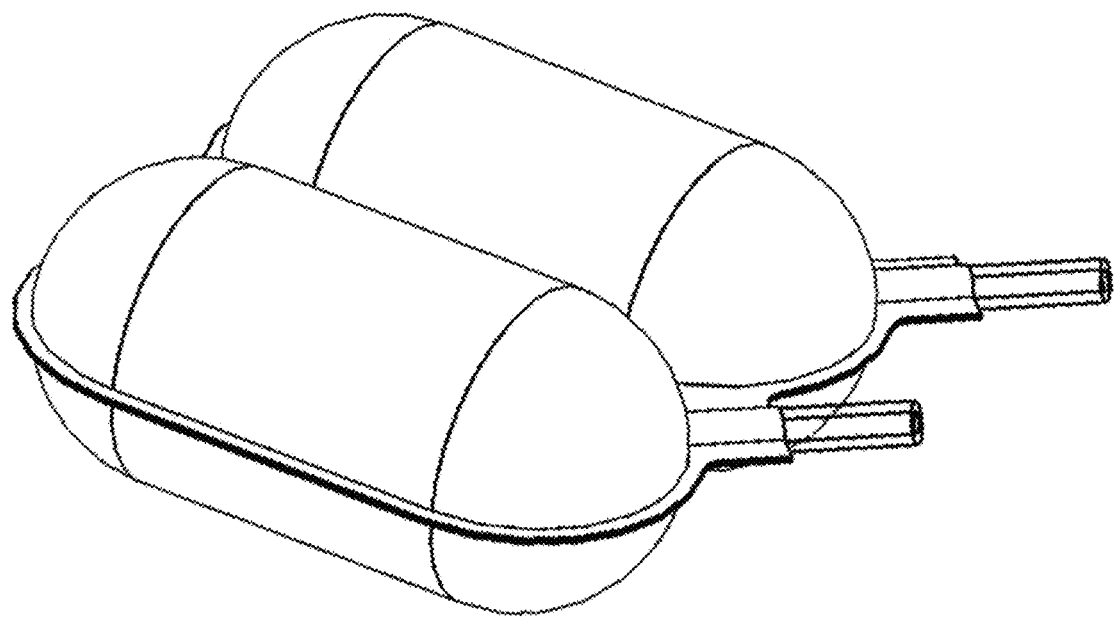
FIGS. 15a, 15b, and 15c are isometric views of a double bladder having double tubes in accordance with another embodiment of the present invention.
Figure 15B:
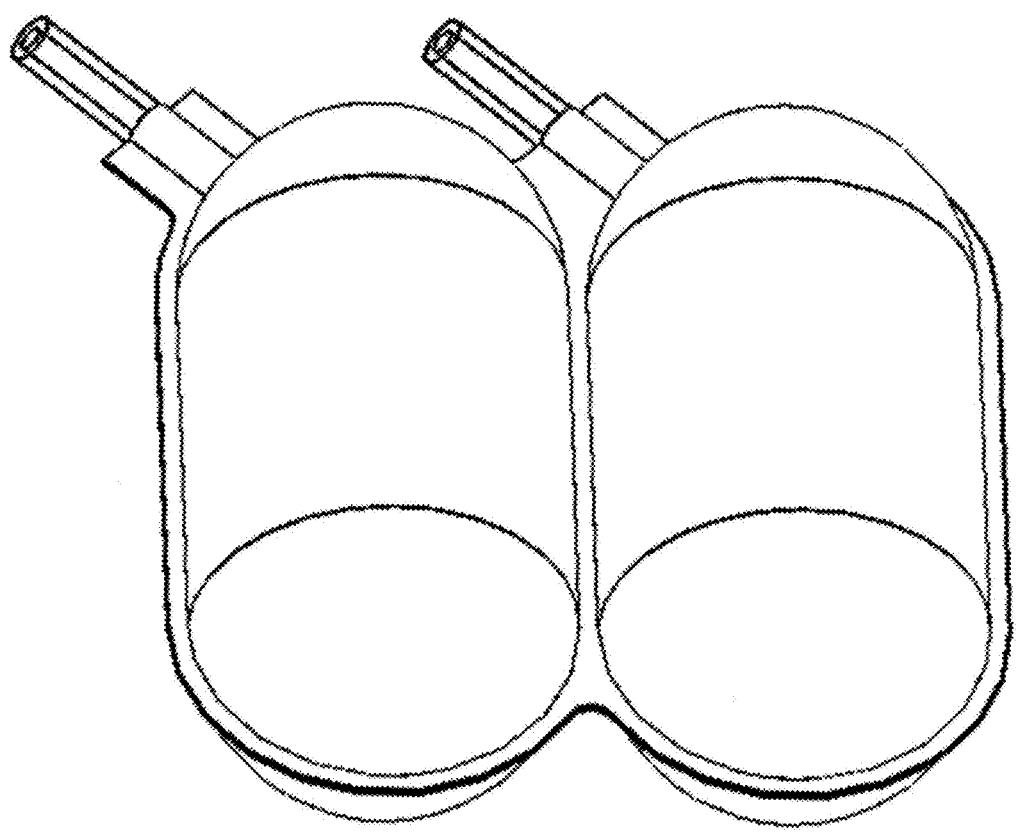
Figure 15C:
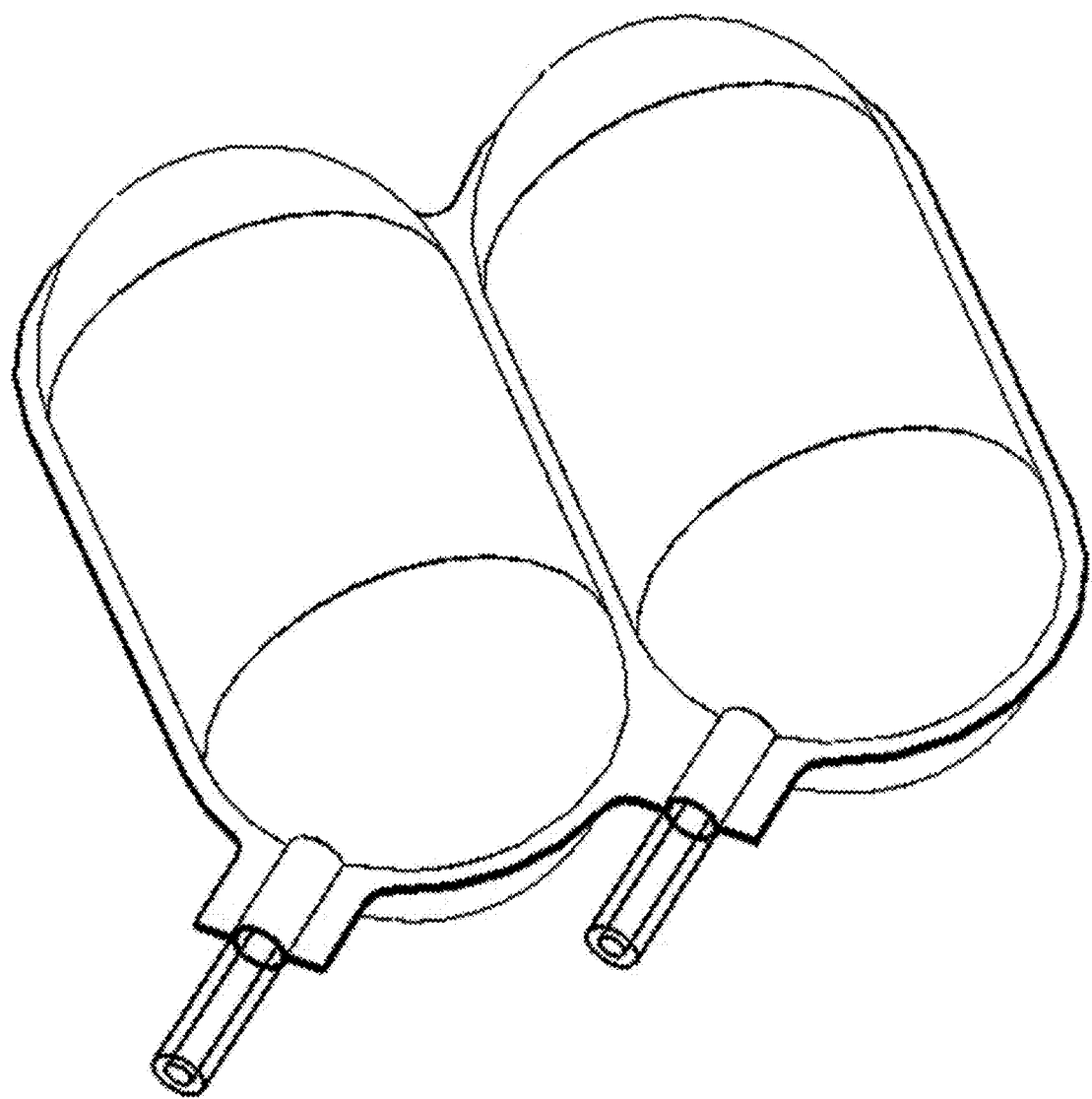
Figure 15D:
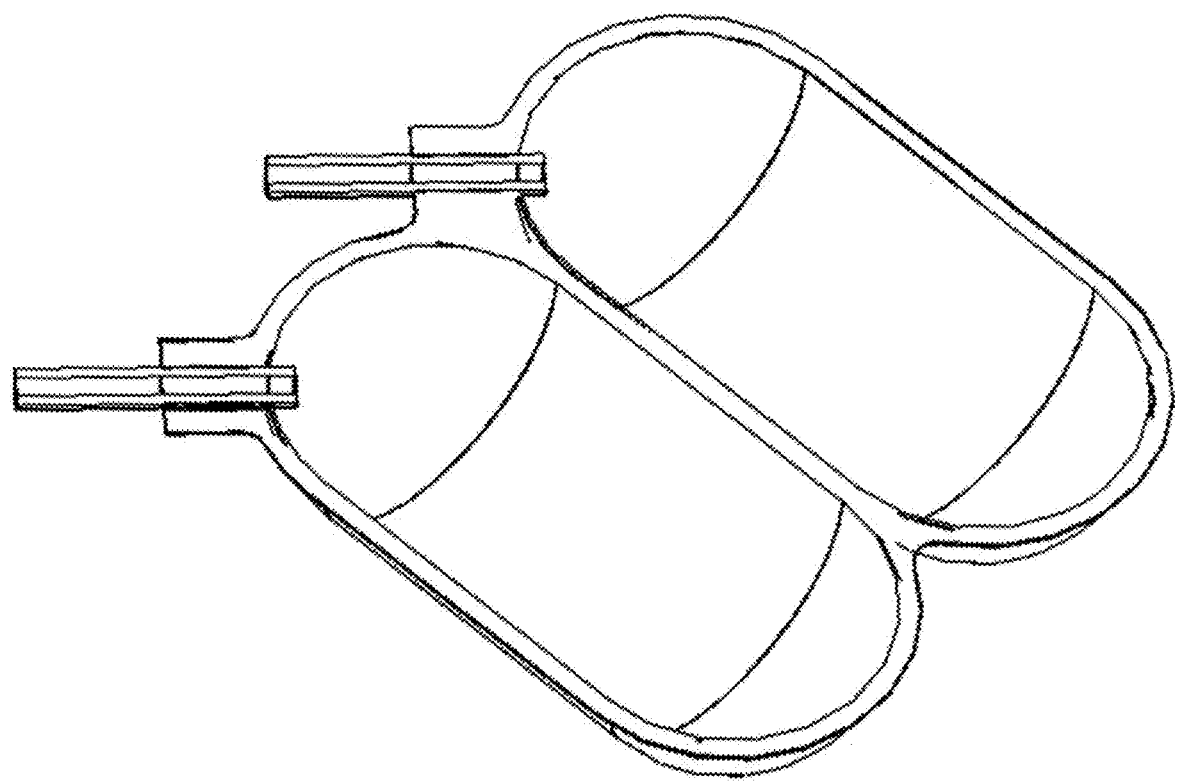
FIG. 15d is an isometric section view of the double bladder embodiment shown in FIGS. 15a, 15b, and 15c.
Figure 15E:
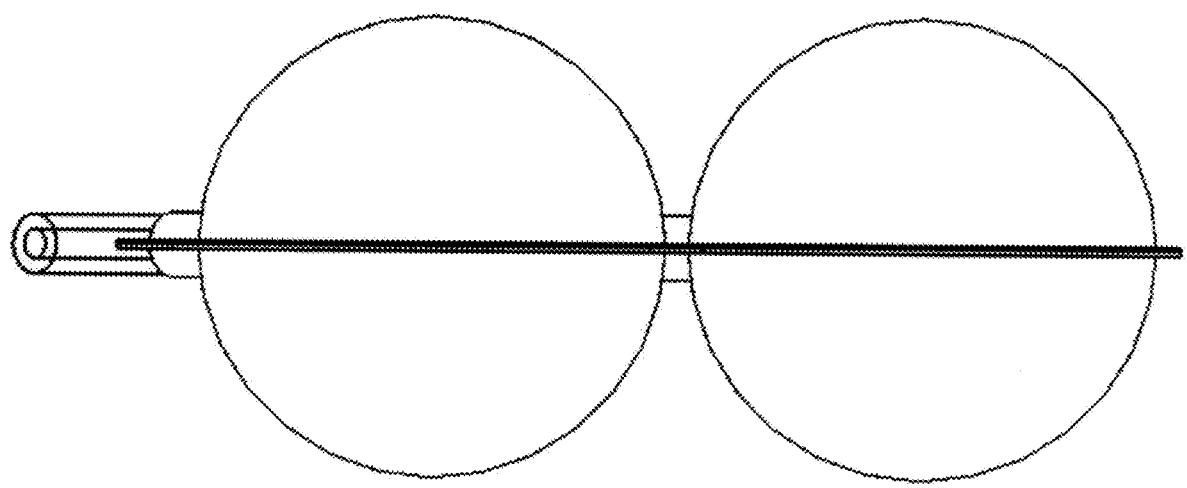
FIG. 15e an end view of the double bladder embodiment shown in FIGS. 15a, 15b, and 15c.
Figure 15F:
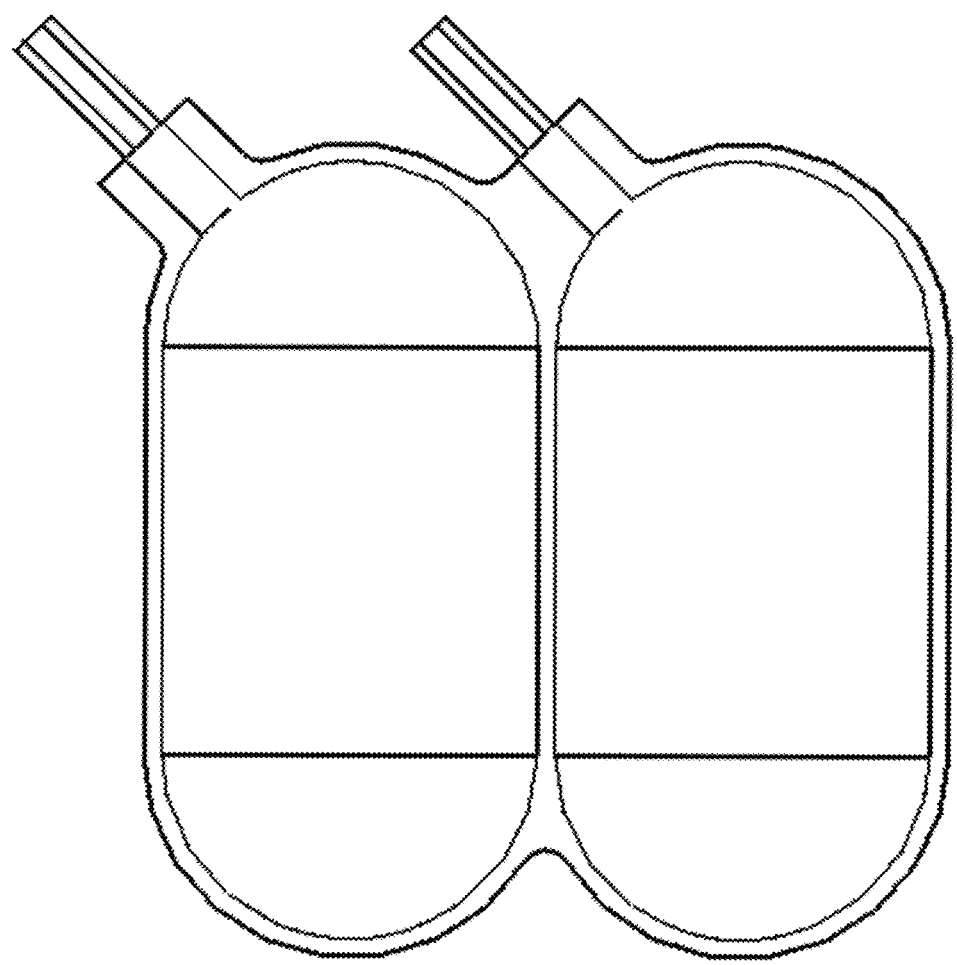
FIG. 15f is top view of the double bladder embodiment shown in FIGS. 15a, 15b, and 15c.
Figure 16A:
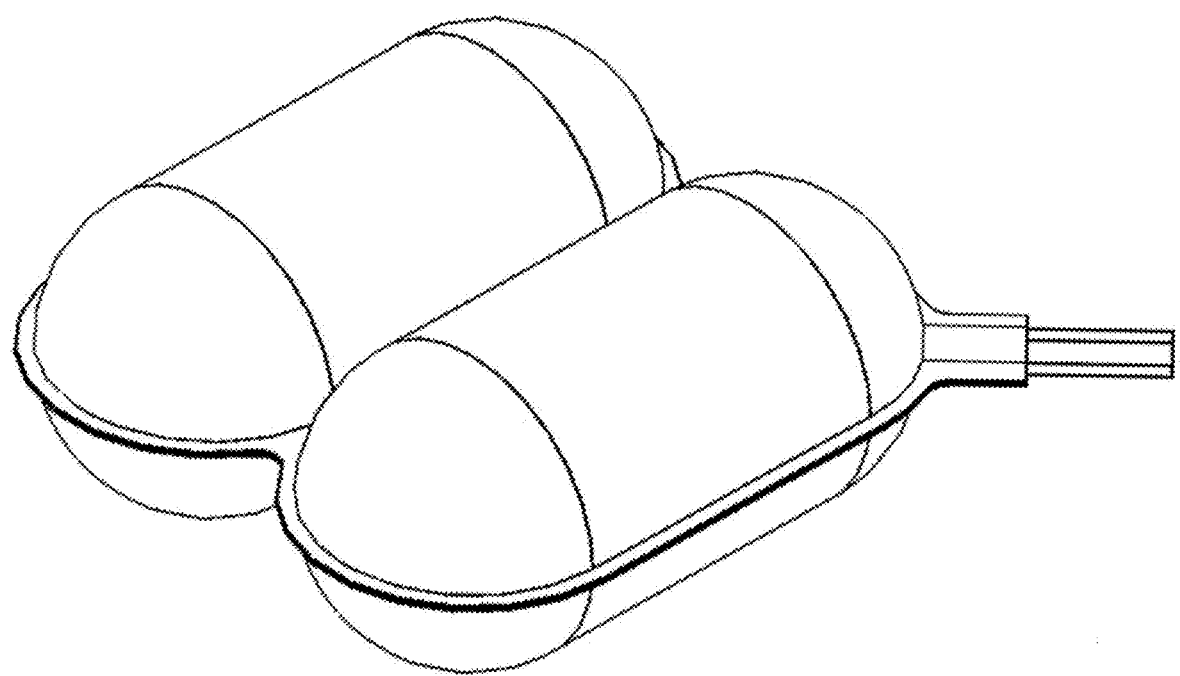
FIGS. 16a and 16b are isometric views of a double bladder having a single tube in accordance with another embodiment of the present invention.
Figure 16B:
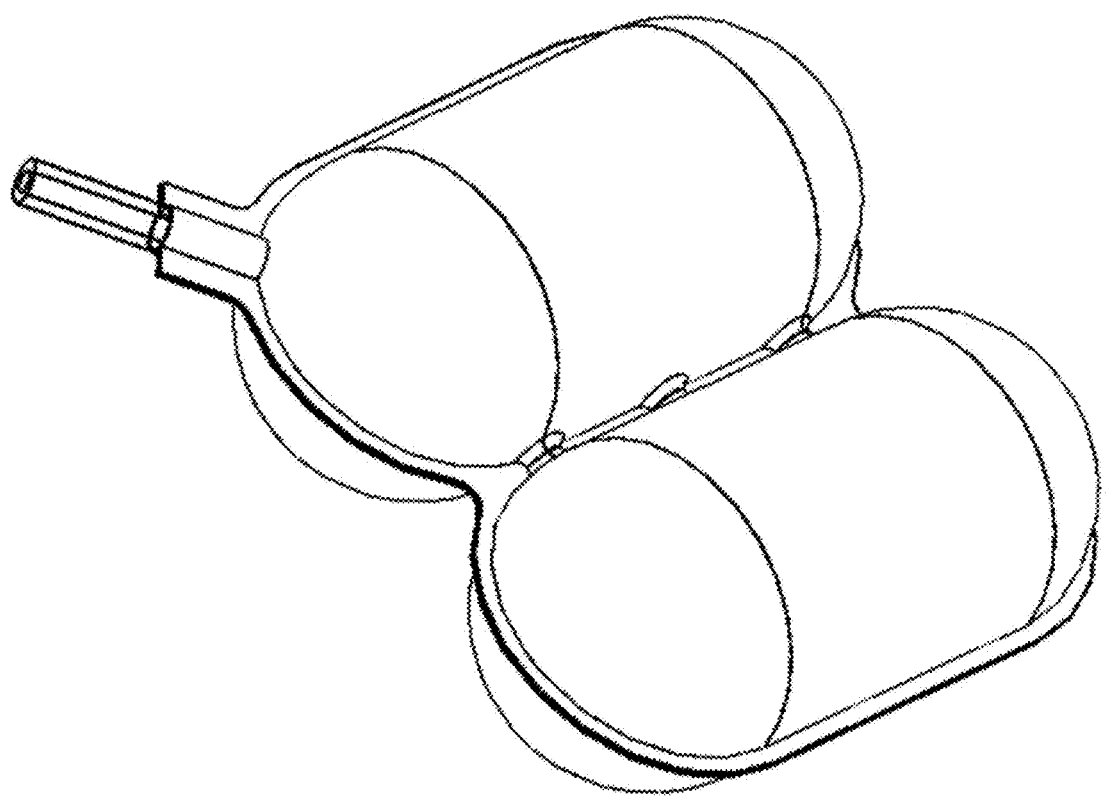
Figure 16C:
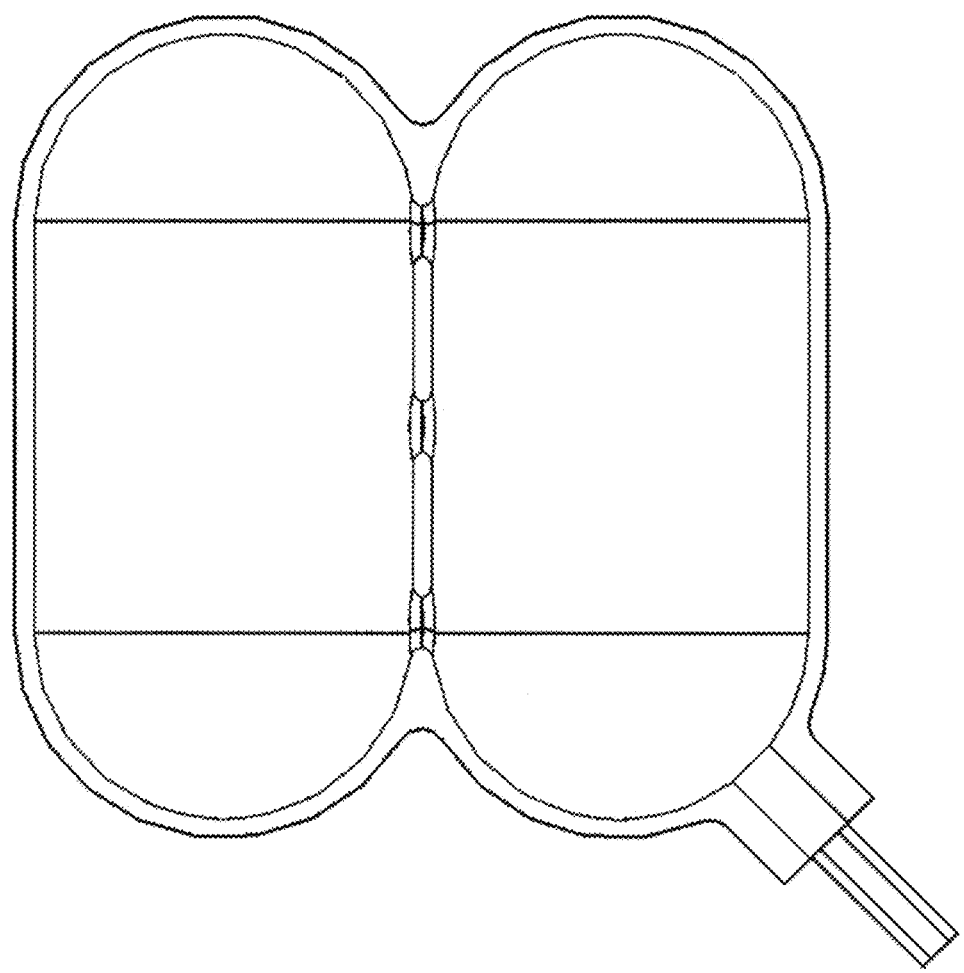
FIG. 16c is a bottom view of the double bladder with single tube embodiment shown in FIGS. 16a and 16b.
Figure 16D:
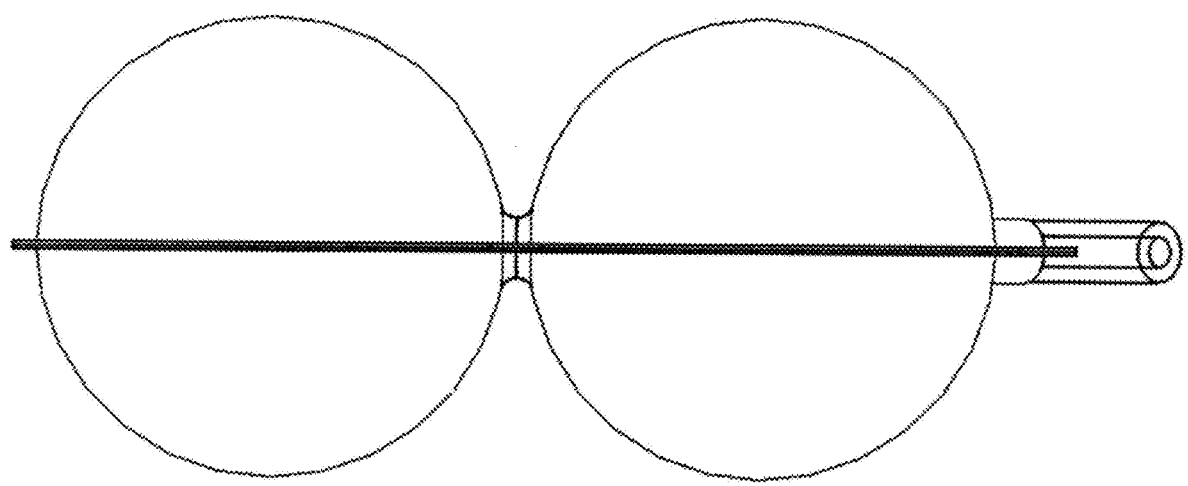
FIGS. 16d and 16e are end views of the double bladder with single tube embodiment shown in FIGS. 16a and 16b.
Figure 16E:
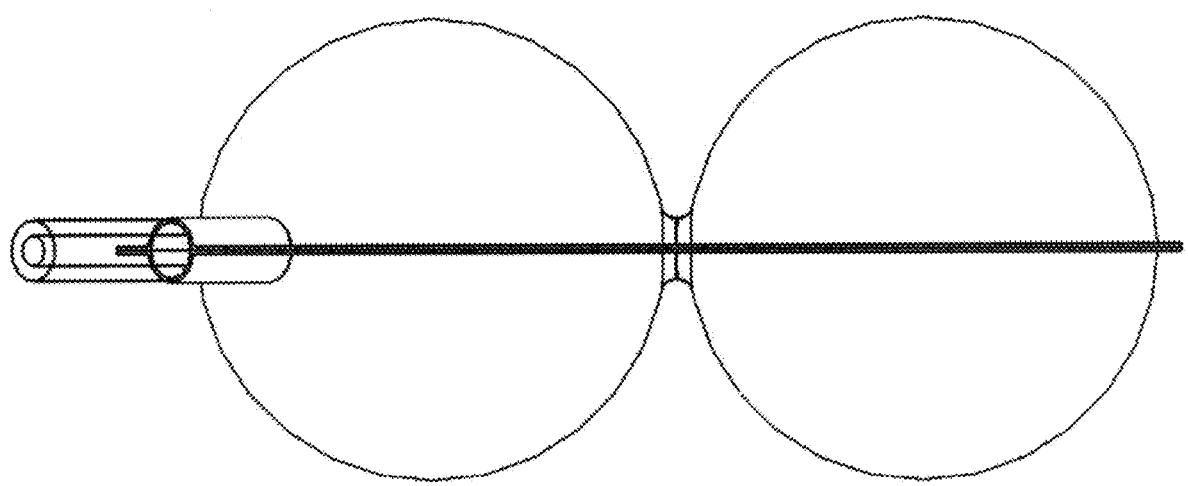
Figure 16F:
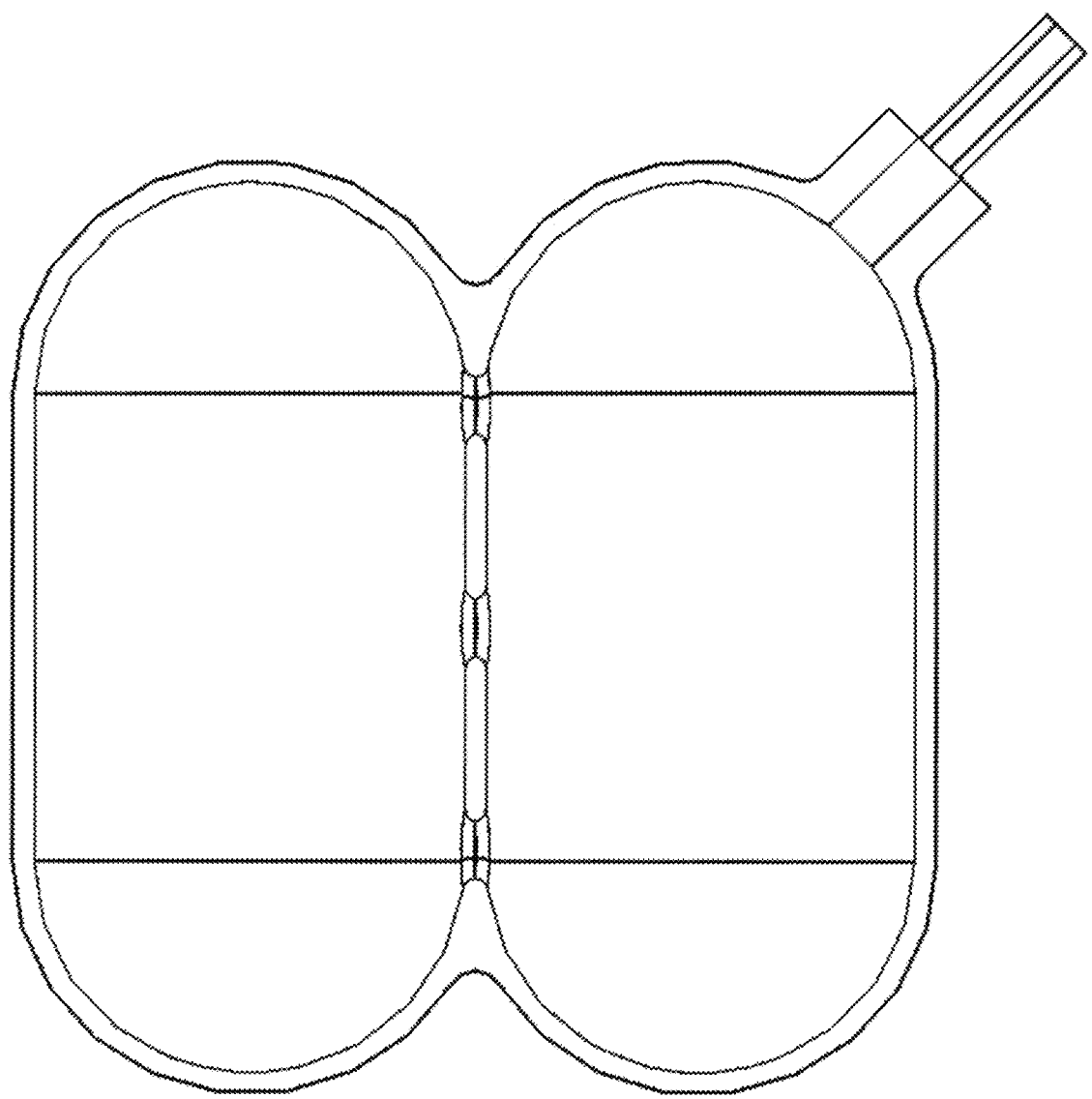
FIG. 16f is a top view of the double bladder with single tube embodiment shown in FIGS. 16a and 16b.
Figure 16G:
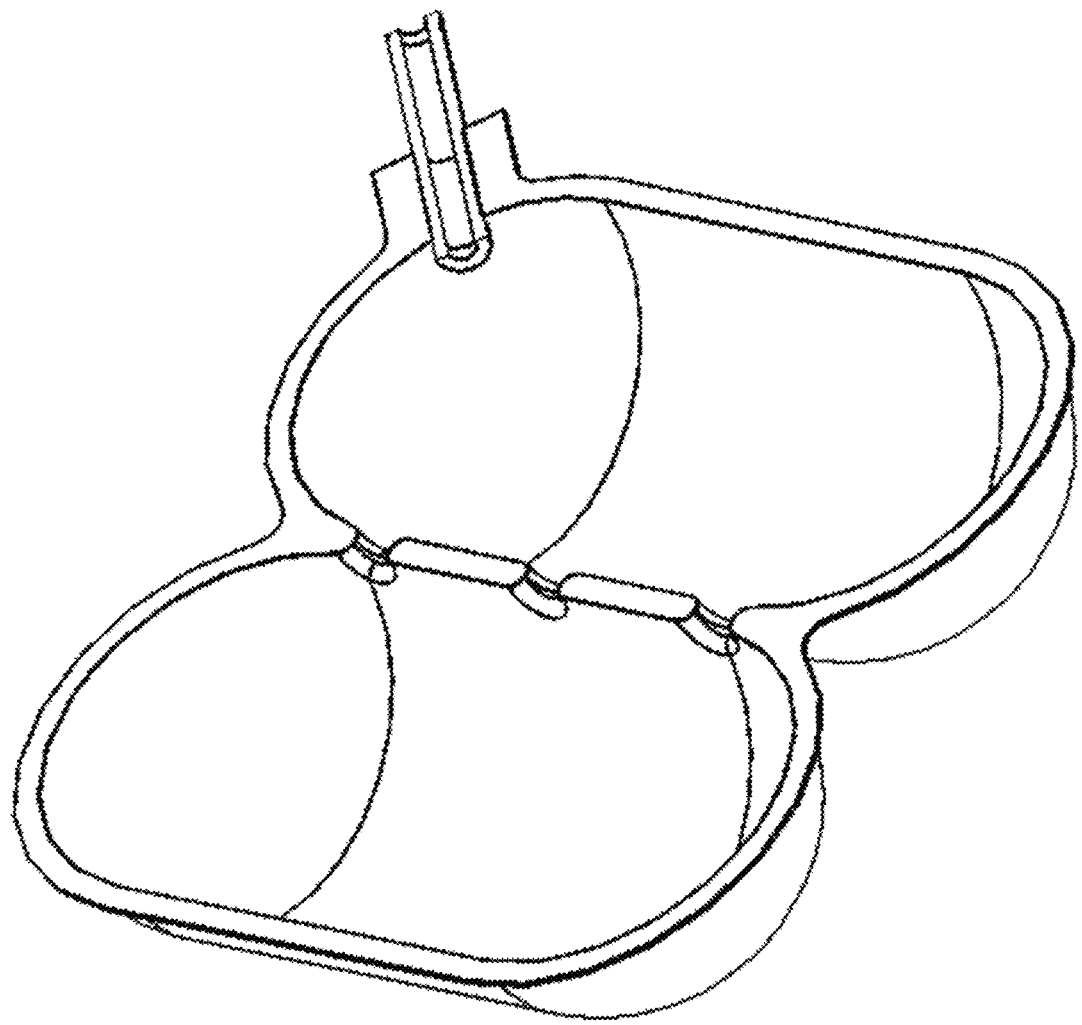
FIGS. 16g, 16h, 16i, and 16j are isometric section views of the double bladder with single tube embodiment shown in FIGS. 16a and 16b.
Figure 16H:
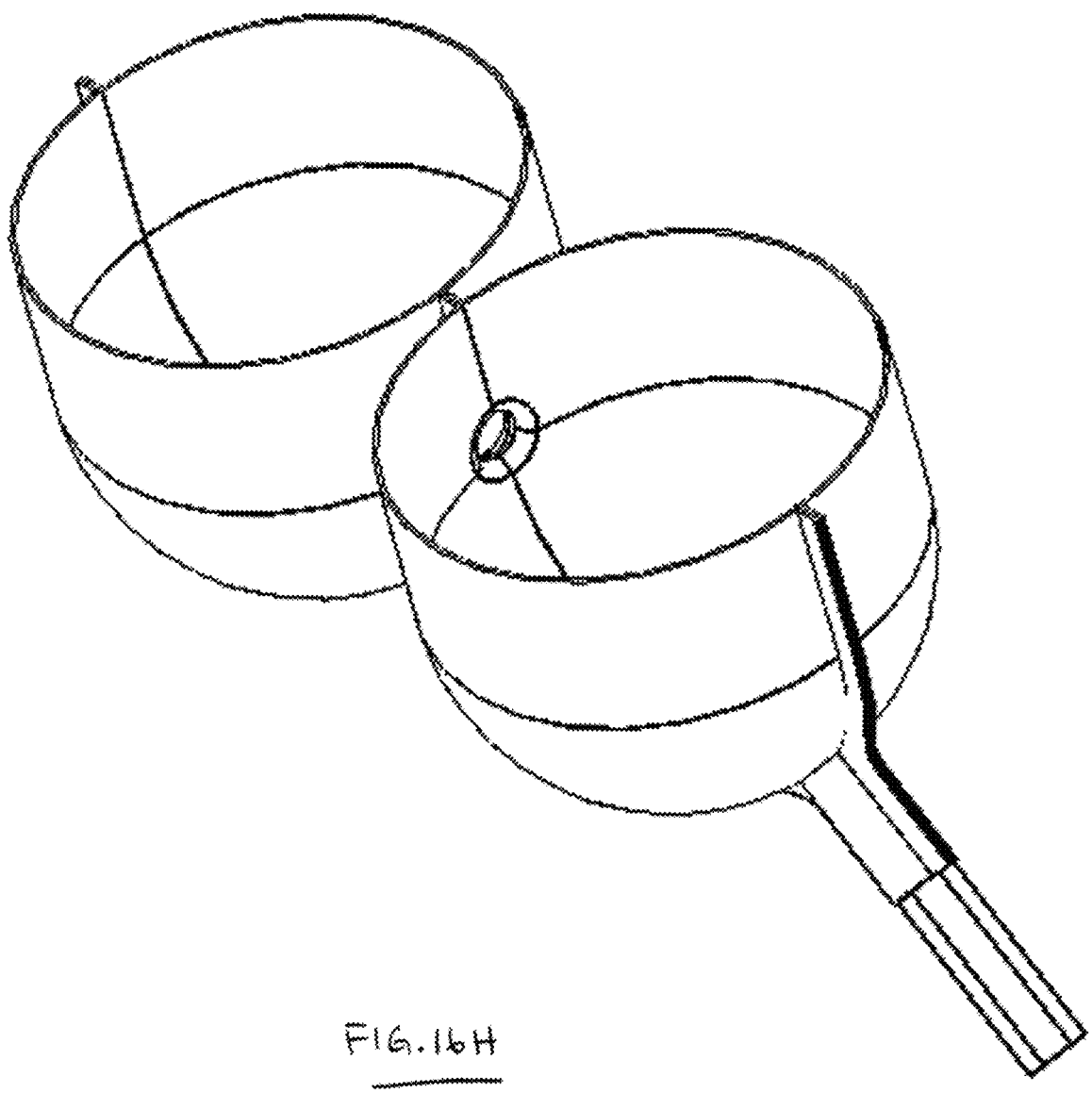
Figure 16I:
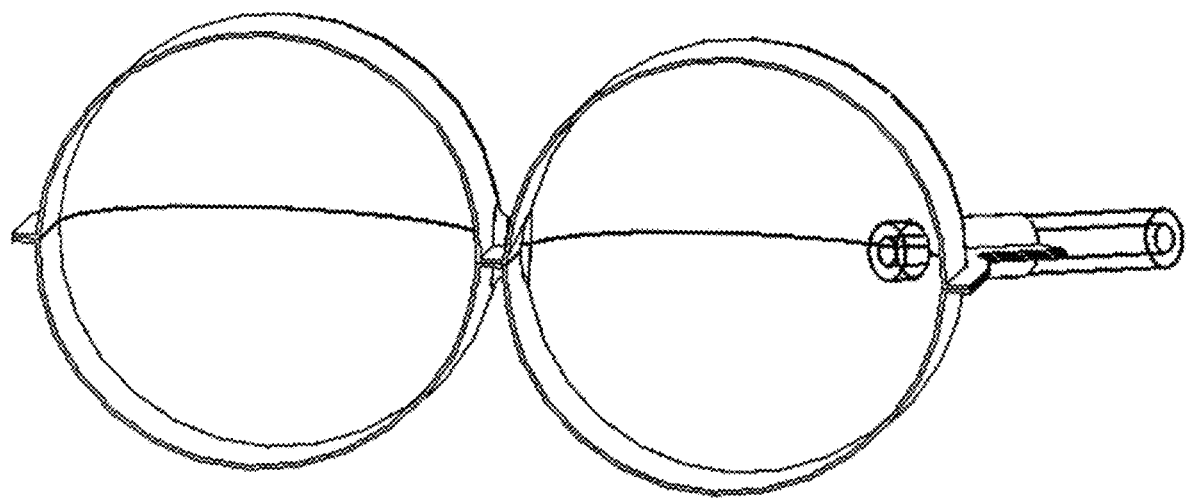
Figure 16J:
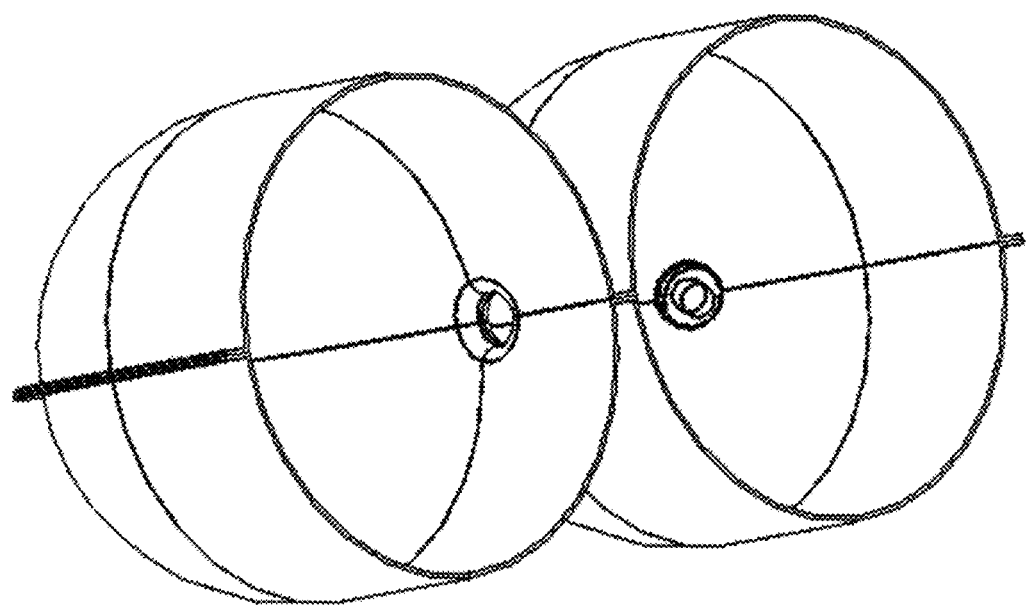
Figure 17:
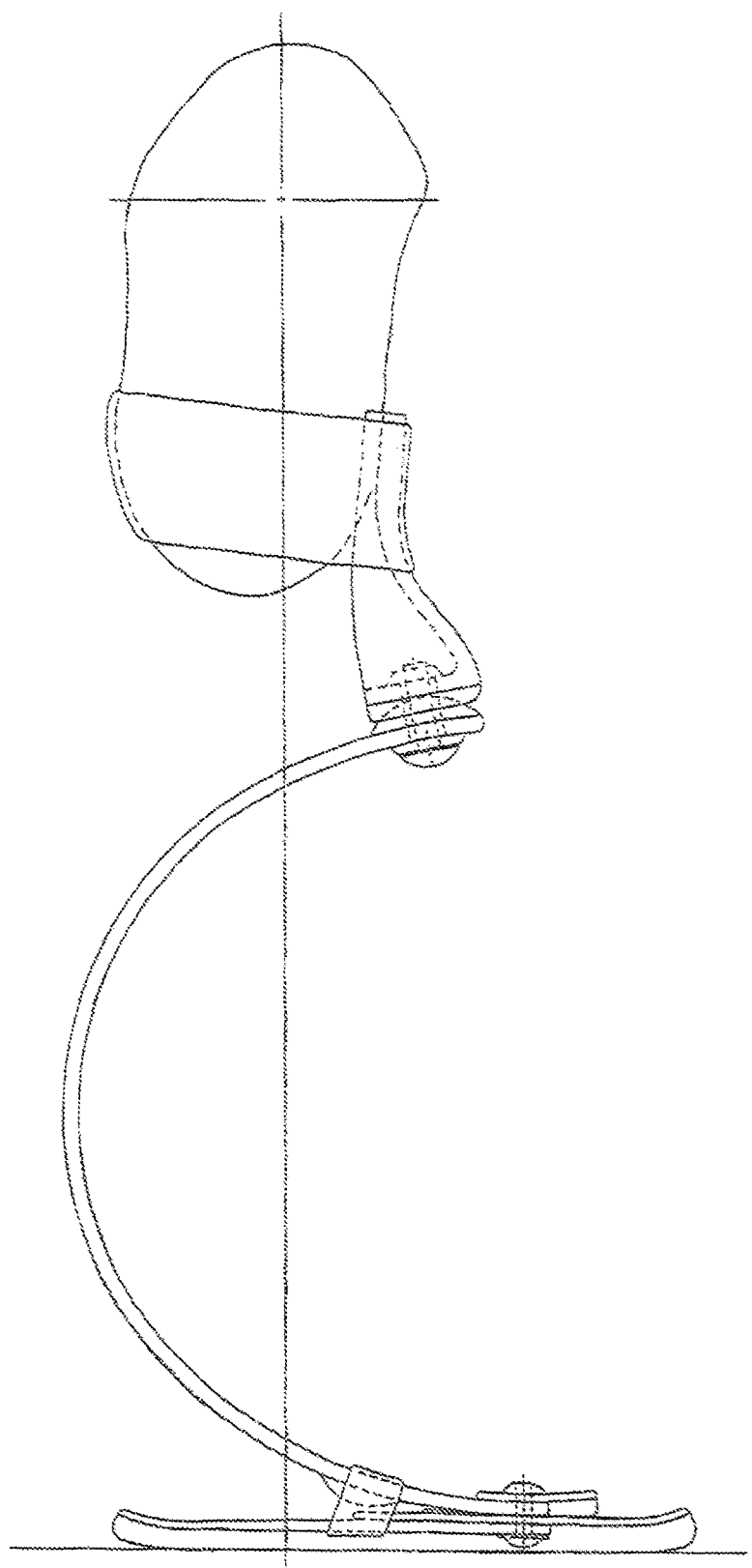
FIGS. 17, 17A, 17B, and 18 through 25 are elevation views illustrating some of the many other various combinations and permutations that can be used to practice the invention.
Figure 17A:
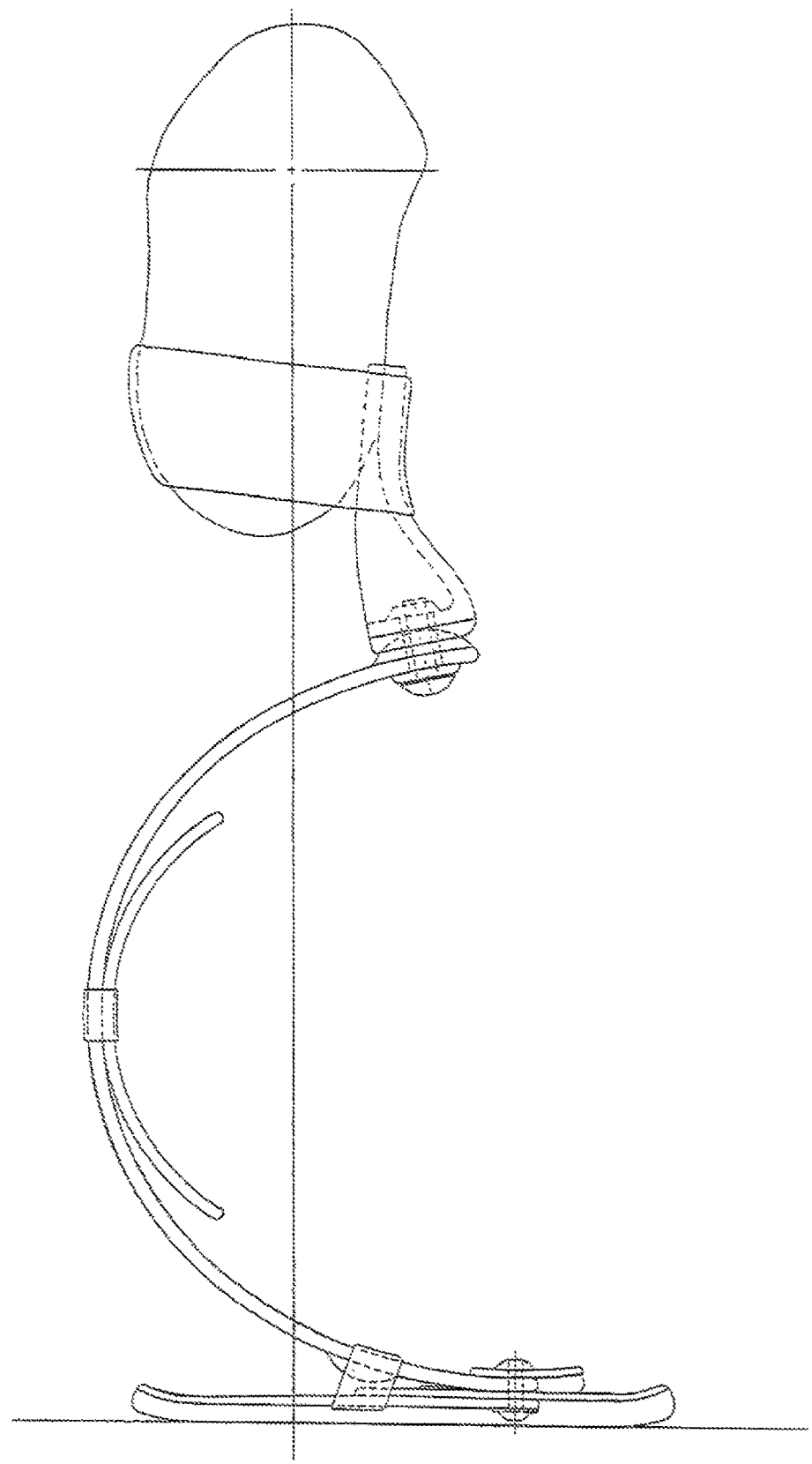
Figure 17B:
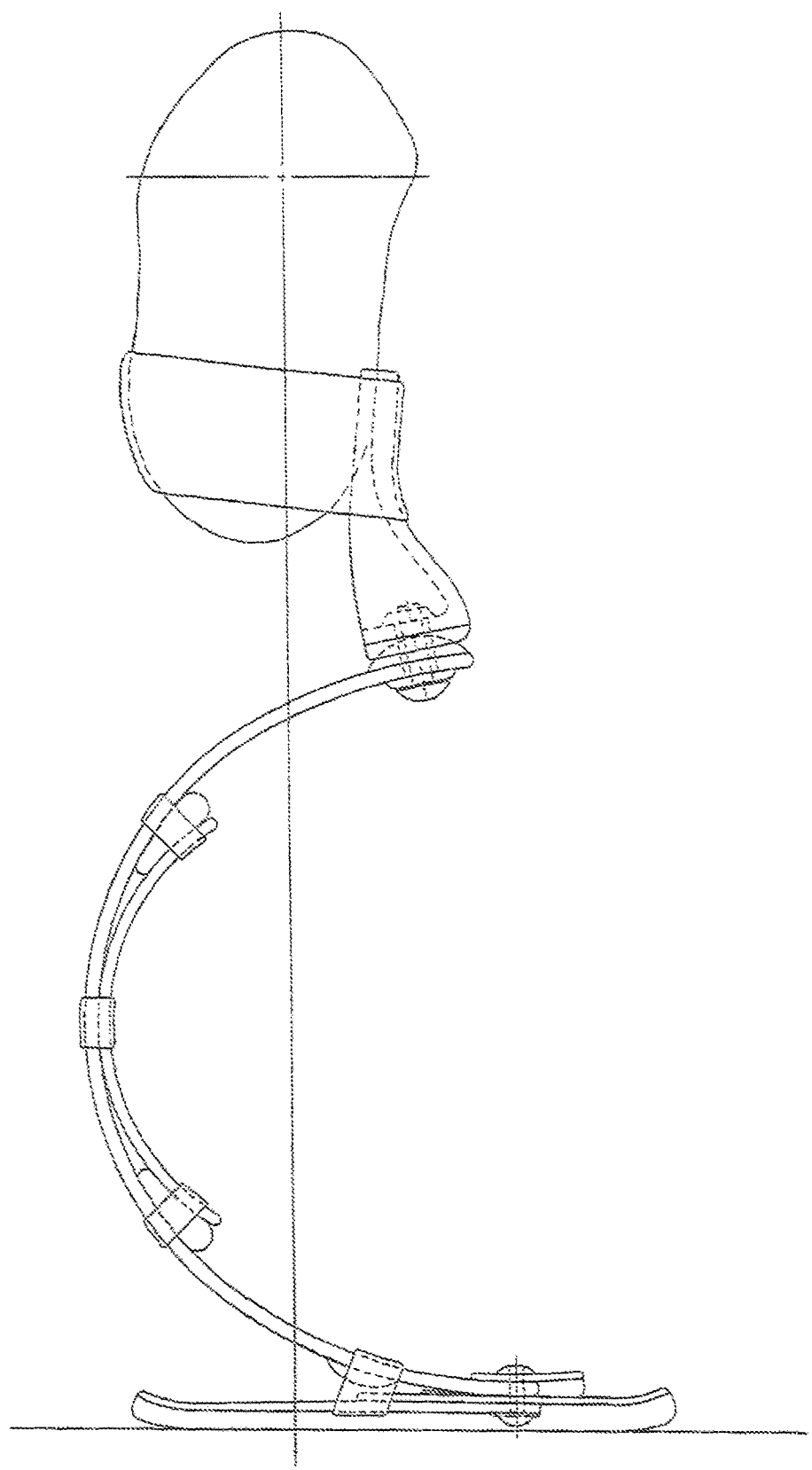
Figure 18:
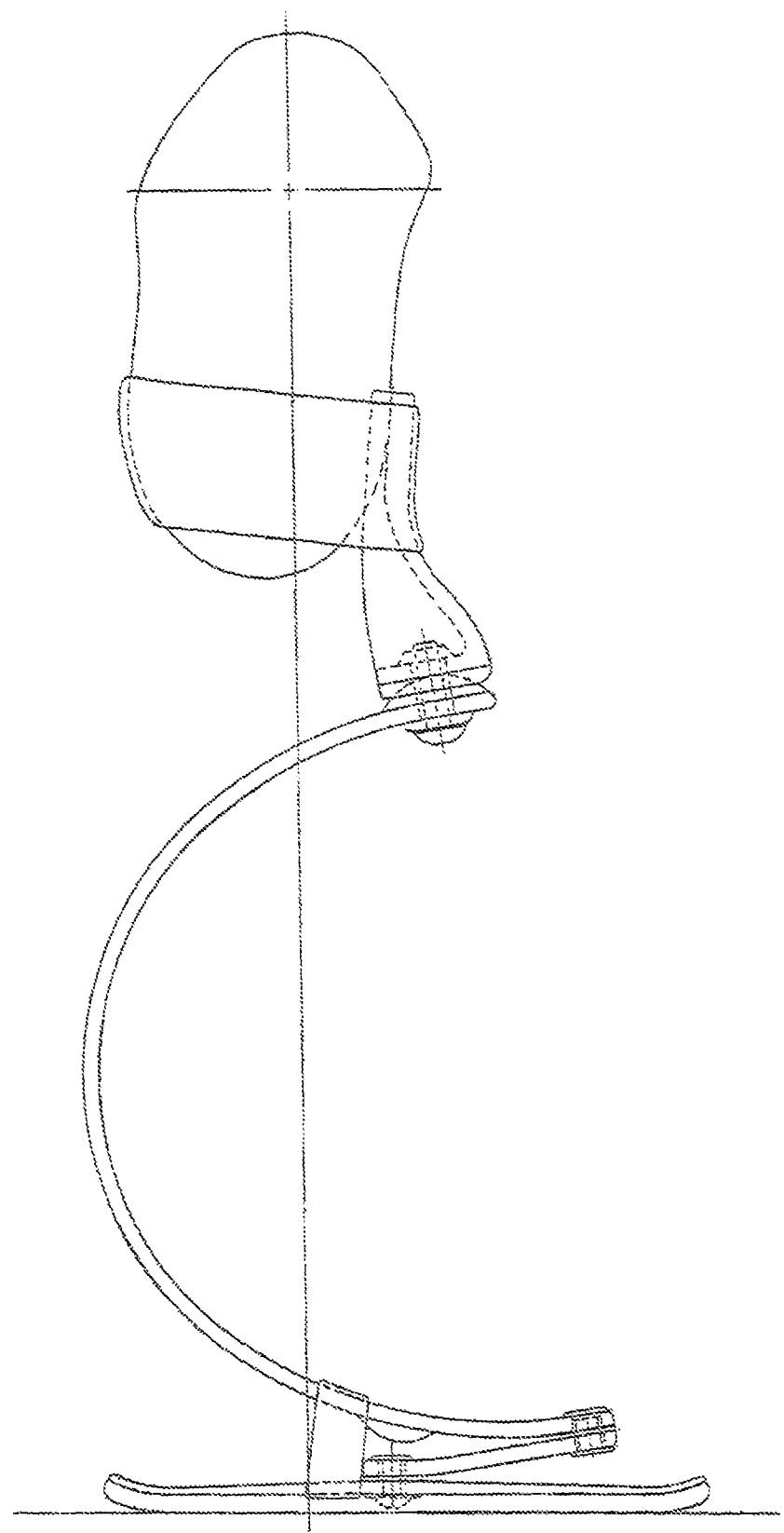
Figure 19:
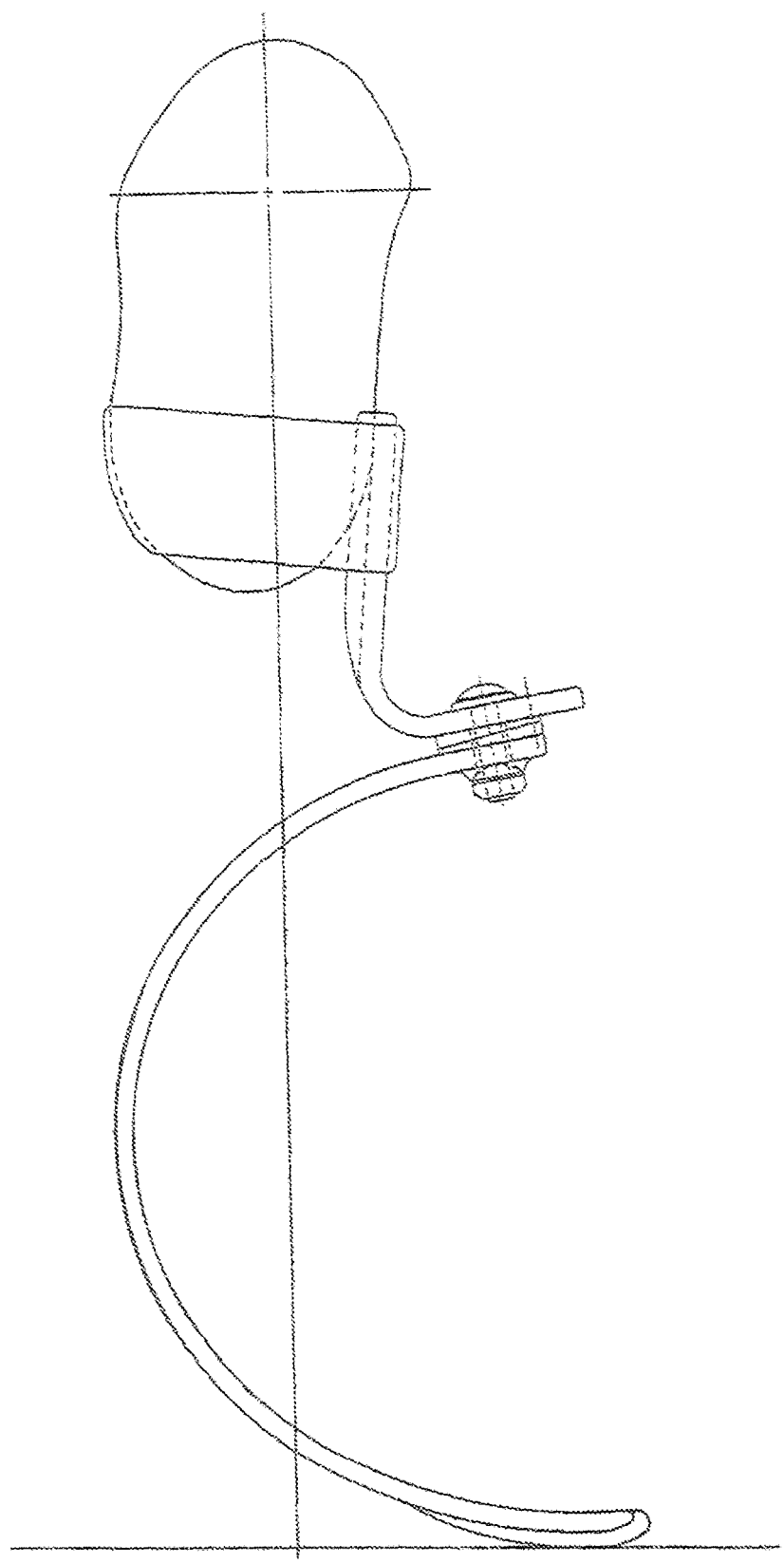
Figure 20:
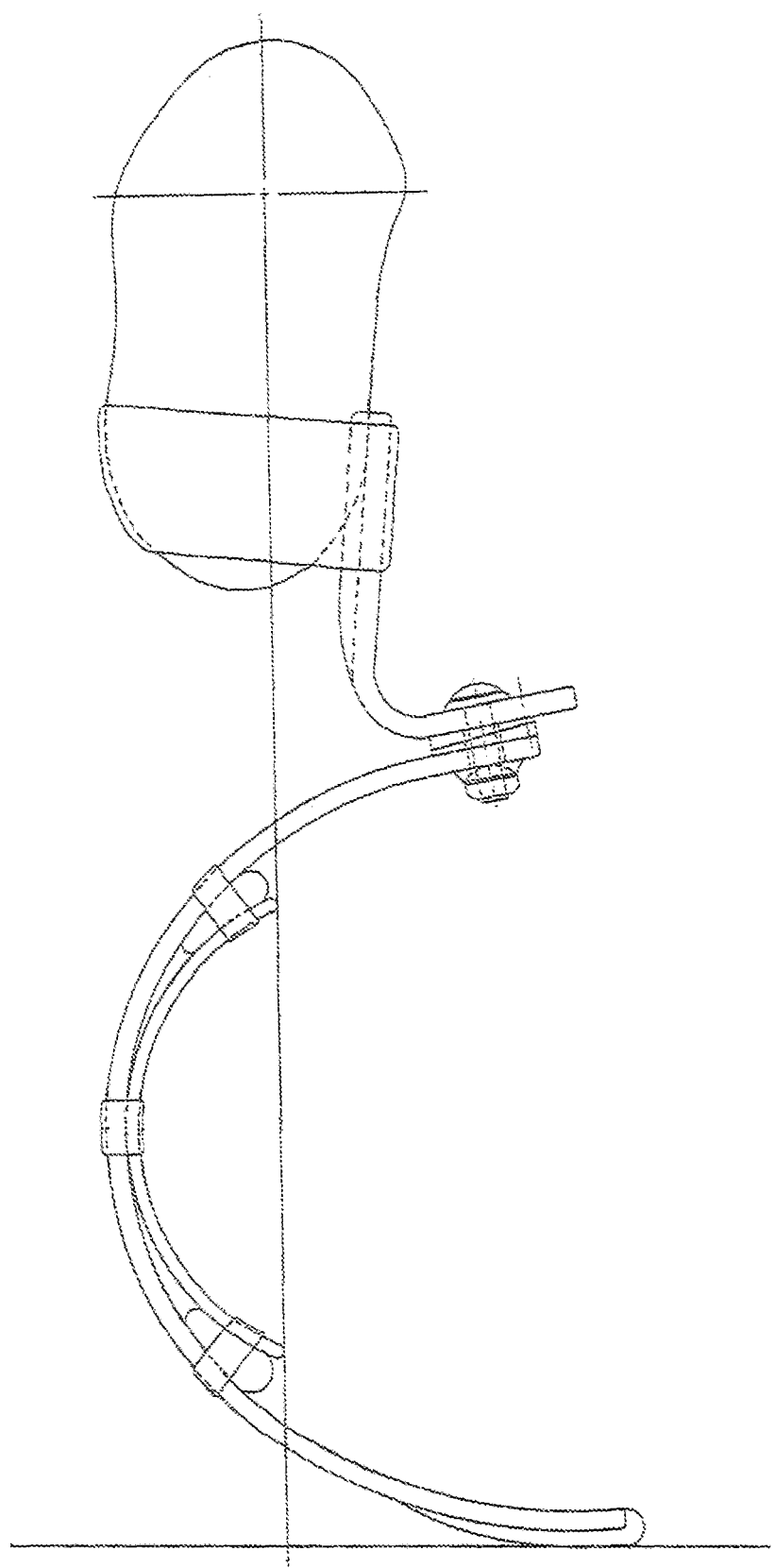
Figure 21:
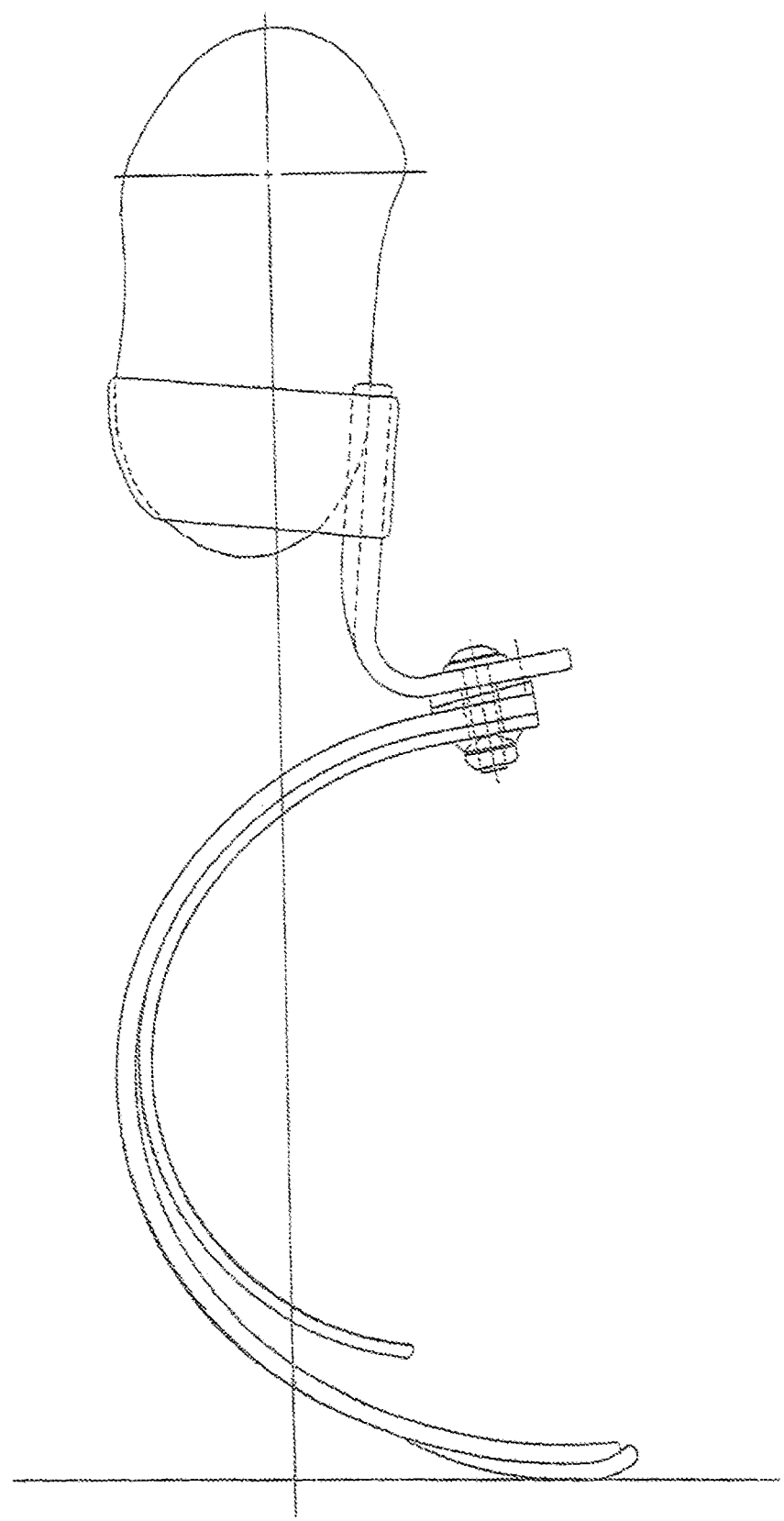
Figure 22:
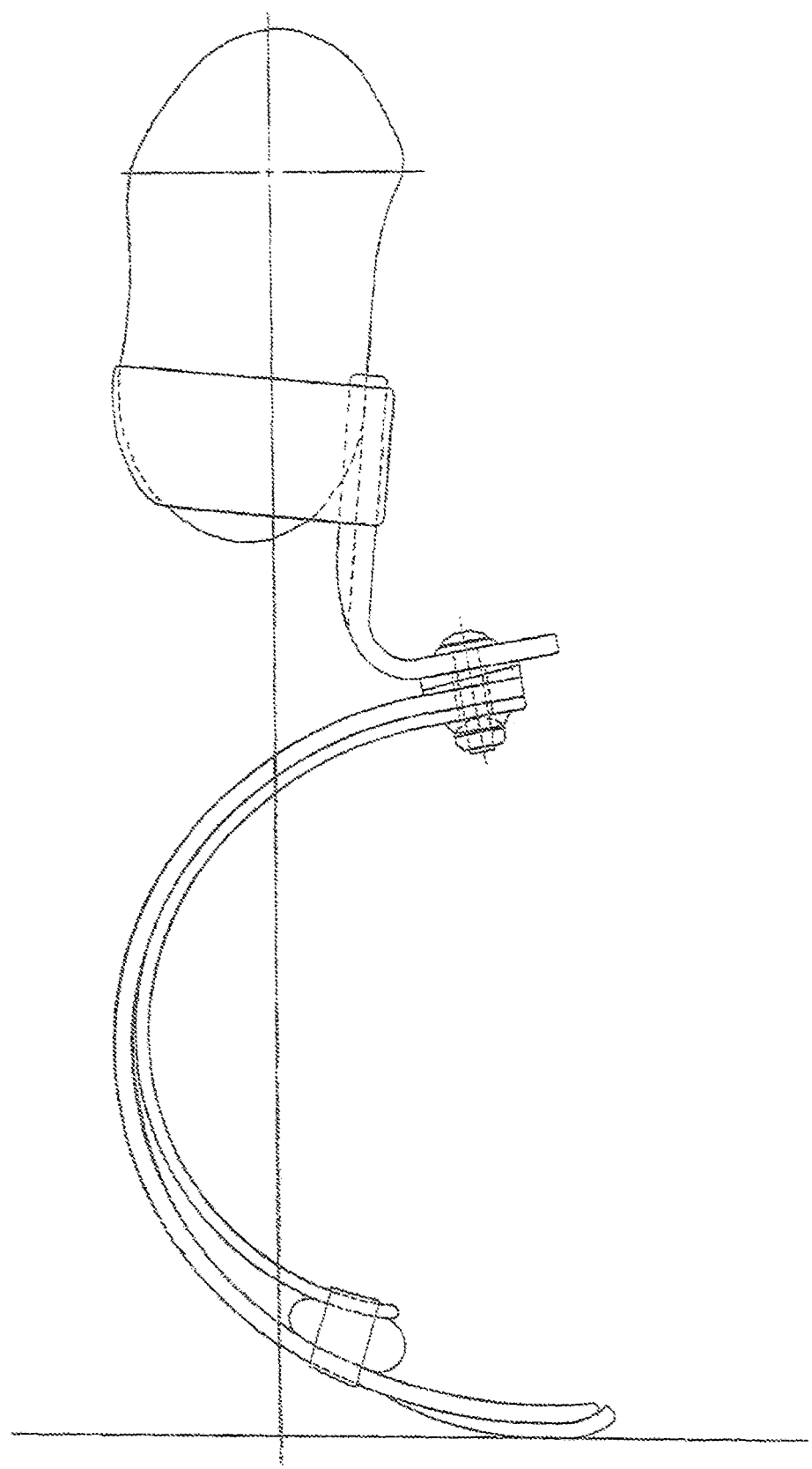
Figure 23:
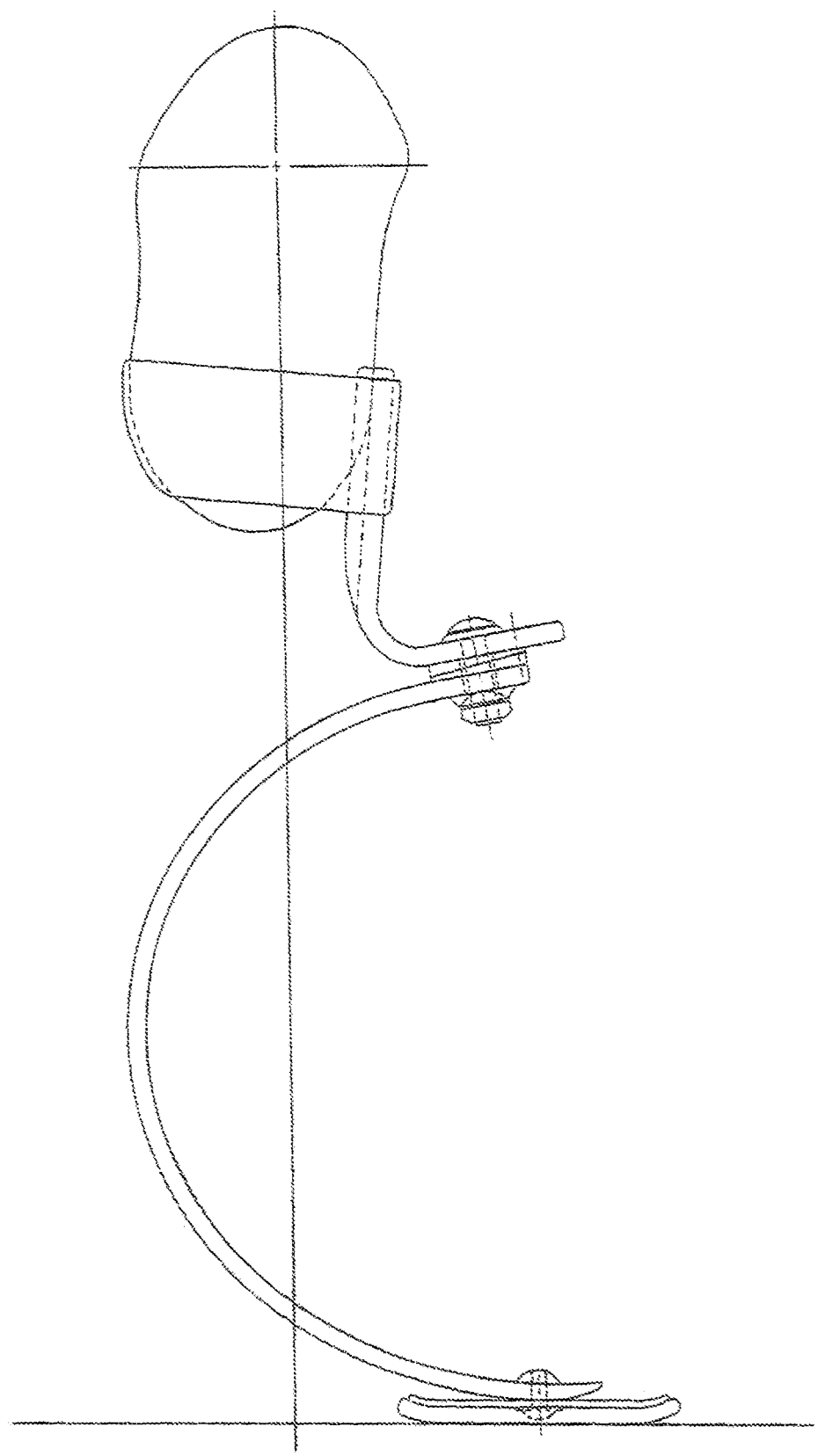
Figure 24:
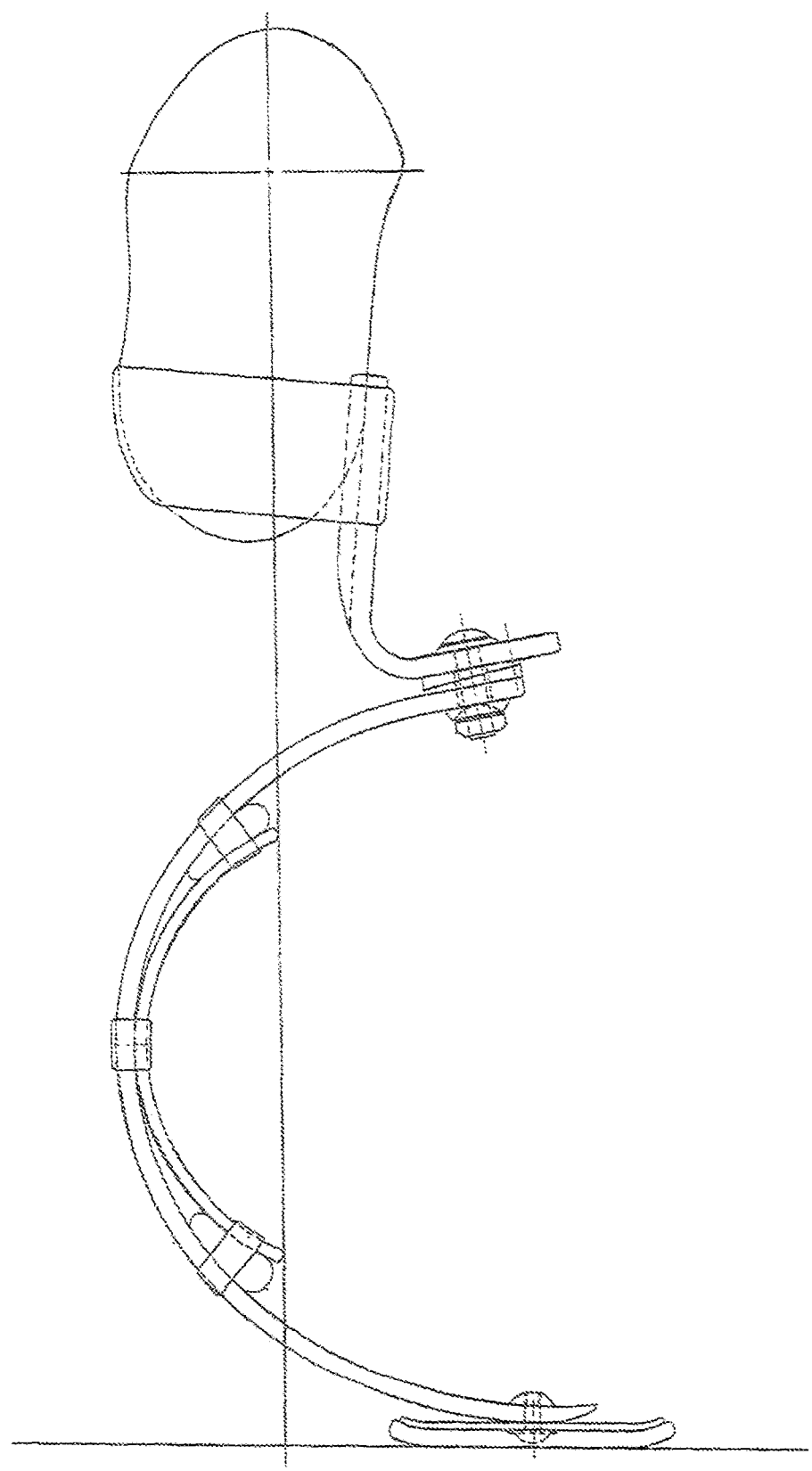
Figure 25:
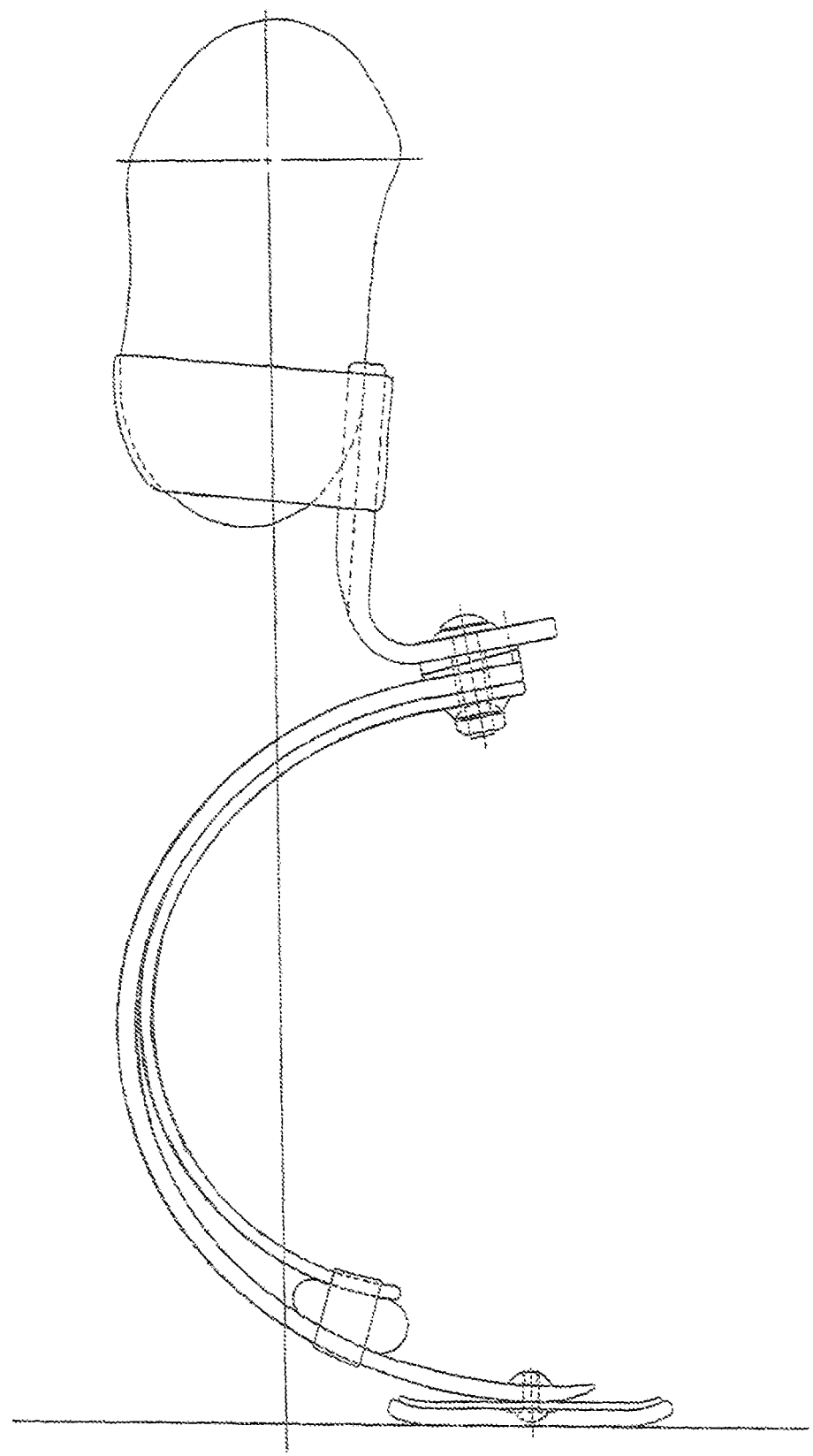
Figure 26:
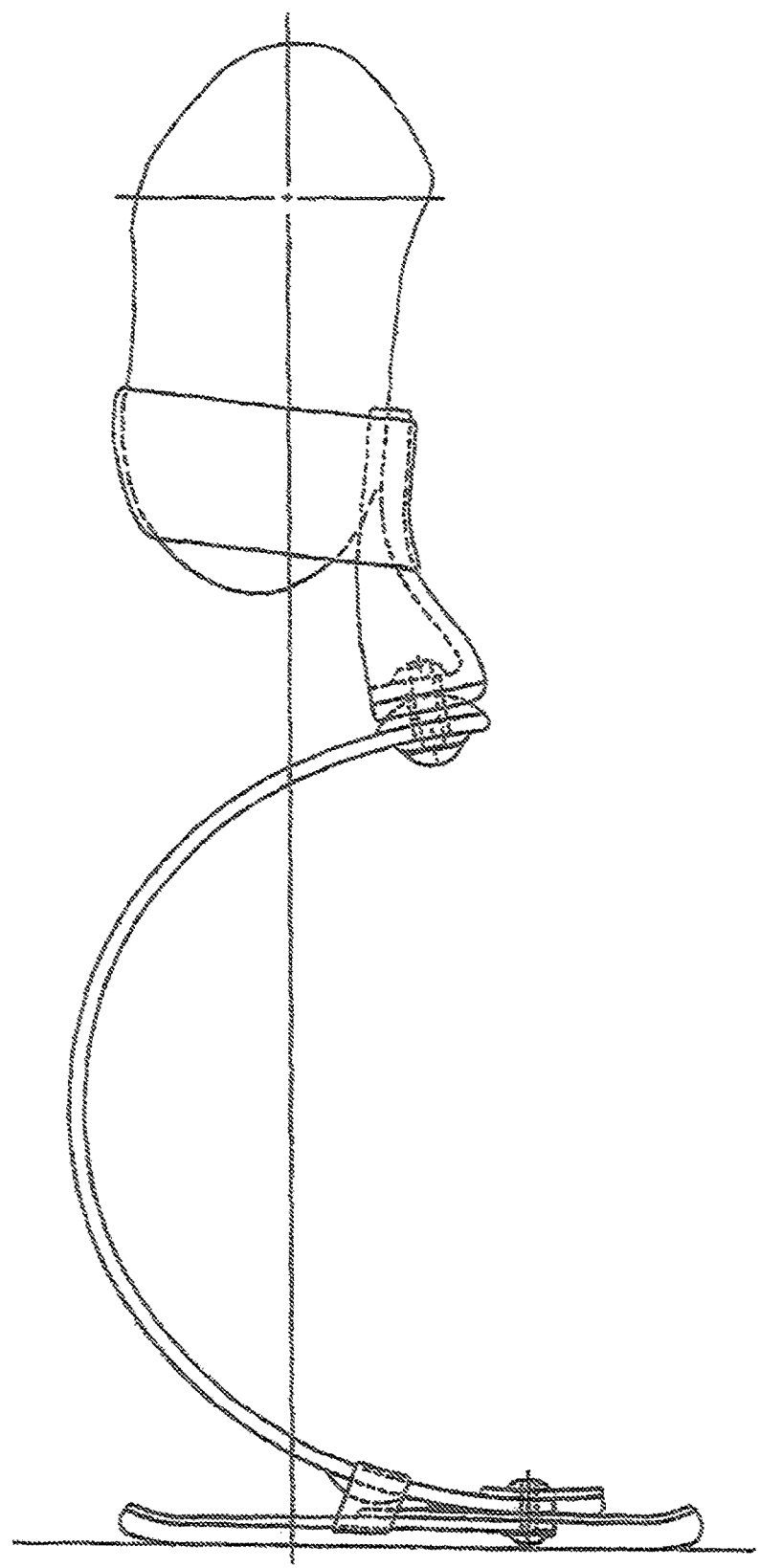
FIG. 26 is an overlay of two of the embodiments from the other drawings, for comparison purposes.
Figure 27:
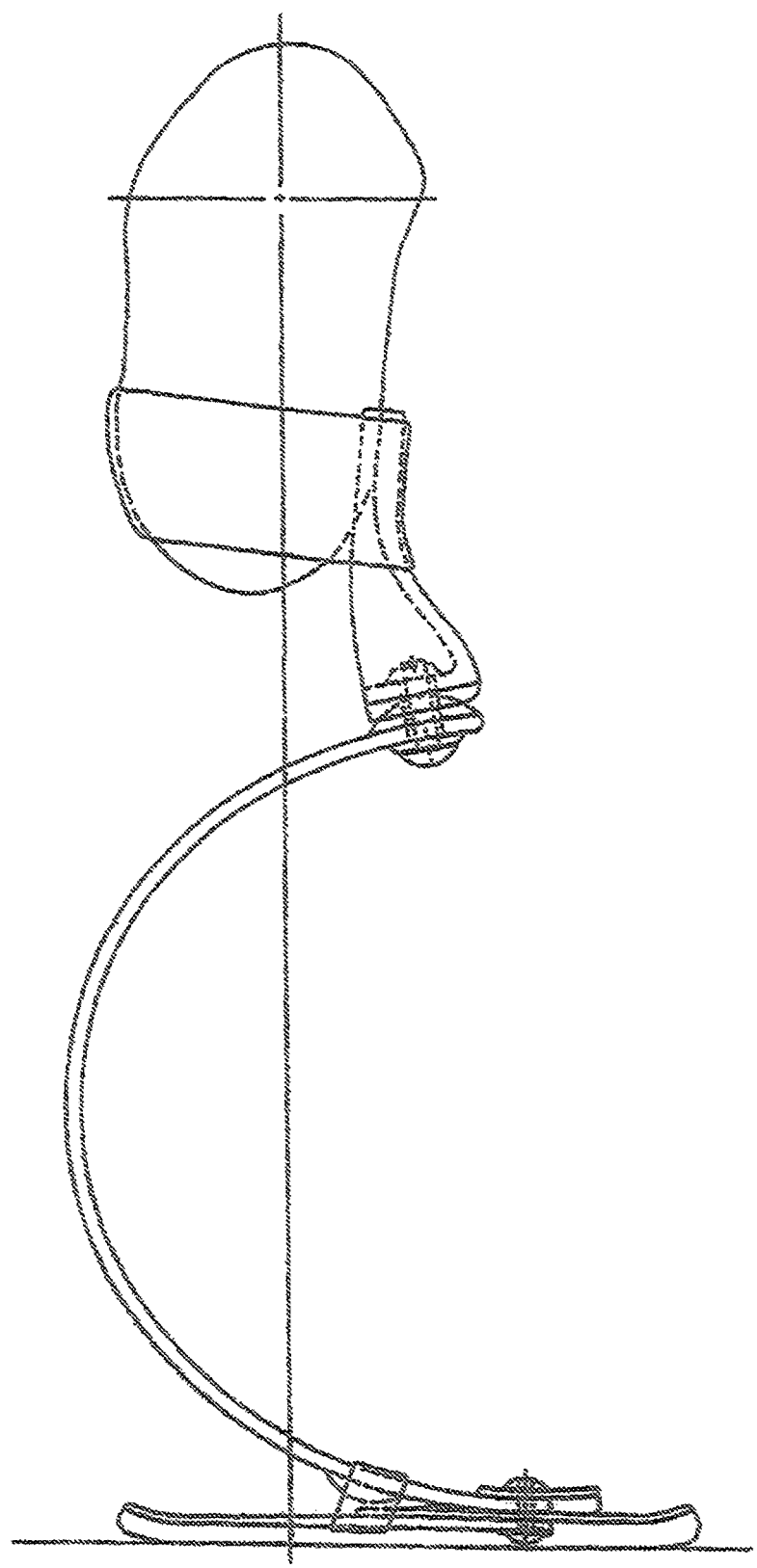
FIG. 27 is similar to FIG. 26, but instead of aligning the sockets, the spring elements are generally aligned, and the differences in the positioning and orientation of the socket elements can be seen.
Figure 28:
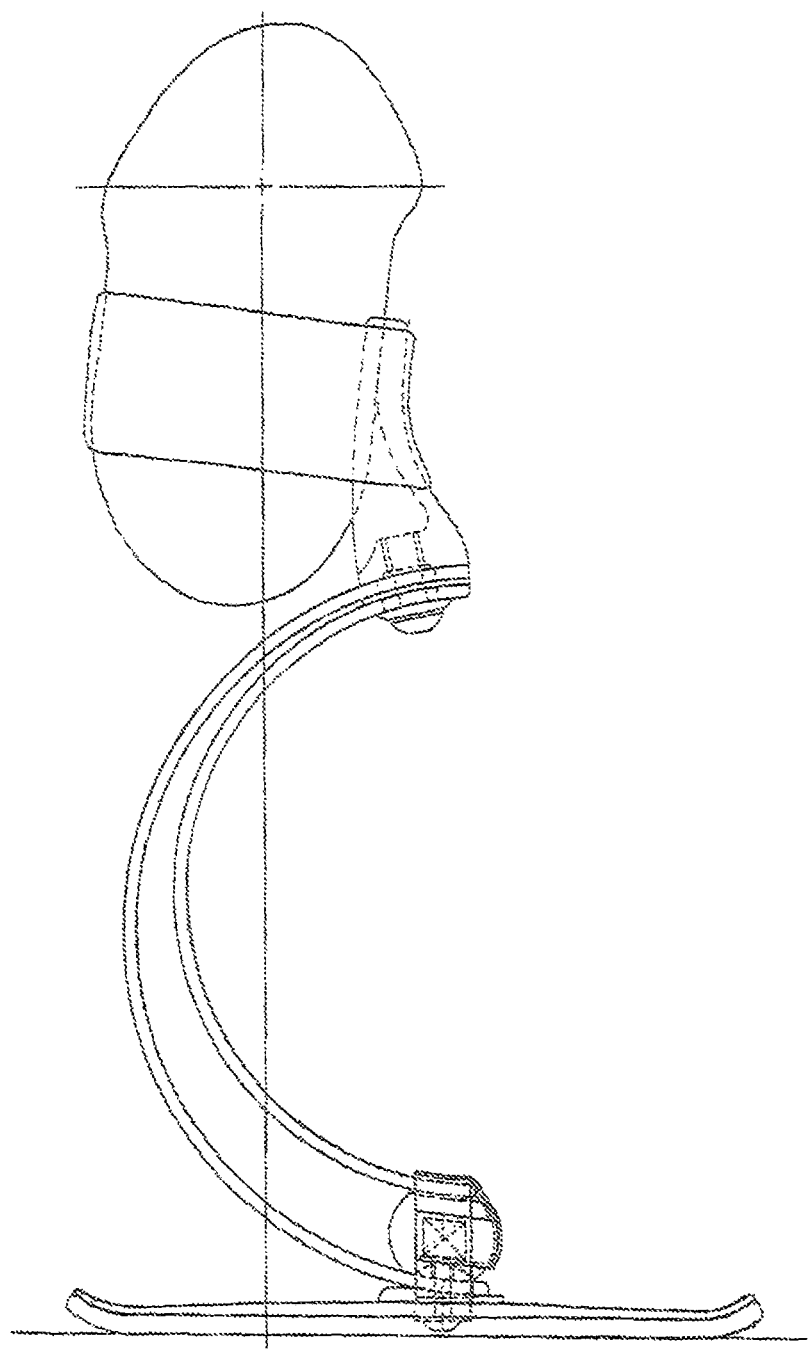
FIG. 28 illustrates a "double spring" embodiment with the more completely curved spring elements shown in FIGS. 17-25.
Figure 29:
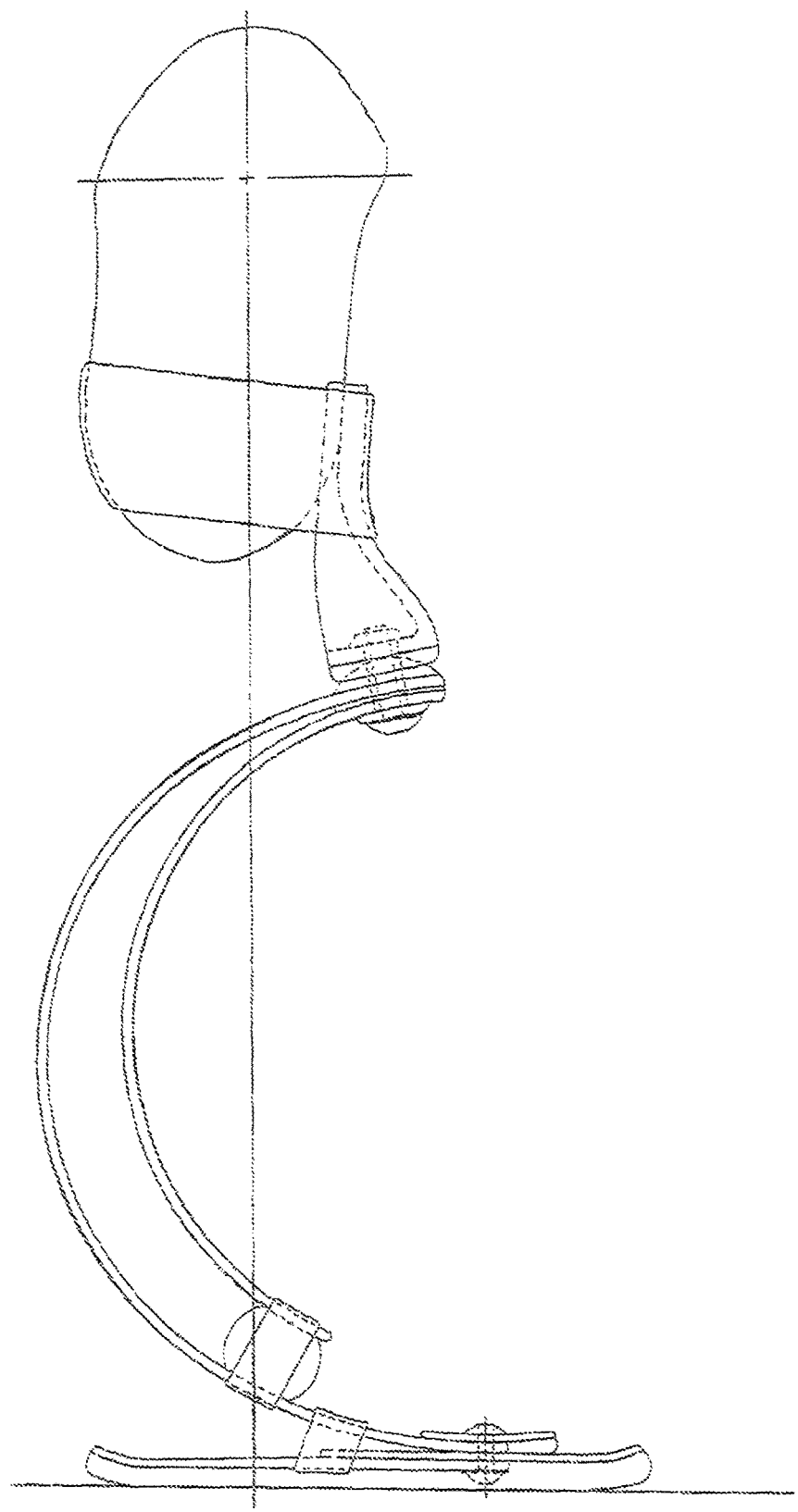
FIG. 29 shows a "land mine foot" that includes various of the foregoing elements, including the more completely circular spring elements, a footplate, various straps/restraints to limit the deformation of the prosthesis, and a cushion/bladder element to smooth the transition of energy loading and release.

FIGS. 14a and 14b are side views of a bladder element in accordance with an embodiment of the present invention. Persons of ordinary skill will understand that the side views of both single and double (and triple, etc.) bladder embodiments will be the same regardless of whether they have a single tube or more (so long as the other tubes are positioned laterally behind the "front" one that shows in the drawing). Accordingly, these drawings illustrate bladder embodiments having at least a single (or more) bladder and a single (or more) tubes.

Preferably, the compressible member(s) between the toe portion of the footplate and the front lower end of Spring 2 provide one of several ways to adjust or fine-tune the performance of the prosthesis. By way of examples: the compressible member(s) can be multiple pieces (of foam or other materials or combinations); each compressible member can have different stiffnesses/durometers; the member(s) can be manufactured or otherwise provided with a graduated or variable stiffness across the compression movement; and the members preferably are provided in modular/interchangeable forms. Multiple compressible elements in combination can provide greater flexibility for adjusting/fine-tuning the performance characteristics of the prosthesis, especially if each bladder or other element in the combination is independently adjustable.

In a preferred embodiment, one or more bladders can be filled with air, nitrogen, argon, or other suitable substance, and placed between the lower ends of the spring elements. If the bladders (or any of them) are in sealed (non-adjustable) form, the performance characteristics of the prosthesis still can be adjusted, such as by interchanging and/or relocating the bladders. Alternatively, one or more of the bladders can themselves be adjustable, so that a prosthetist or user can make the bladder harder or softer by injecting or removing substance from inside the bladder (via a valve or other suitable mechanism). For example, the bladders can be provided with adjustment tubes to adjust the resulting pressure inside the bladder, thereby fine-tuning the performance of the prosthesis (adjusting the vertical stiffness, toe load, etc.).

In certain embodiments, as the wearer moves through midstance and approaches toe off, the one or more compressible members may be exposed to frictional or similar forces between (1) the bladder(s) and (2) the respective contacting portions of Spring 2 and the footplate. Such forces can occur during walking, for example, as the forward/lower end of inner Spring 2 moves forwardly (or tries to move forwardly) with respect to that toe portion (such as may occur as the wearer moves toward toe-off). This rolling/sliding frictional force is reversed during "unloading" of the energy storing springs, footplate, and/or other elements of the prosthesis. Under these conditions, the forward/lower end of inner Spring 2 moves backwardly with respect to the footplate.

A preferred embodiment provides the compressible members in a "scuba-tank" shape, generally oriented parallel to the ground and transversely to the heel-toe axis of the foot. One or more such "tanks" can tend to roll between the other prosthetic spring elements as the wearer walks. Even if the compressible elements are in some other shape (not a tube/tank) that is relatively flat and therefore not especially susceptible to rolling, the relative movements and/or deformations of those prosthetic components can impose "sliding" frictional forces between those elements.

Although the invention can be practiced even if such rolling/sliding occurs, in preferred embodiments the rolling action is reduced or eliminated by means such as by shaping the compressible element(s) to preclude rolling, anchoring the compressible element(s) at a specific location (using glue or other means), adding tabs or other structures to block any such rolling, or any other suitable means. In a preferred embodiment, two or more such tube/tank-shaped bladders or other elements are formed integrally with each other (such as affixed to each other along one side), so that the effective overall shape of the combined/attached tanks is more "flat" and less likely to roll. Instead of or in addition to such shaping, "stops" or similar features can be provided in any suitable manner, including being formed into one or more of the various pieces (the compressible elements, the footplate portion, the underside of the lower front surface of Spring 2, and/or a combination of those) and/or glued or otherwise attached/affixed at appropriate locations. In alternative embodiments, the rolling forces on the compressible members can be reduced or even eliminated by lubricating those interfaces to facilitate slippage between those contacting surfaces. Other approaches to reduce/eliminate that friction include forming and/or coating the contacting surfaces with one or more very low-friction materials.

As indicated above, a preferred embodiment also includes a loop or strap element around (a) the compressible members such as "scuba tanks" or foam, and (b) the lower front end of Spring 2 and the footplate portion that underlies the compressible members. Among other things, such a connection enables Spring 2 to help limit the plantar flexion of the footplate's toe portion.

Thus, some preferred embodiments of the invention provide effective "contact" and energy/movement transmission between the front/lower ends of Springs 1 and/or 2, through an intermediary zone/apparatus (such as compressible bladders, foam, and/or other elements). In addition to pre-loading Spring 2, this intermediary zone/apparatus can provide other desirable functionality. For example, the effective connection through that intermediary zone/apparatus can provide some resistance to (and/or limit or even preclude) sideways movement (to the patient's left or right) of the lower end of Spring 2 with respect to Spring 1 and/or the footplate.

Figure 11A:
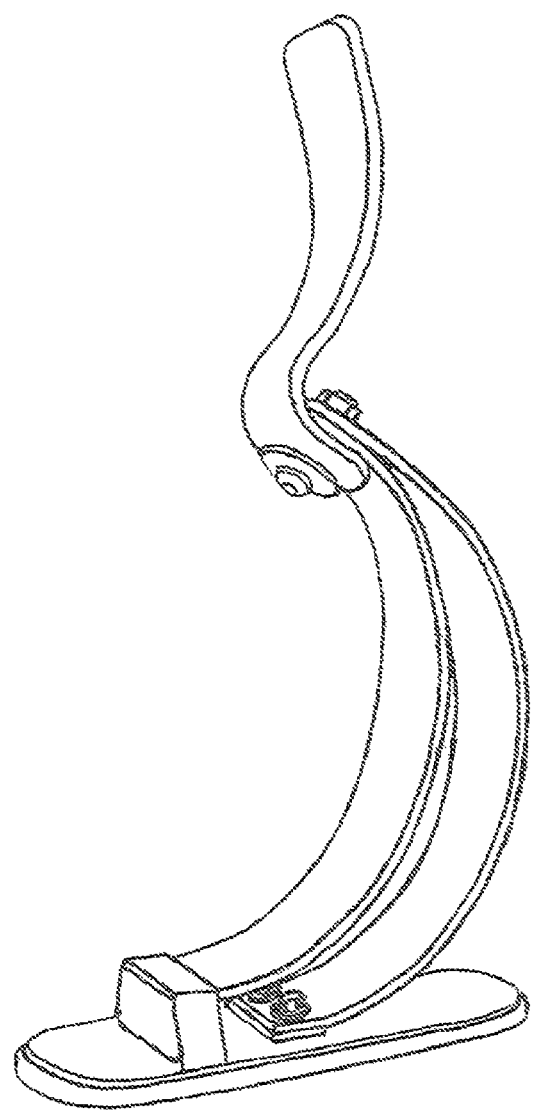
FIGS. 11a, 11b, 11c, and 11d are front, rear and side perspective views of an overall prosthetic assembly in accordance with the present invention, including a prosthetic device having two elongated curved energy-storing/releasing members.
Figure 11B:
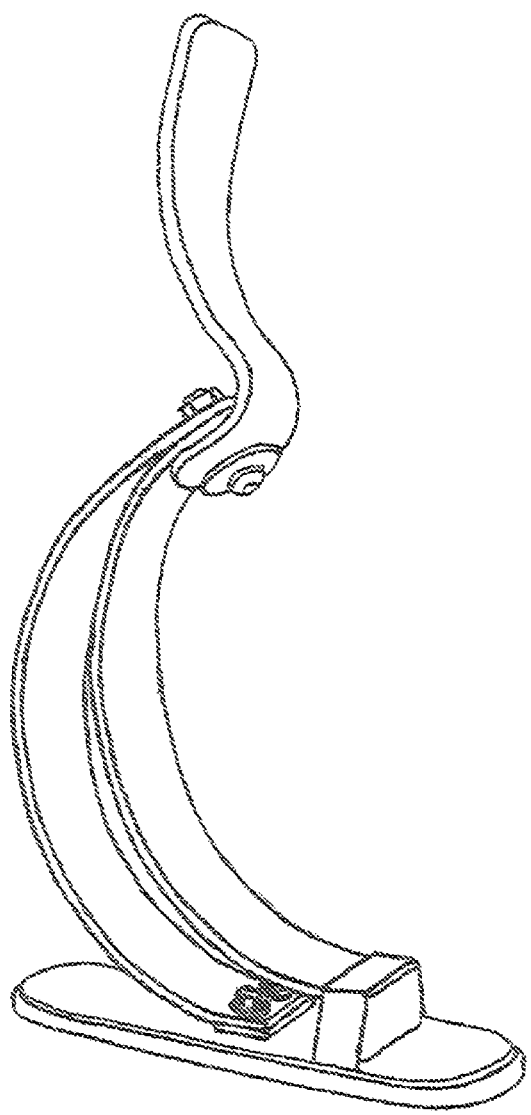
Figure 11C:
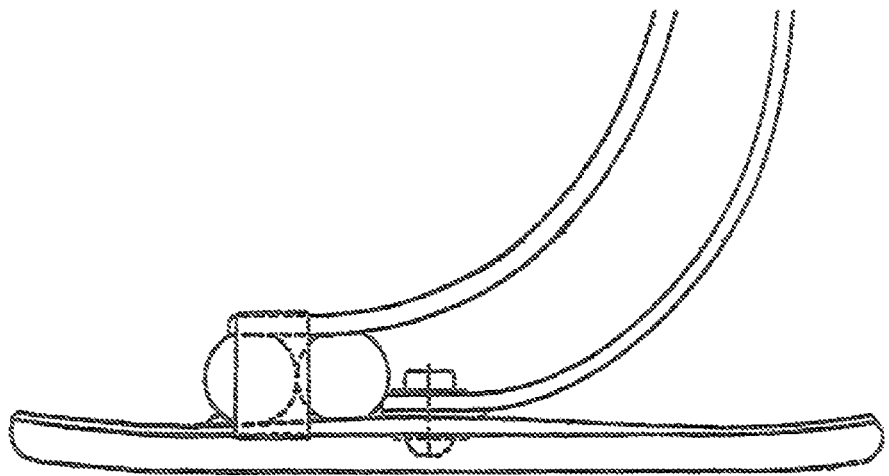
Figure 11D:
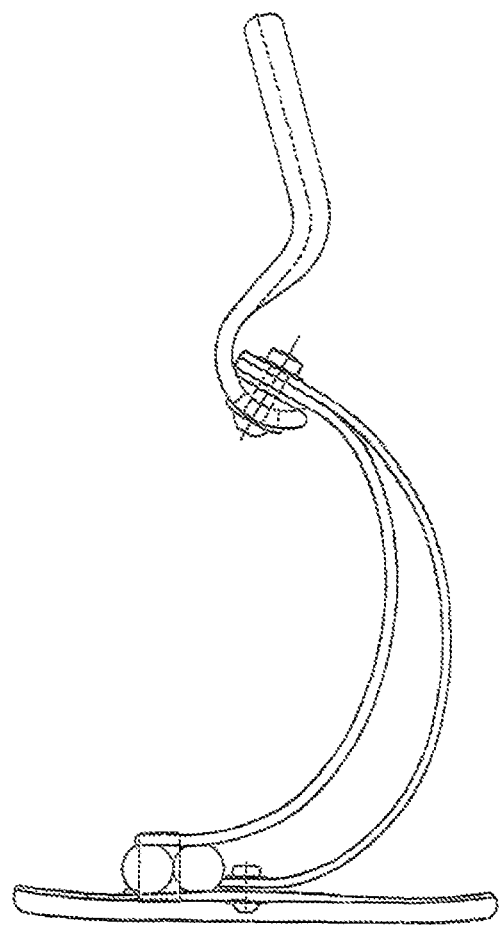
Figure 11E:
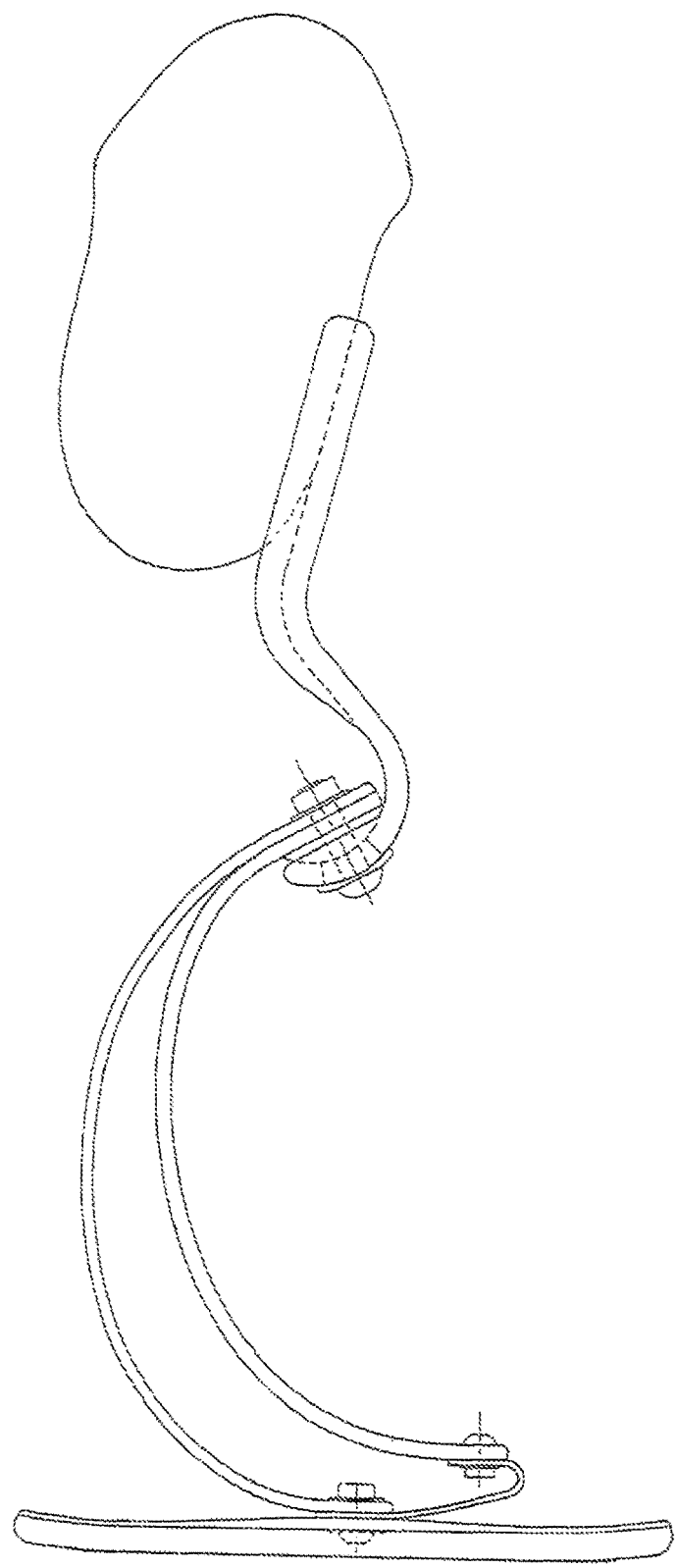
FIG. 11e is an elevation view of an overall prosthetic assembly in accordance with the present invention, including a prosthetic device having two elongated curved energy-storing/releasing members operably connected to a prosthetic socket, and having a "diving board" connector/spring element.
Figure 11F:
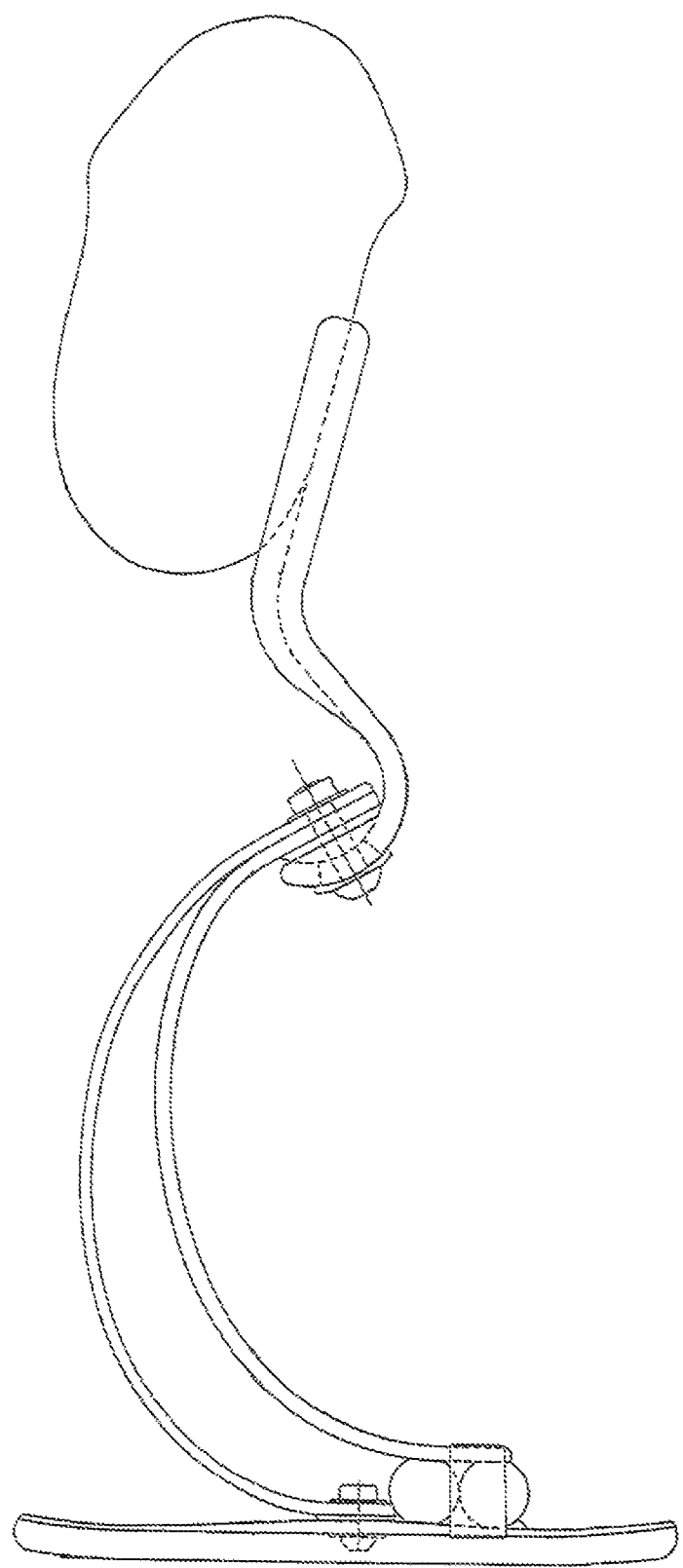
FIG. 11f is an elevation view of an overall prosthetic assembly in accordance with the present invention, including a prosthetic device having two elongated curved energy-storing/releasing members operably connected to a prosthetic socket, and having a double bladder compressible element and strap.
Figure 12A:
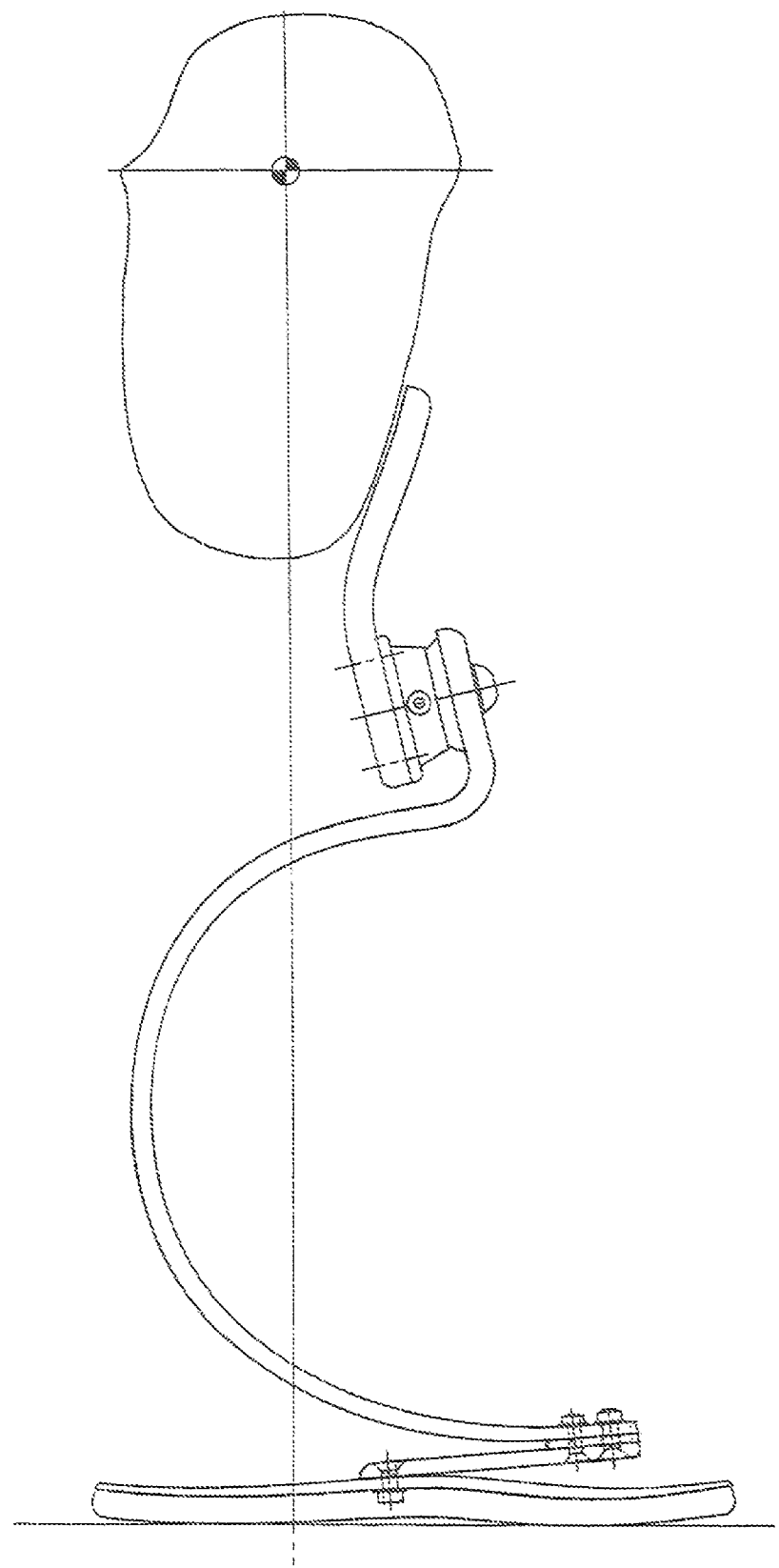
FIG. 12a is an elevation view of an overall prosthetic assembly in accordance with another embodiment of the present invention, including a prosthetic device having a single elongated curved energy-storing/releasing member, an alternate upper connector element, and an alternate lower connection portion.
Figure 12B:
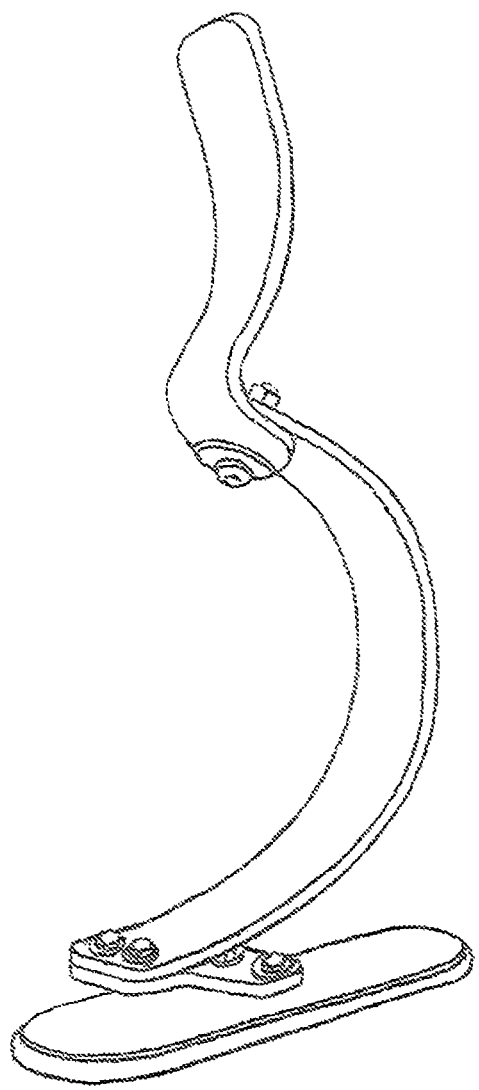
FIGS. 12b, 12c, 12d, 12e, 12f, 12g, 12h, 12i, and 12j are perspective views of another embodiment of the present invention having a single elongated curved energy-storing/releasing member and a Z-bar extension portion.
Figure 12C:
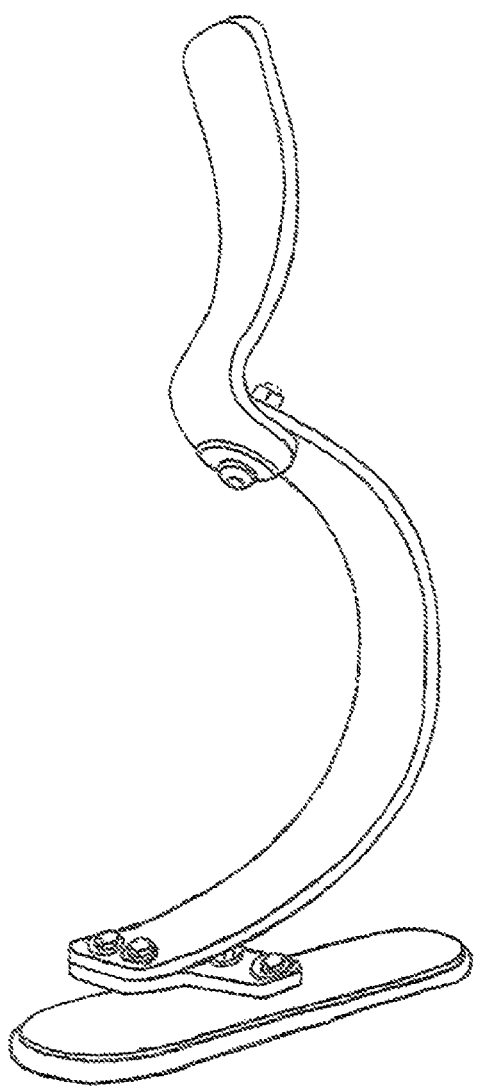
Figure 12D:
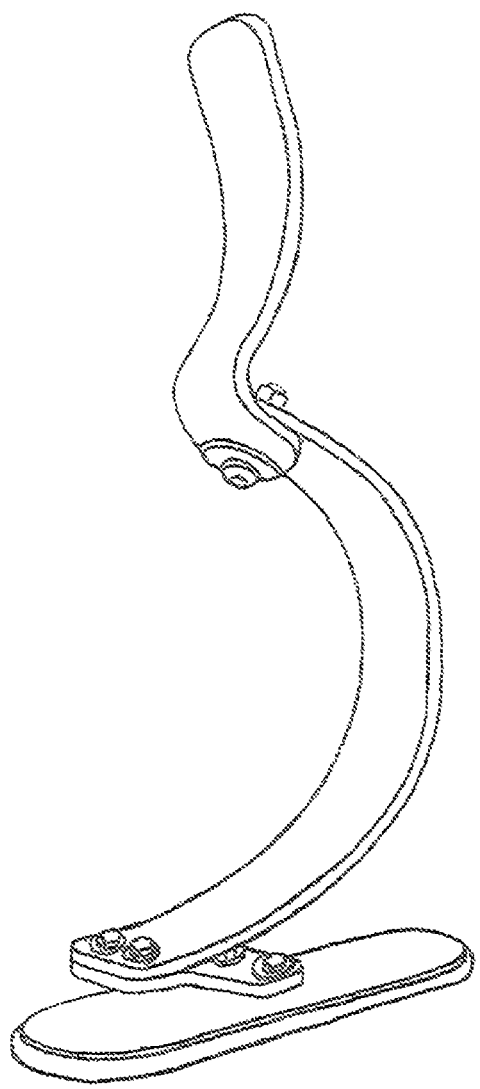
Figure 12E:
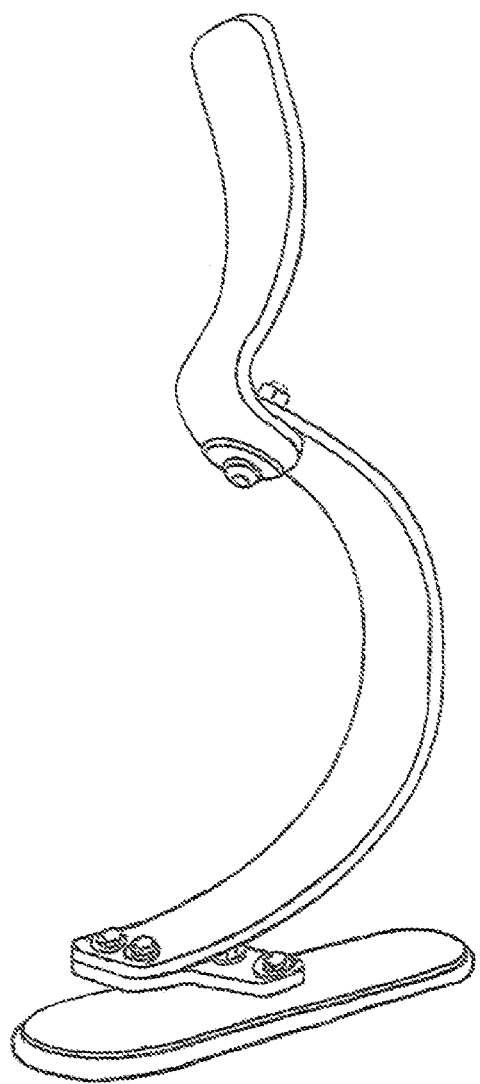
Figure 12F:
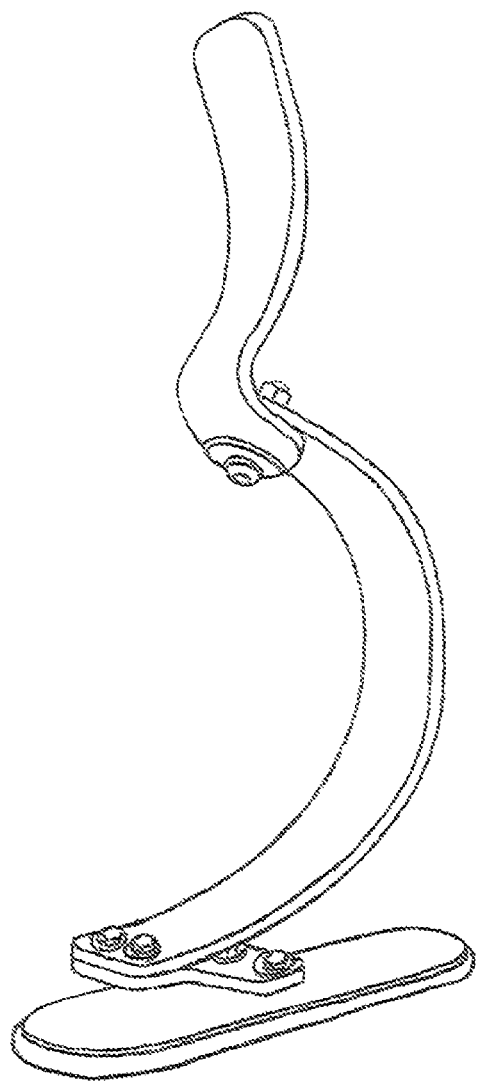
Figure 12G:
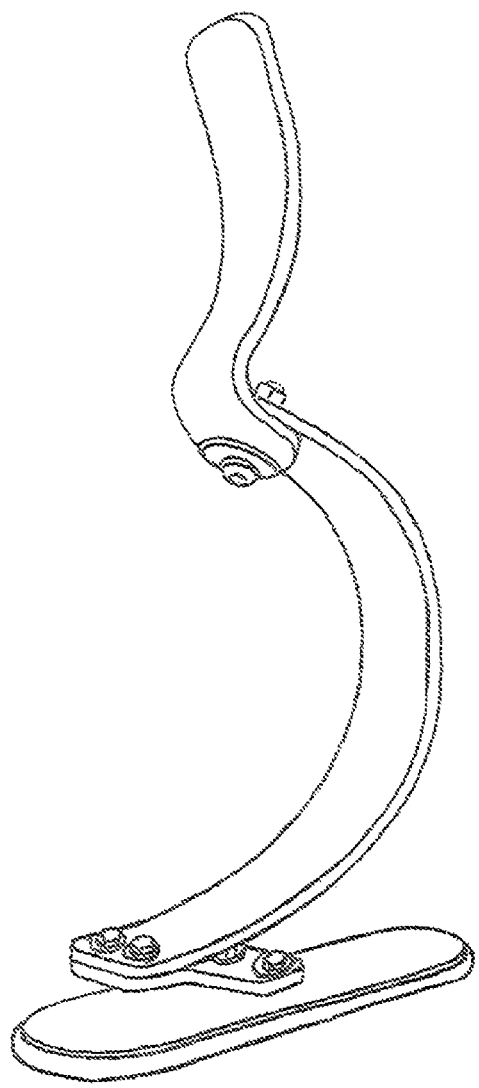
Figure 12H:
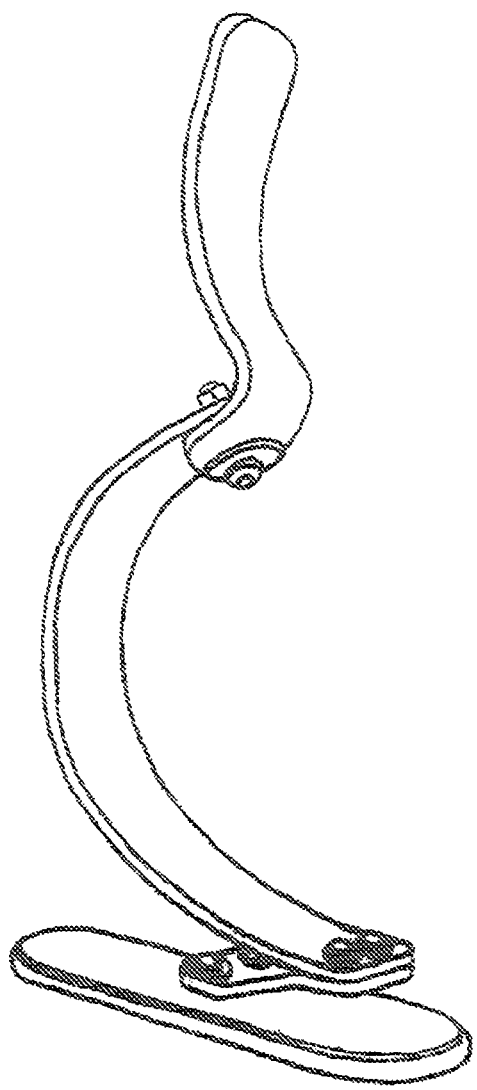
Figure 12I:
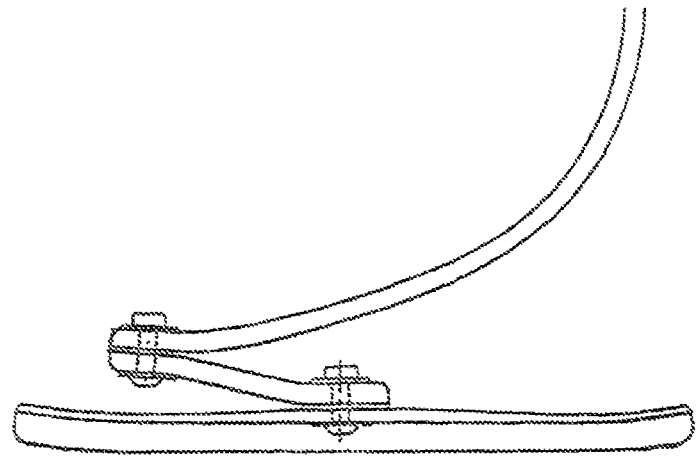
Figure 12J:
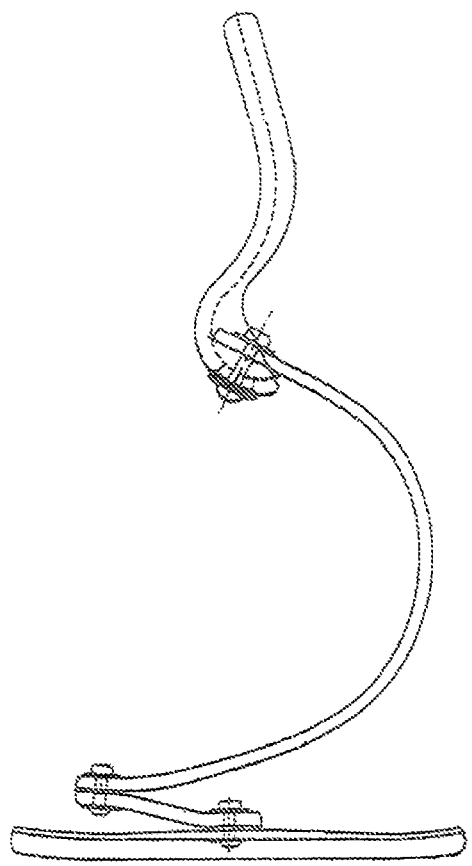
Figure 13A:
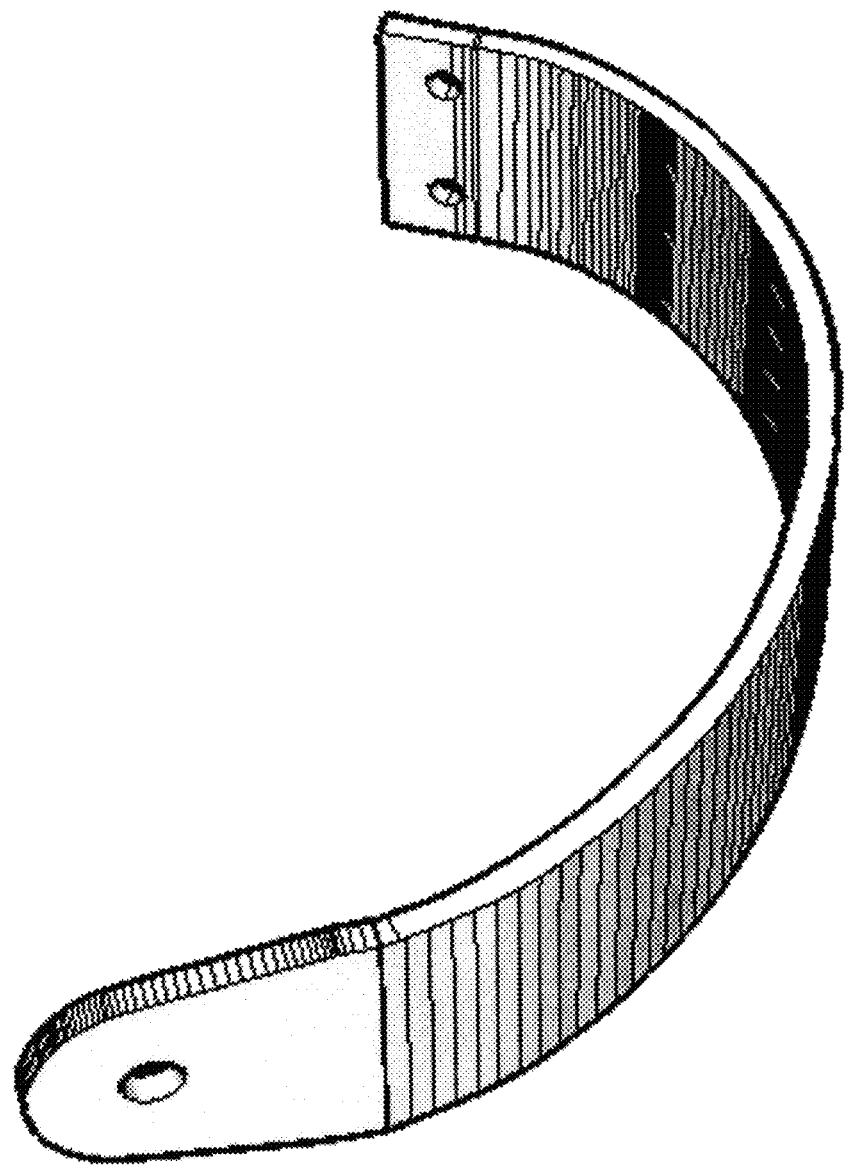
FIGS. 13a, 13b, and 13c are perspective views of a C-spring in accordance with a preferred embodiment of the present invention.
Figure 13B:
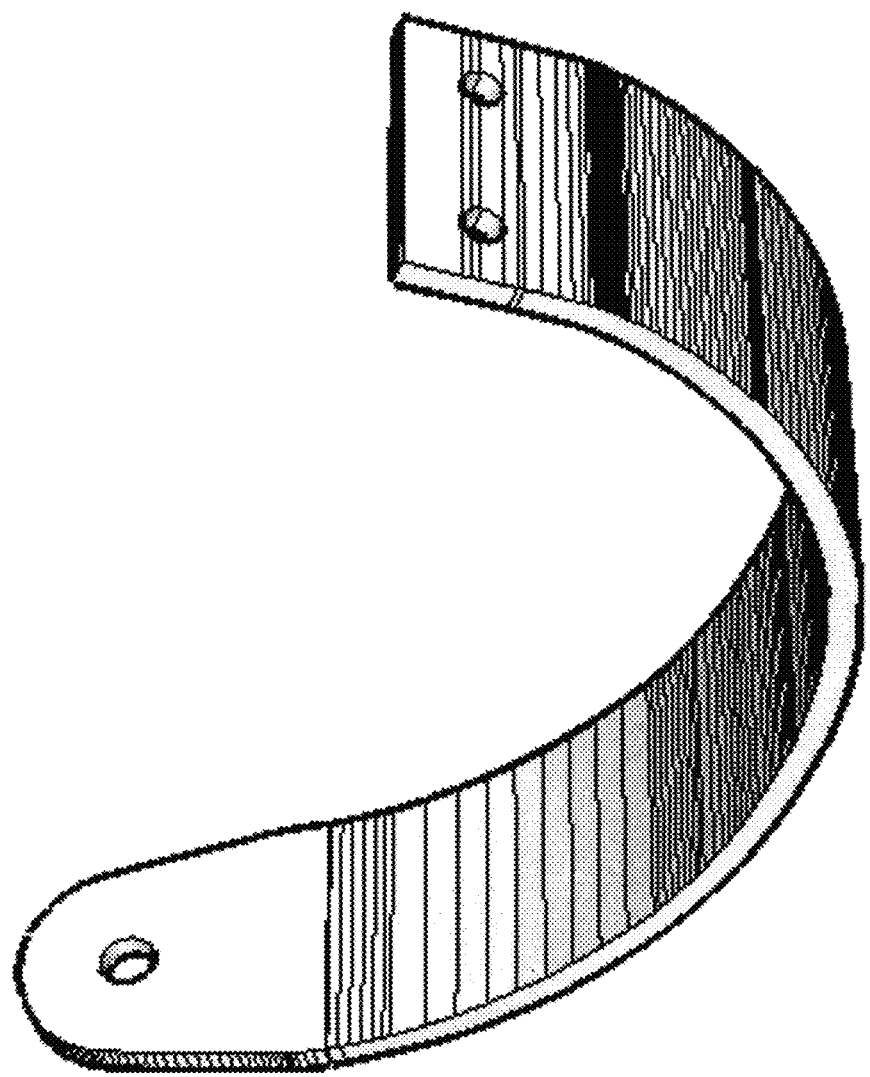
Figure 13C:
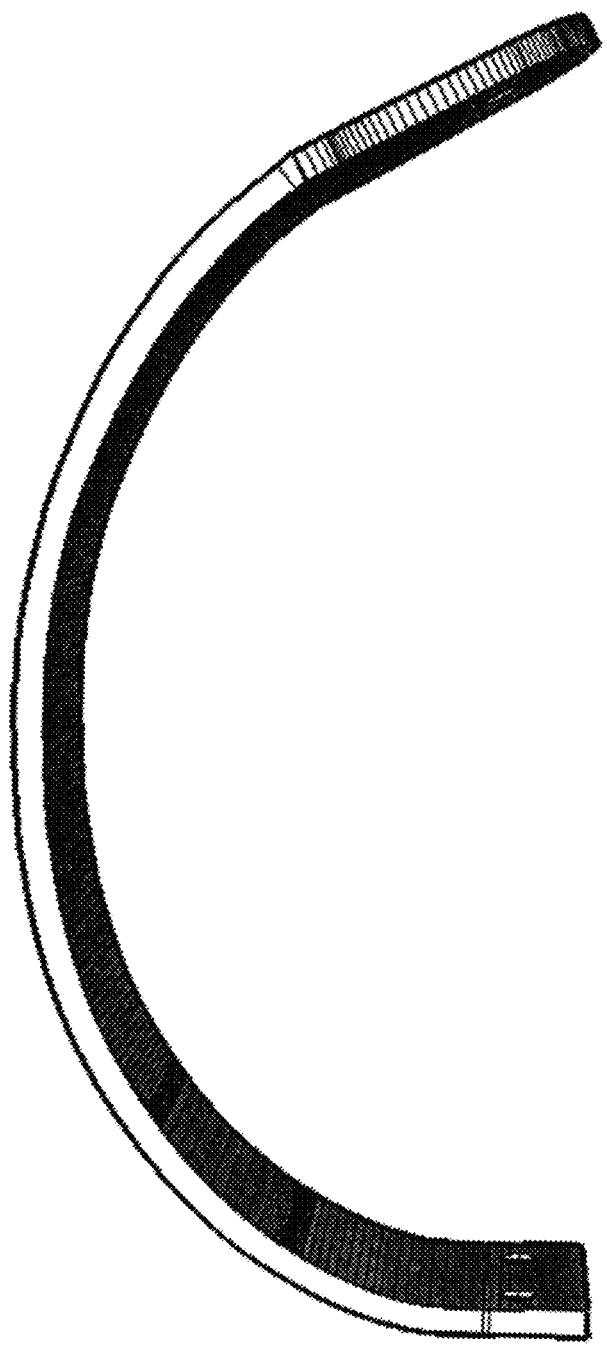

Among the many alternative compressible members that can be used in practicing the invention, and as illustrated in FIG. 11e, the foam/bladder/other elements can be replaced by (or used with) a "diving board" connector/spring element which is positioned between the toe portion of the footplate and the lower/front surface of Spring 2. In passing, the reader will note that the terminology and concept of a "diving board" is also used below in describing certain Single C-Spring embodiments of the invention. Persons of ordinary skill in the art will understand that use of that term ("diving board") in connection with those Single C-Spring embodiments is similar but not necessarily identical to the way the term is used here to describe this type of connector/spring element in this Double C-Spring embodiment.

As with the other preferred structural elements in this Double C-Spring embodiment, this "diving board" connector also preferably is fabricated as an energy storing and returning element. Preferably, the "diving board" connector element is relatively stiff. Functionally, the "diving board" is similar to embodiments using foam/bladder/other elements, in that it communicates forces (plantar flexion and/or compression, etc.) between the footplate and the front lower end of Spring 2, helps prevent excessive plantar flexion of the toe portion of the footplate, and generally supports and smoothes the action of toe loading conditions. Preferably, the amount of stiffness or energy stored/released is proportional to the amount of deformation of the "diving board" element, and at midstance, the preferred "preload" on Spring 2 forces the diving board to bend slightly from its resting position toward the footplate.

However, as compared to compressible bladders or foam elements, the diving board preferably can be a simpler and longer-lasting approach. It can be easier to manufacture and assemble, and have fewer parts, and be much less susceptible to wearing out. The diving board does not require the external wrapping or similar preparation that may be useful for any compressible foam elements, it has no bladders that can leaks or otherwise lose pressure, and it does not require any strap element (which, among other things, may break or come loose).

A diving board type of connector/compressible element can be provided in a wide range of sizes and shapes, can be fabricated from a wide range of suitable materials, and can be operably connected to the other elements of the prosthesis in a wide variety of ways. A preferred embodiment is fabricated from graphite that preferably can last for the life of the prosthesis (without wearing out or breaking). The diving board can be at least partially filament wound or can be fully hand laid up. It also preferably has relatively constant thickness, is very thin and lightweight, and has material memory characteristics that provide at least some additional "spring" action/energy storage/release to the assembly. As compared to a strap for limiting the maximum distance between the footplate toe portion and the lower forward end of Spring 2, a diving board type of element can allow some gradual "flex" up to and beyond the "absolute" limit that might be imposed by a strap. Preferably, from whatever "spread" relationship that is imposed on those two parts (the footplate toe portion and the lower forward end of Spring 2), the diving board's energy storing characteristics then urge the toe plate and the lower end of Spring 2 back toward each other (and toward their respective resting/non-loaded positions).

More generally, this preferred intermediary zone/apparatus (bladders/foam/diving board/other) preferably enhances the smooth transition of loading/unloading forces during use of the prosthesis. The zone preferably provides a very smooth "handoff" of the energy loading on the prosthesis, such as a smooth transmission from heel strike (which primarily loads Spring 1 in vertical compression with Spring 2 preferably expanding as it limits plantar-flexion, as discussed above) to the loading involved in midstance, and from there to the toe loading/toe off condition (discussed below).

Alone and/or in combination, these elements and the resulting prosthetic assembly preferably help ensure that the patient feels little, if any, sudden change during the course of the complete stride cadence. Preferably, the load of the wearer's weight and other forces smoothly transfers from and among Spring 1, Spring 2, and any other components of the prosthesis. Preferably, as each of those members start to be compressed and/or expanded, they ramp up or increase in stiffness (resistance to further compression/expansion). Although initial deformation of at least certain of the energy/storing spring members preferably is relatively soft and easy (for example, Spring 1), increasing deformation results in increasing stiffness. Preferably, the prosthesis allows some smooth and gradual vertical compression as the patient moves from heel strike to mid-stance and then to toe-off (the amount and rate of that compression will depend on a number of factors, such as the speed and vigor with which the patient is walking, etc.). In preferred embodiments, the various spring members (e.g., Spring 1, 2, and/or 3 et al., the diving board, the footplate, etc.) gradually and increasingly slow that compression and the other dynamic motions of the assembly. Depending on the embodiment and the patient's use of the prosthesis, the spring elements may eventually reach a point at which they do not compress or expand any further (they are "fully" compressed or expanded). Preferably, even the foam/air/bladder/other compressible element(s) between the lower front ends of the springs exhibit this same characteristic of "ramping up" in stiffness as those elements are increasingly compressed.

Toe-Off

Toe-off can be described as the part of the stride cadence at which the toe portion of the footplate is the primary or only portion of the prosthesis that contacts the ground.

Among other situations, toe-off occurs as the patient walks forward from mid-stance onto the "ball" area of the foot and eventually raises the foot prosthesis completely off the ground. During this movement towards and through toe-off, the prosthesis preferably provides increasing resistance to dorsiflexion (movement of the toe portion of the footplate toward the natural leg's shin area). As such dorsiflexion increases, the foam/air/bladder/diving board/other compressible element preferably approaches and even reaches a "maximum" compression, and the toe load increasingly is transferred (through that fully-compressed bladder/etc. intermediary zone/apparatus) from the toe area of the footplate to Spring 2.

In conditions in which the compressible element(s) and the toe area of the footplate cannot further bend upwardly toward Spring 2 and/or compress, any further toe loading preferably will result in direct compression of Spring 2, and thus Spring 2 will thereafter provide increasing resistance to increasing dorsiflexion. Preferably, Spring 2 takes most of the toe load as the wearer moves through this toe-off position.

As the wearer approaches and reaches toe-off, the loading of Springs 1 and 2 preferably is reversed from the heel strike condition described above. All or most of the vertical load is imposed on Spring 2, compressing it into a tighter arc, while the footplate tends to pivot around that front connection point, lowering the heel portion of the footplate and thereby pulling Spring 1 toward a relatively more open position. To the extent that Spring 1 is "opened" beyond its normal resting position, the energy stored in Spring 1 (by the patient having forced it "open" during his/her stride) preferably is available to pull the heel portion back toward its resting position once the prosthetic assembly is lifted from the ground (or at least the toe loading is reduced/removed).

As previously indicated, the invention can also be practiced in a wide variety of "multiple C Spring embodiments", including those having more than two C-spring elements. Among many other embodiments, a third (and/or a fourth, etc.) spring can be nested in a pattern similar to the way that Spring 2 is nested within Spring 1. The front end(s) of such springs can be positioned and operably "connected" to the footplate and/or each other (such as via compressible members, diving boards, or other means), and the particular bending and energy-storing/release characteristics can be customized to provide alternative (and even smoother) energy transitions for the prosthesis and for the patient's comfort and experience when walking/etc.

Even for 2 C-Spring embodiments, the invention permits a wide variety of approaches from which prosthetists and patients can select. For example, in certain applications, it may be useful for the two or more C-springs to have similar or even identical bending characteristics. Rather than Spring 1 being significantly "softer" and more easily compressible than Spring 2, those springs can each have a springiness near or at the average springiness of the soft Spring 1 and stiff Spring 2 embodiments. Persons of ordinary skill in the art will understand that such alternative embodiments may result in various design and performance compromises, such as the resulting patient experience during walking or other movement on the prosthesis, the weight and/or complexity of the prosthesis, etc.

Single C (Only Spring 1)

Although there are many similarities between the foregoing preferred Double C spring (two or more springs) description and preferred embodiments using only a single C spring, there are differences. For example, for the same patient changing from a Double C spring embodiment to a Single C spring embodiment (and for the same expected activity level and loads), the relatively softer C spring (Spring 1 of the 2-C embodiment discussed above) could not be used effectively by itself. In other words, a preferred Spring 1 in the 2-C embodiment would be too soft to function well without the relatively stiffer Spring 2 acting as its backup. Among other things, that "softer" Spring 1 would not provide sufficient vertical support to the patient, and would not permit the patient to control the prosthetic footplate satisfactorily.

Instead, for embodiments of the invention that use a single C-spring (rather than the double C or more embodiments discussed above) between the patient's socket and the footplate, to function well that single spring must be stiffer than the preferred soft Spring 1 described above for the double C embodiments.

Prior to the invention, a prosthesis with a single energy-storing/releasing member connecting the patient's socket to the middle of a heel-to-toe footplate was less than satisfactory. Among other things, the single energy-storing/releasing member had to be stiff enough to limit both plantar flexion and dorsiflexion of the footplate's toe and heel portions. As a consequence of being so stiff, the single energy-storing/releasing member typically could not provide much, if any, desirable vertical spring compliance action (energy storing/release such as occurs in the C-shaped springs of the invention). Said another way, such prostheses could not provide to the patient any significant amount of vertical "spring" without reducing the patient's ability to sufficiently control plantar flexion and/or dorsiflexion of the footplate portions. Thus, using the comparison above, if a prosthetist took a patient's relatively "soft" Spring 1 (from a two-spring design such as described above, that was satisfactory to a given patient) and assembled it into a single C lower-leg prosthesis for that same patient, the prosthesis would provide substantial vertical "spring" action to the wearer but would not be sufficiently stiff to provide satisfactory performance regarding plantar flexion and/or dorsiflexion, or other footplate and/or toe load performance/characteristics.

In contrast, and as described herein, single C-spring embodiments of the invention preferably emulate a normal foot's heel strike, mid-stance, and toe-off, preferably by combining some or all of the following features:

1. a footplate element 15 that approximates the shape and size of the patient's normal sole, with a toe portion 20 and a heel portion 25 having material memory (to return to its original shape) or otherwise capable of spring action energy storage and release. The footplate can even be a relatively conventional prior art modular footplate, and it preferably is fabricated/configured to have bending/spring characteristics that complement those of the other components or portions of the prosthesis.
2. a single generally C-shaped spring element 70 or portion positioned between the patient's socket and the footplate element.
3. an extension portion extending upwardly and forwardly from (a) the approximate middle of the top surface of the footplate to (b) the forwardmost lower portion of the C-shaped spring portion. Among its many embodiments, the extension portion can be integrally formed with the C-shaped spring portion (such as the "sweptback" 80 example discussed herein), a separate modular element (such as the "Z-bar" 75 example discussed herein), or some other suitable structure and configuration. Preferably, the extension portion also is capable of spring action energy storage and release.
4. The elements between the footplate and the patient's socket (such as the C-shaped spring portion and the extension portion) preferably are sufficiently stiff to allow the patient to desirably control of the footplate and its dorsiflexion and plantar flexion. However, the extension portion moves the effective pivot point (of the forward lower end of the C-shaped spring portion) forward toward the toe area, which (among other benefits) gives the patient a much longer effective lever arm for actuating the C-shaped spring portion and the heel portion of the assembly, and also positions that forward pivot point so that it can act as a "backstop" for any upward bending of the toe portion of the footplate (thus enabling embodiments to use thinner and/or lighter toe portions than would otherwise be possible). The mechanical advantages of this relative positioning of the forward pivot point allows the energy storing/releasing characteristics of the various elements to substantially mimic the performance of a natural foot and substantially improve the patient's experience.

To help provide both the desired vertical spring action/compliance and the desired control over and sensations from toe and heel loading and movements, preferred single spring member embodiments of the invention preferably have a pivot axis for vertical loading that is (a) at or near the bottom forward portion of that single C-spring shape, and (b) forward of the middle of the footplate, toward the toe portion of the footplate (in fact, the further forward that pivot point is located over the toe portion, the more vertical spring action is available to the patient).

As described below, that forwardly positioned pivot axis is held relatively stiffly in its position with respect to the footplate (to provide the desired control of the footplate). In fact, the entire length of the single C-shaped element preferably is substantially stiff (certainly stiffer than the preferred Spring 1 discussed above), but as further explained below, the forward positioning of that Single Spring's main pivot axis provides sufficient leverage to the patient so that it is much easier to deform/compress the preferred "single C" shape. Consequently, although the single C-spring preferably is substantially stiff along its length, the assembled prosthesis feels to the patient as if it is substantially "soft," in that it provides to the patient a desirable amount of vertical spring action/compliance. Thus, while the preferred C-shaped spring portion and the extension portion are stiff enough to provide desired control to the patient, the leverage provided by moving forward the pivot point allows the patient to comfortably actuate and experience vertical compression of the assembly. That vertical compression would not otherwise be available if the lower end of the "stiff" C-shaped spring portion were connected to the footplate at or near its middle, because the patient's weight would not be sufficient to overcome that stiffness satisfactorily.

Among its many other benefits, the present invention solves this problem, and enables a lower leg prosthesis with only a single main spring member to store/release vertical loading energy to have both (a) satisfactory control over plantar flexion and/or dorsiflexion and (b) satisfactory vertical spring action. Although the single energy-storing/releasing spring member preferably is fabricated in a manner similar to that discussed above and otherwise has characteristics similar to at least some of the spring members discussed above, it may be any of a wide range of different elements, including certain prior art spring components and/or devices.

A convenient analogy can be drawn between certain preferred performance characteristics of various embodiments of the invention and a swimming pool diving board (as noted above, the use of this term "diving board" to describe certain preferred aspects of various Single C-Spring embodiments is similar but not necessarily identical to the connector element discussion above regarding Double C-Spring embodiments).

In many swimming pool diving boards, the "springiness" of the board can be adjusted, such as by horizontally repositioning a bar under the board within a range of positions from nearer the "pool end" of the board to nearer to the "steps end" of the board. The bar functions as a pivot point for the board. If that pivot point is moved closer to the "pool end" of the board, it shortens the "bendable" portion of the diving board, making the board feel stiffer. If that bar/pivot point instead is moved closer to the "steps end" of the board, it lengthens the "bendable" portion of the diving board, and makes it easier for the diver to bend the board, at least in part because the diver's weight is applied at the end of a longer effective lever arm. In other words, for the same diver, having the same weight, and jumping on the same location at the end of the board with the same force, the amount of board deflection and the "smoothness" during its bending can vary simply by moving that bar/pivot point.

Analogously to such swimming pool diving boards, in certain embodiments of the invention the "springiness" experienced by the patient (again, for the same patient weight, the same loading conditions, etc.) can be modified by moving its pivot point further toward or away from the toe of the prosthesis. In the embodiments described here, moving that point further toward the toe increases the effective length and the springiness of the prosthesis' "diving board," and moving it further away from the toe reduces that springiness. Like the increased "springy softness" of the diving board when it is set to give the swimmer/diver a longer lever arm, the preferred relatively longer effective length of the patient's lever arm (for actuating the main spring body of the C member) provides a desirable increase in the "springy softness" of the prosthesis, as experienced by the patient during vertical loading and other situations. Depending on the patient, the patient's expected activity level, and other factors, an embodiment of the invention can be designed, selected, and/or assembled that provides the performance characteristics desired by that patient.

Figure 5A:
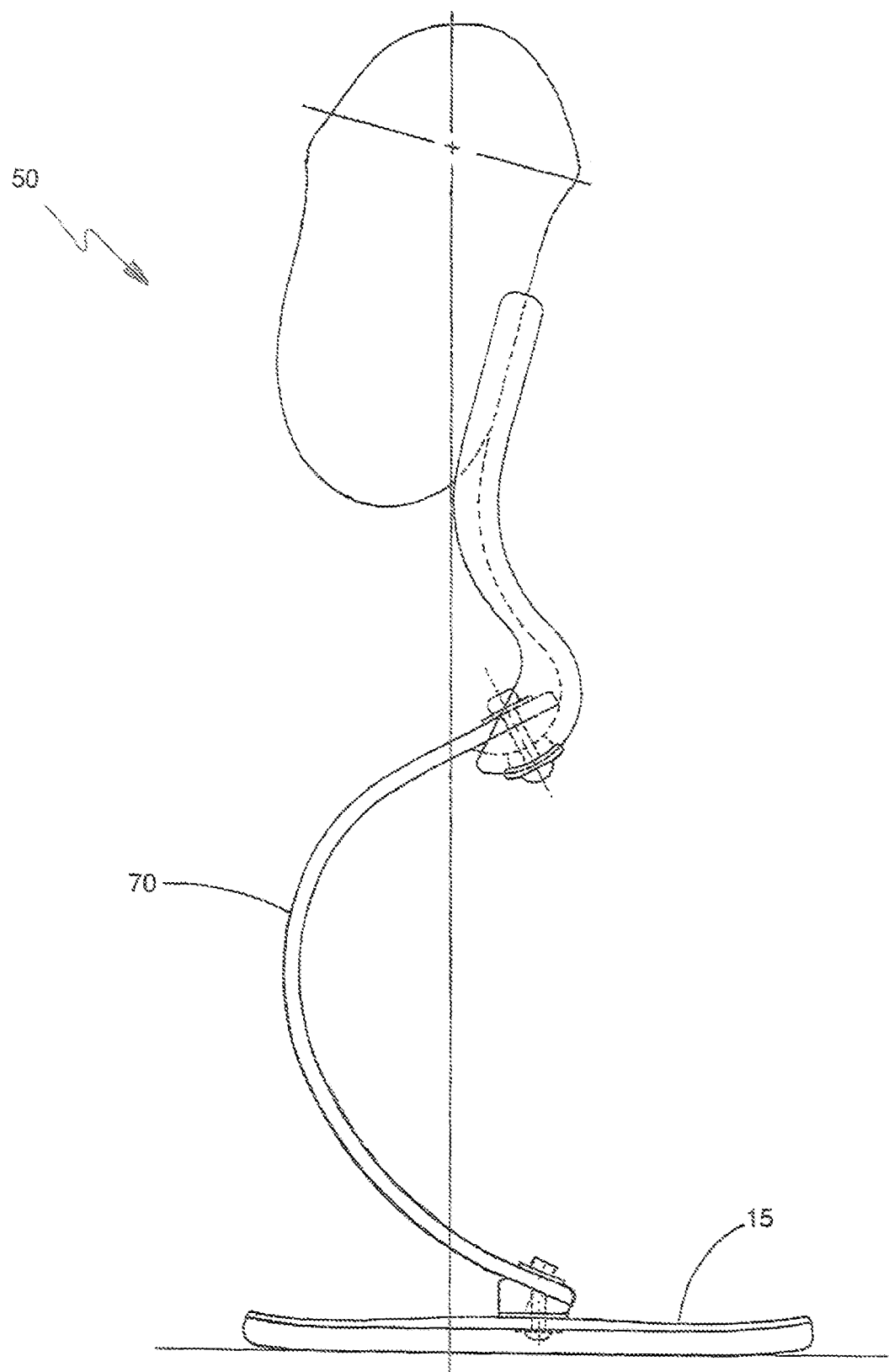
FIG. 5a is an elevation view of another alternative embodiment of the present invention having a single elongated curved energy-storing/releasing member operably attached to the footplate in order to move the pivot point forward towards the toe portion of the footplate.
Figure 5B:
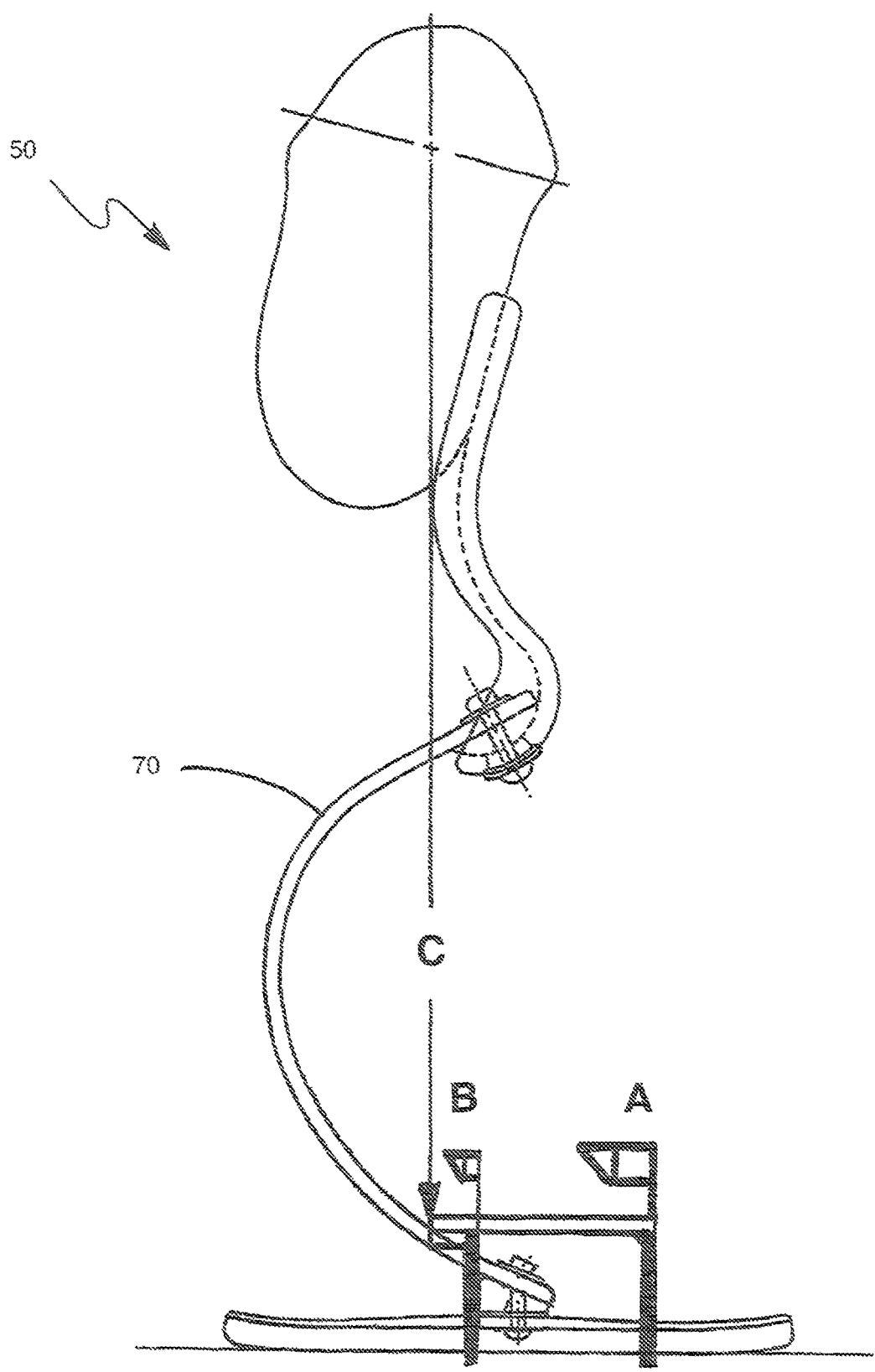
FIGS. 5b and 5c are elevation views of another embodiment of the present invention.
Figure 5C:
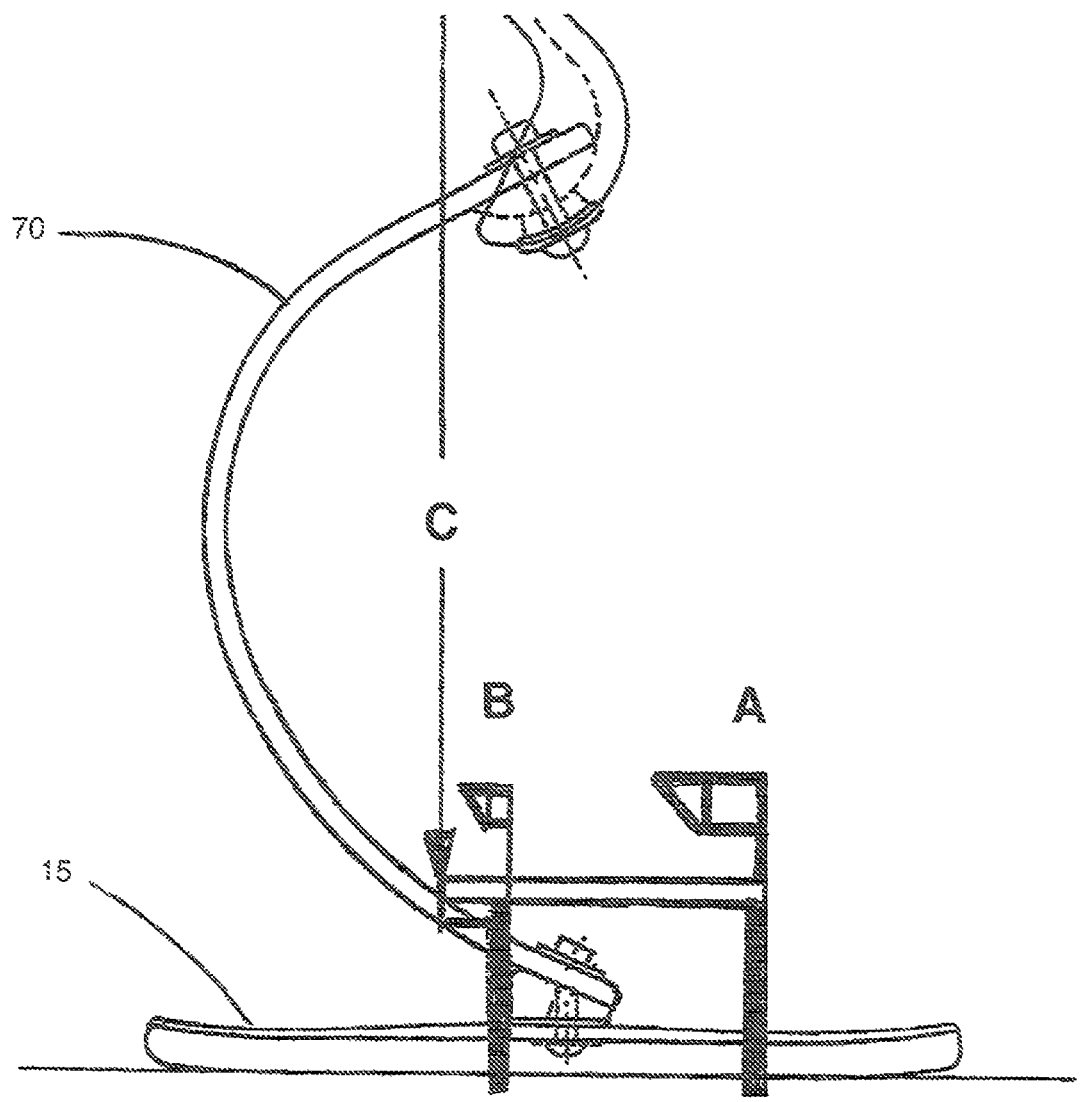
Figure 6A:
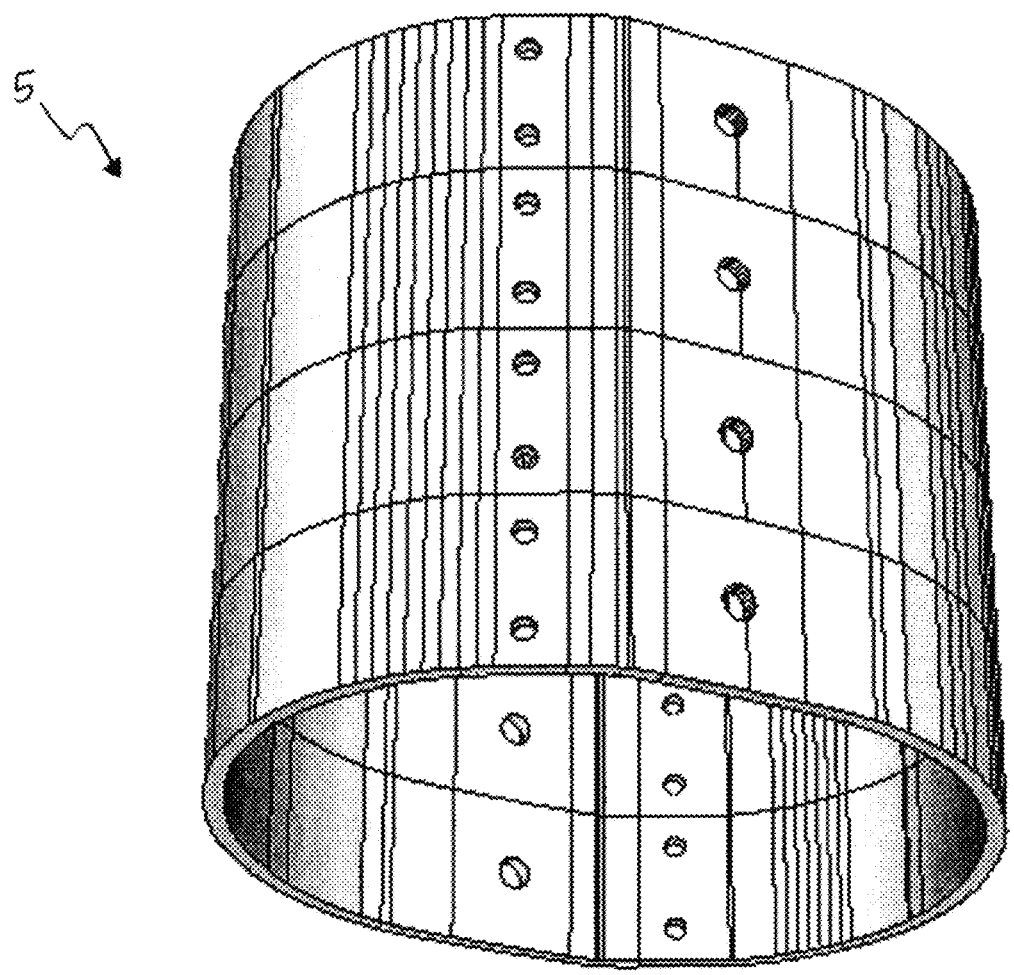
FIG. 6a is an isometric view of a stack of multiple energy storing and releasing elements fabricated by a filament winding process.
Figure 6B:
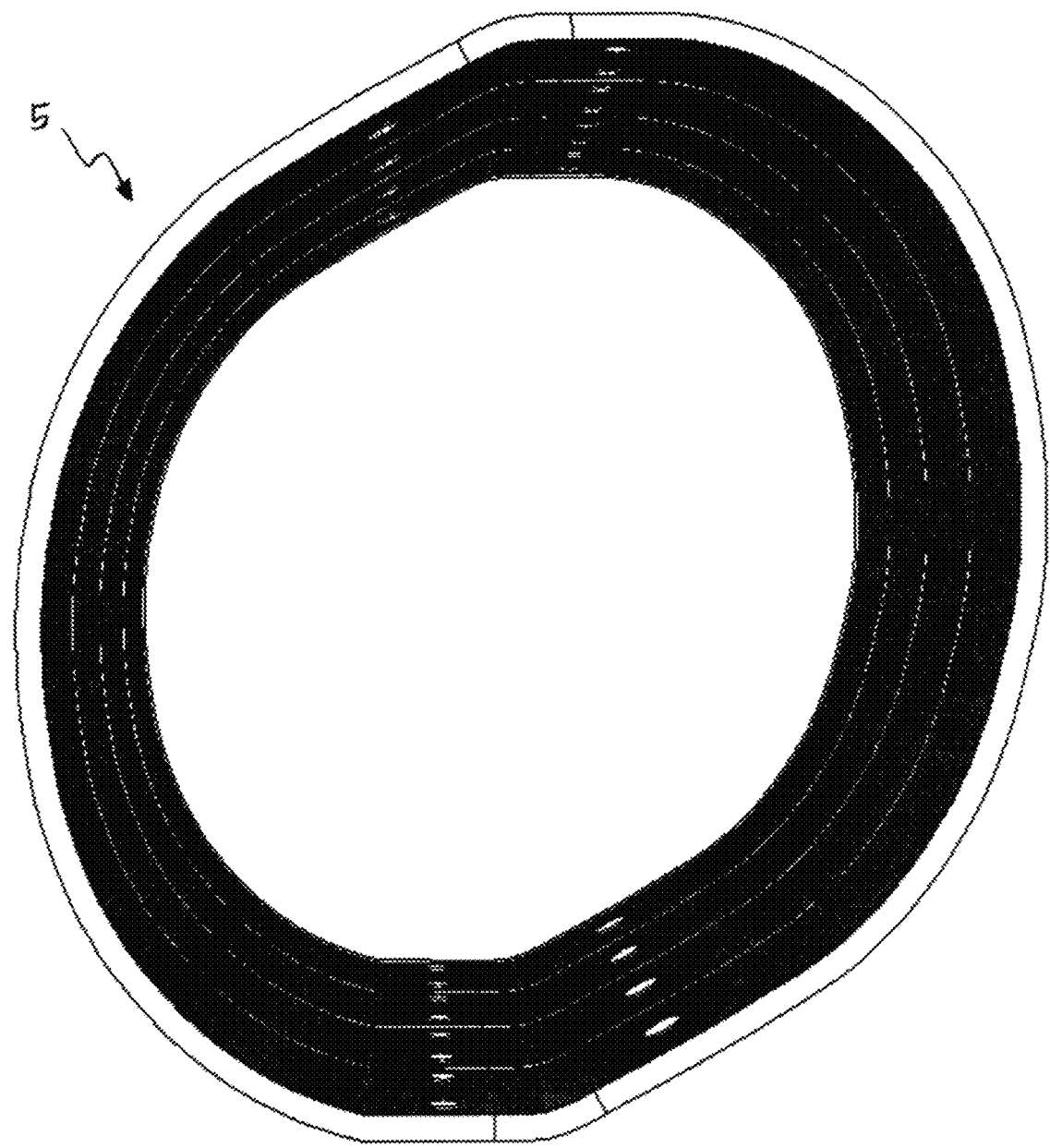
Figure 6C:
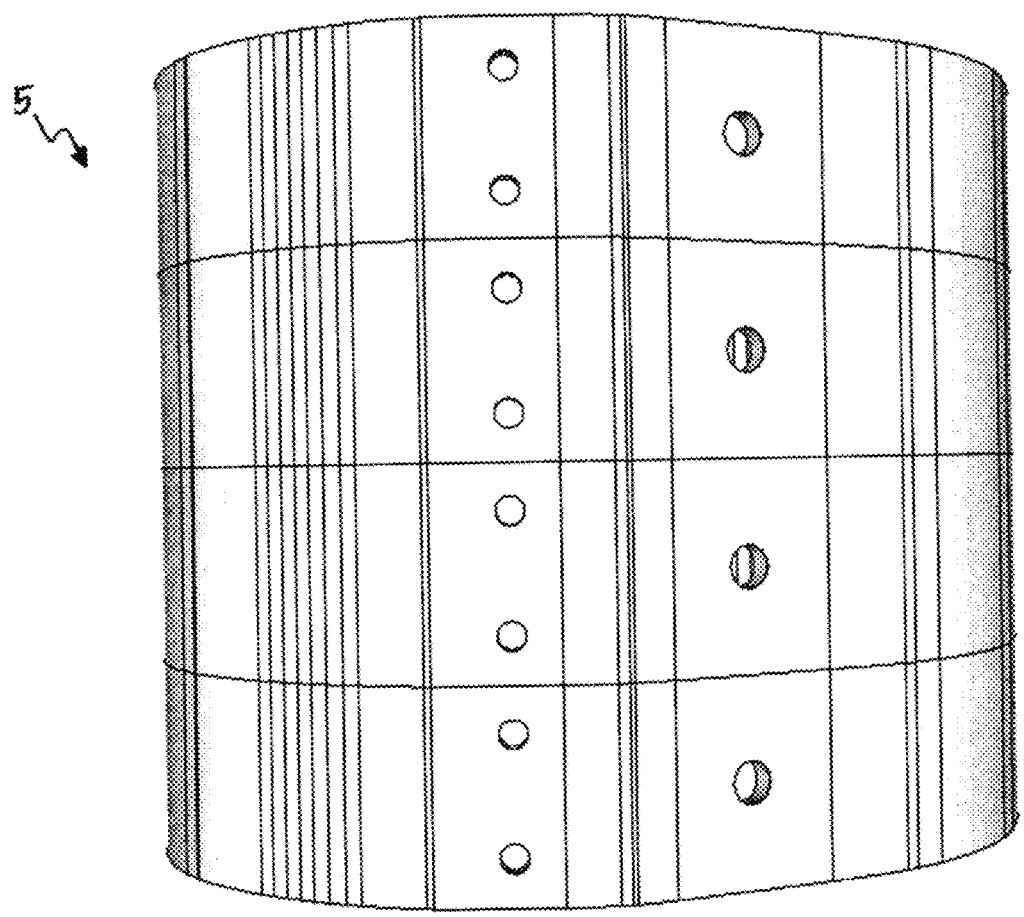
Figure 60:
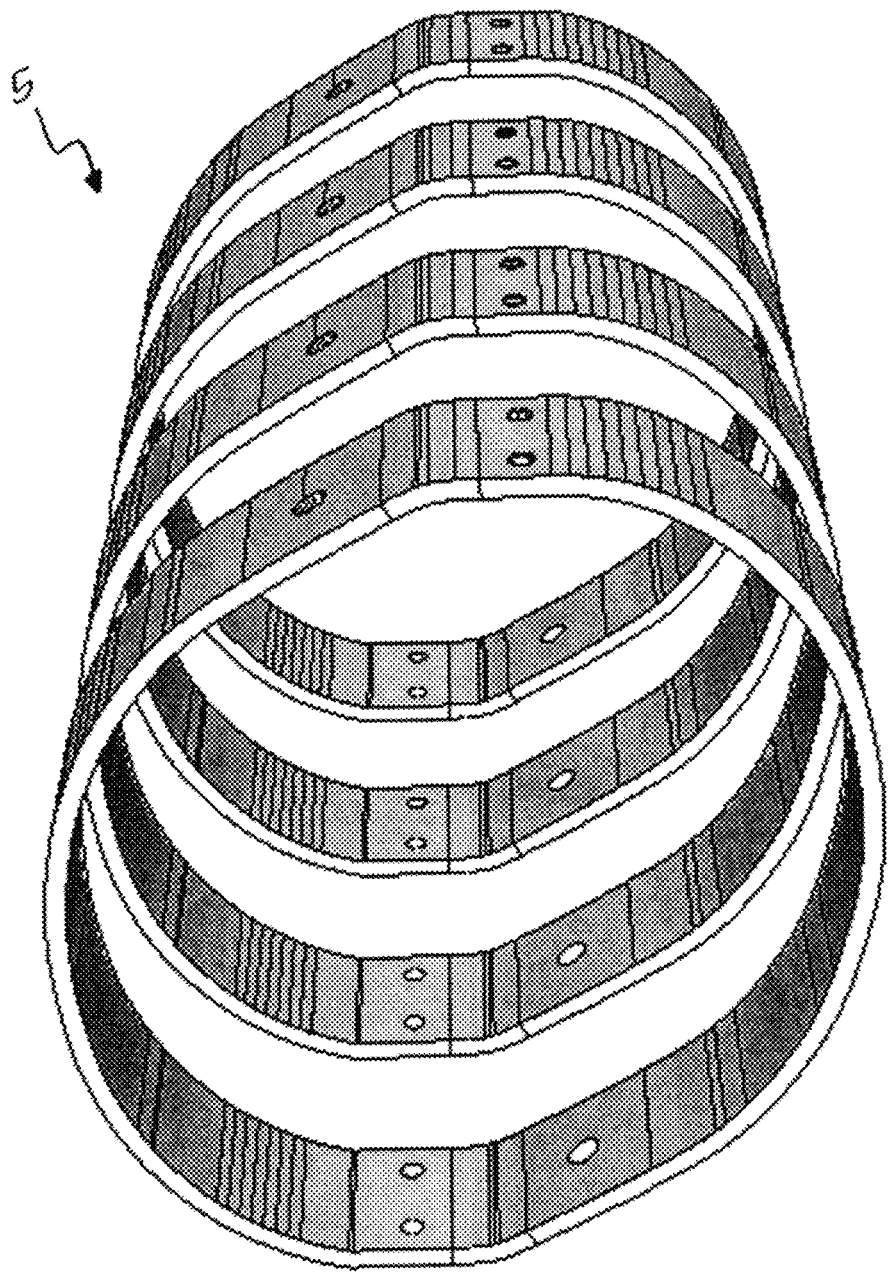
Figure 6E:
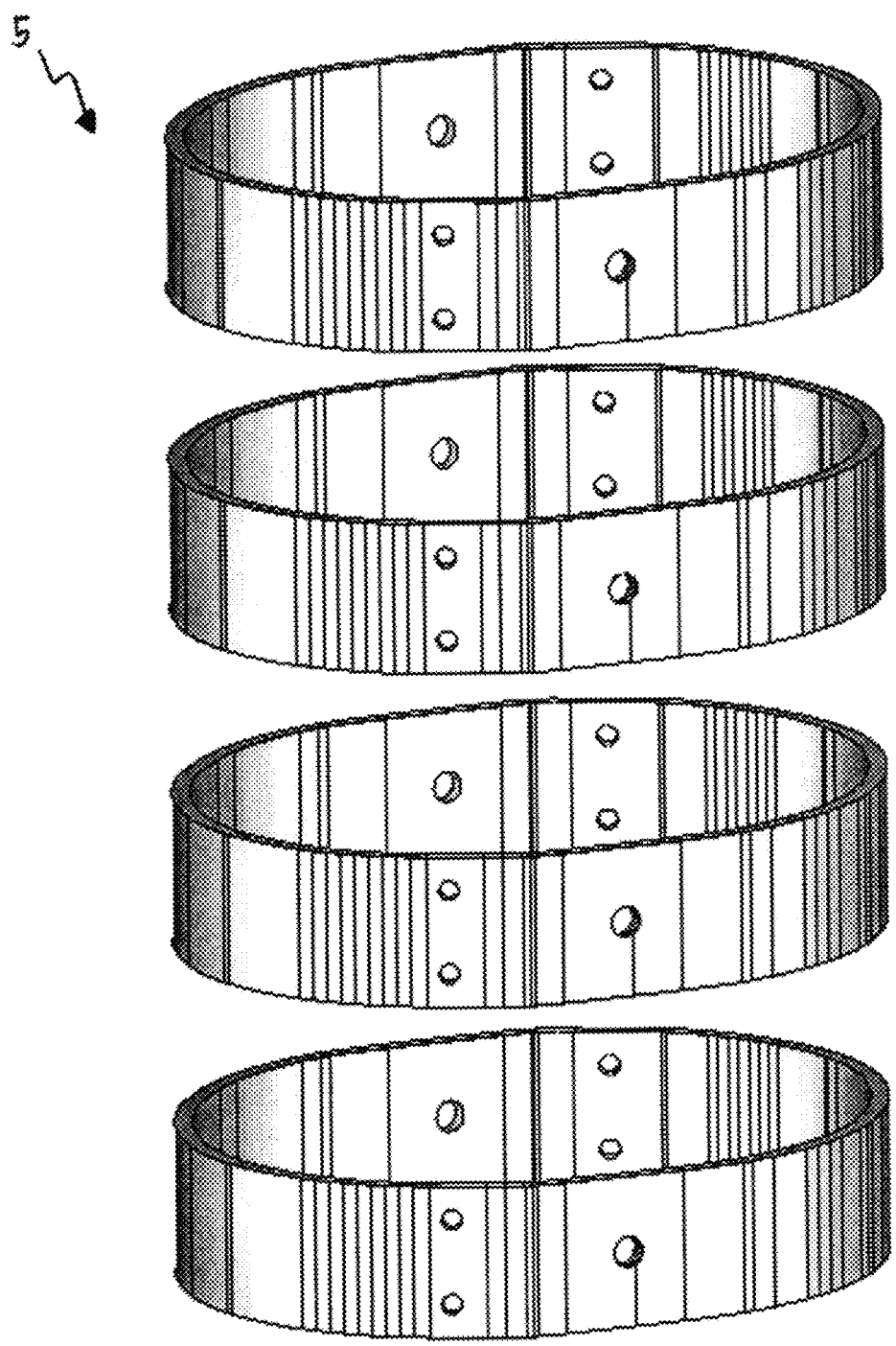
Figure 66:
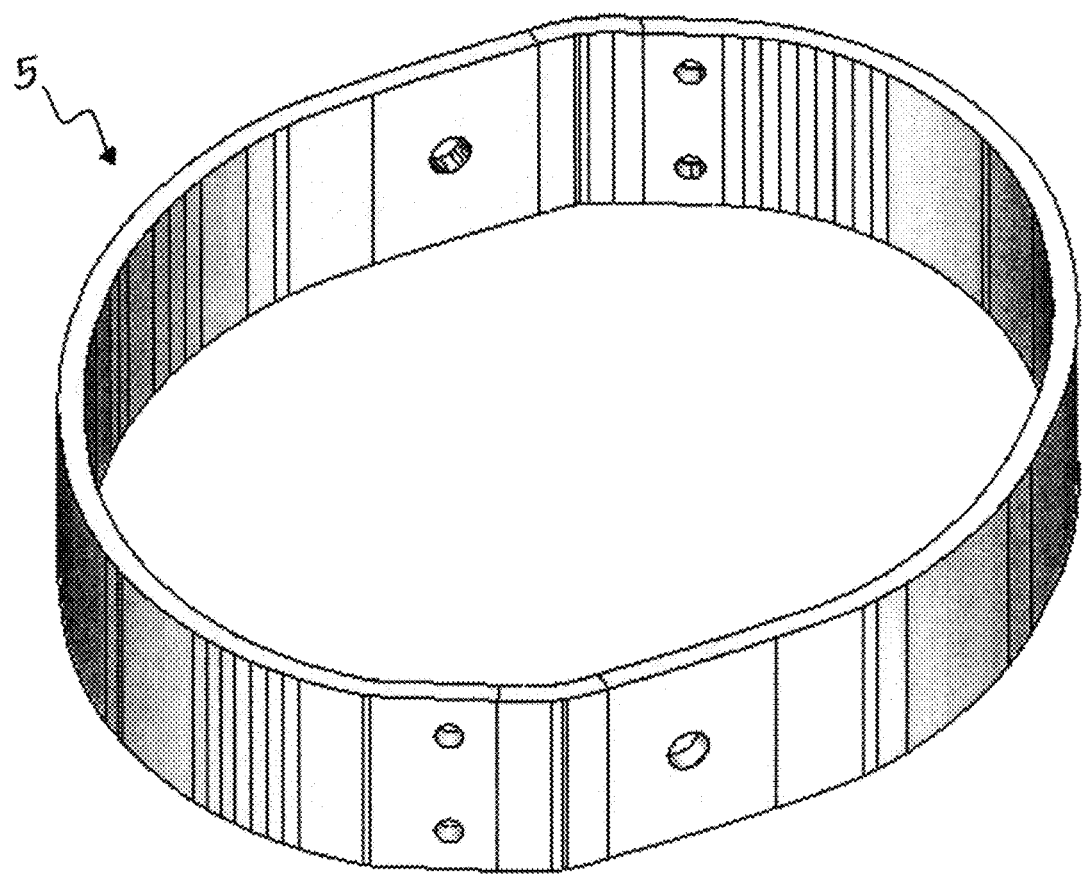
Figure 6H:
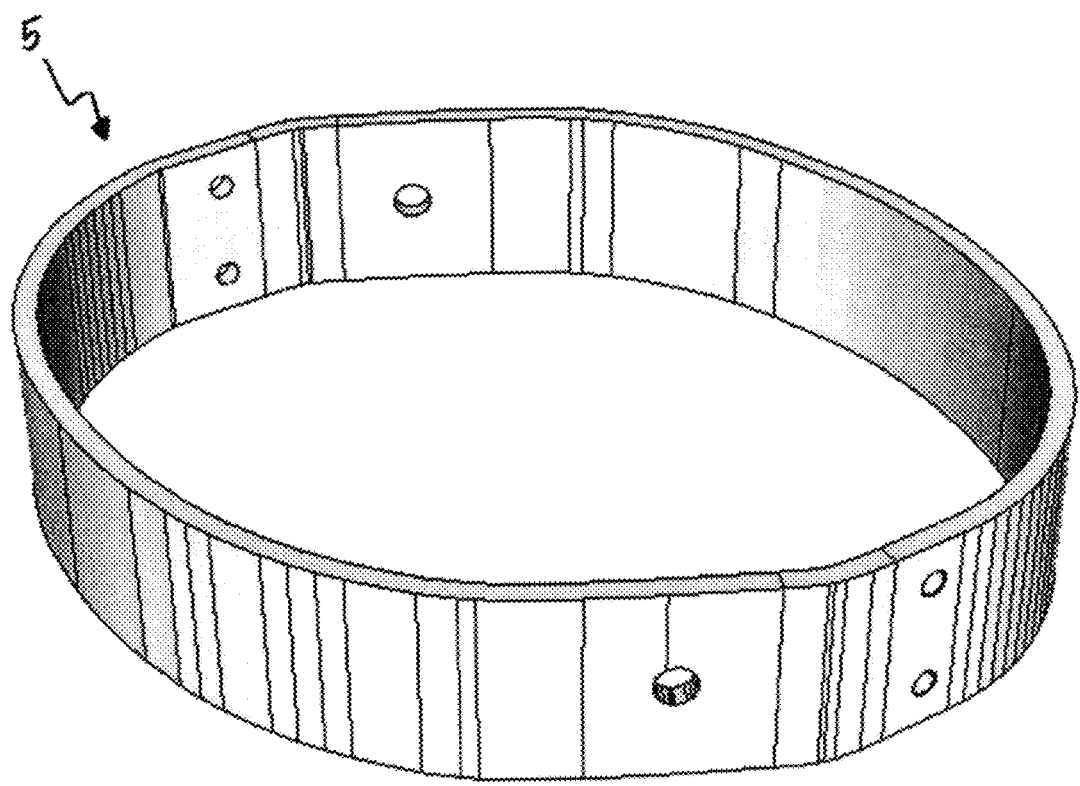
FIGS. 6h and 6i are perspective views of the single energy storing and releasing element shown in FIG. 6g.
Figure 6I:
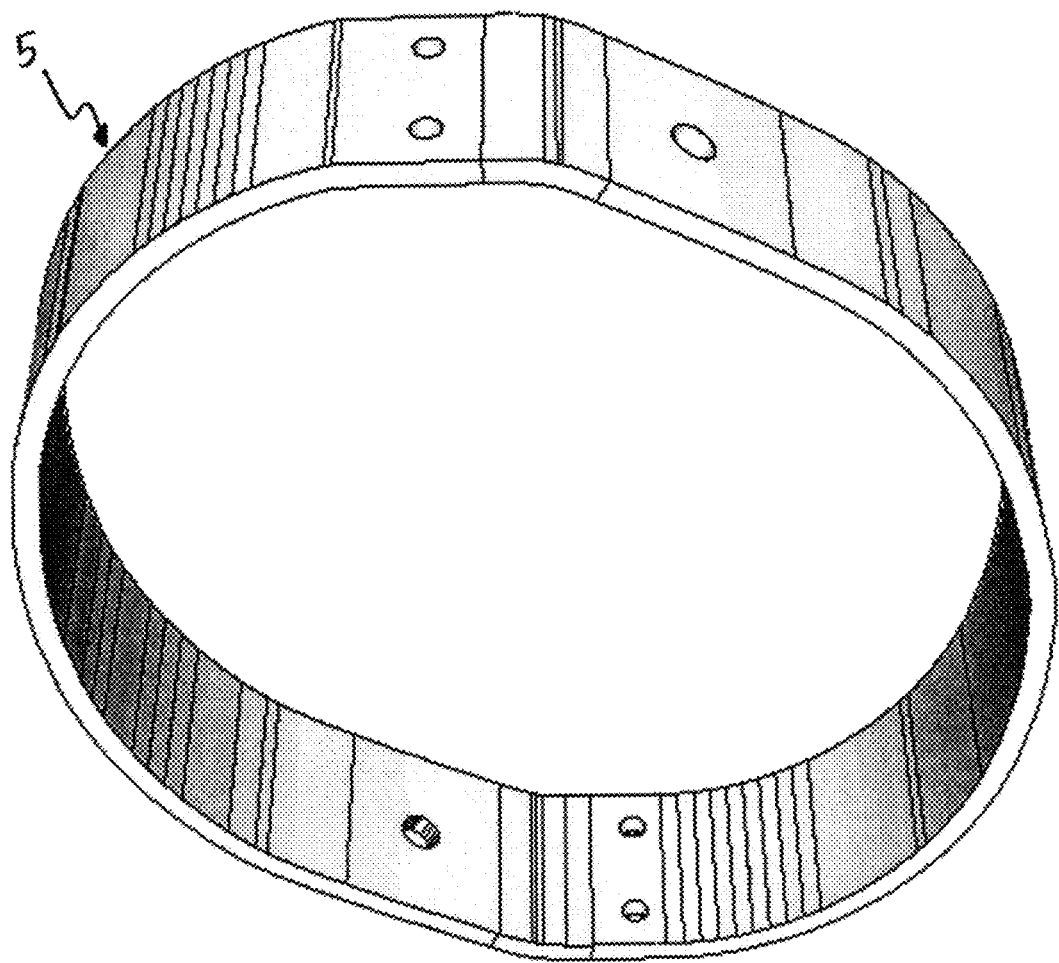
Figure 6J:
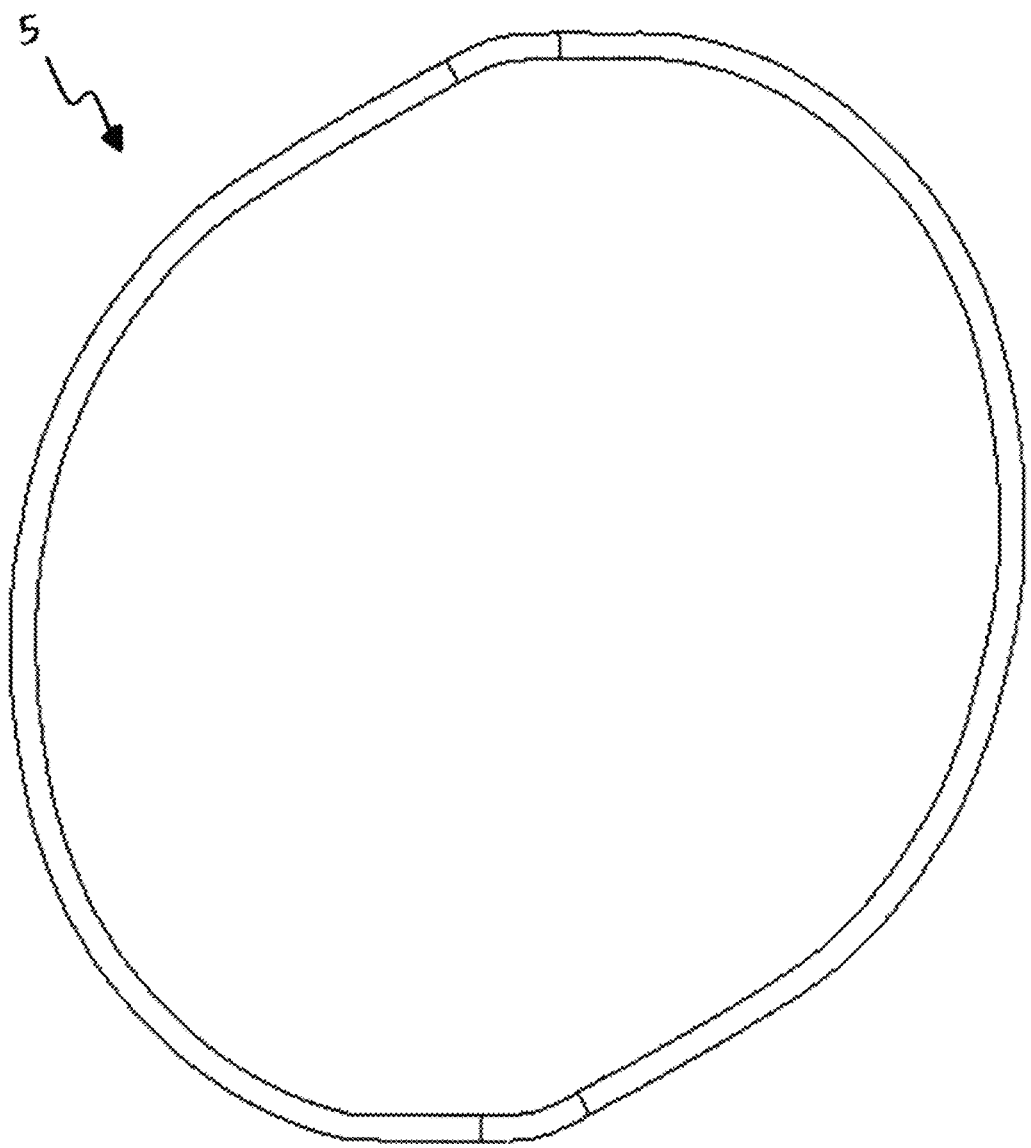
FIG. 6j is an elevation view of the single energy storing and releasing element shown in FIG. 6g.
Figure 6K:
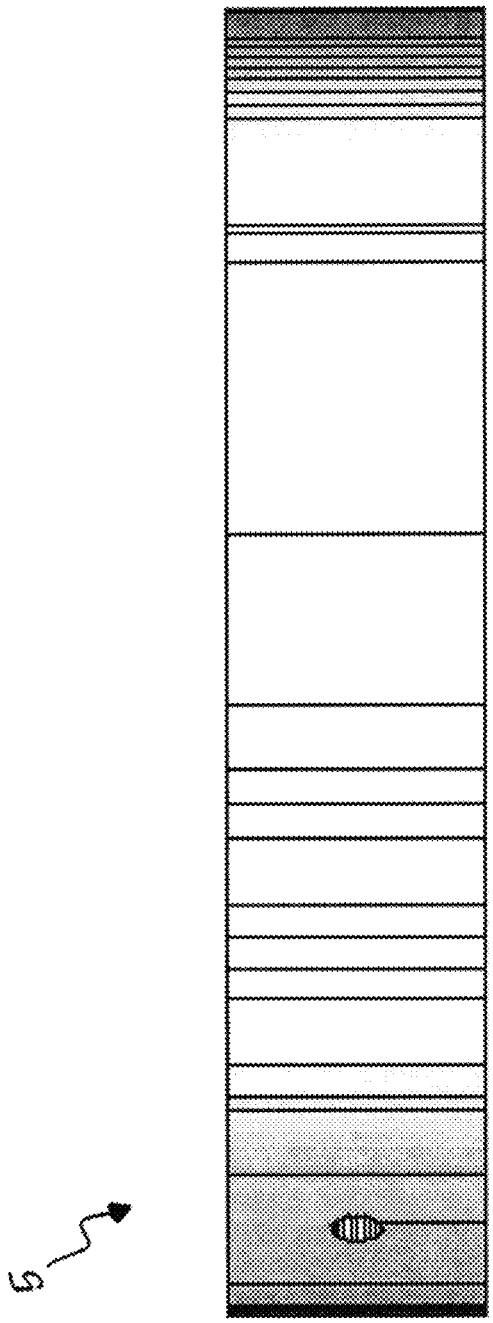
FIG. 6k is a side view of the single energy storing and releasing element shown in FIG. 6g.
Figure 66:
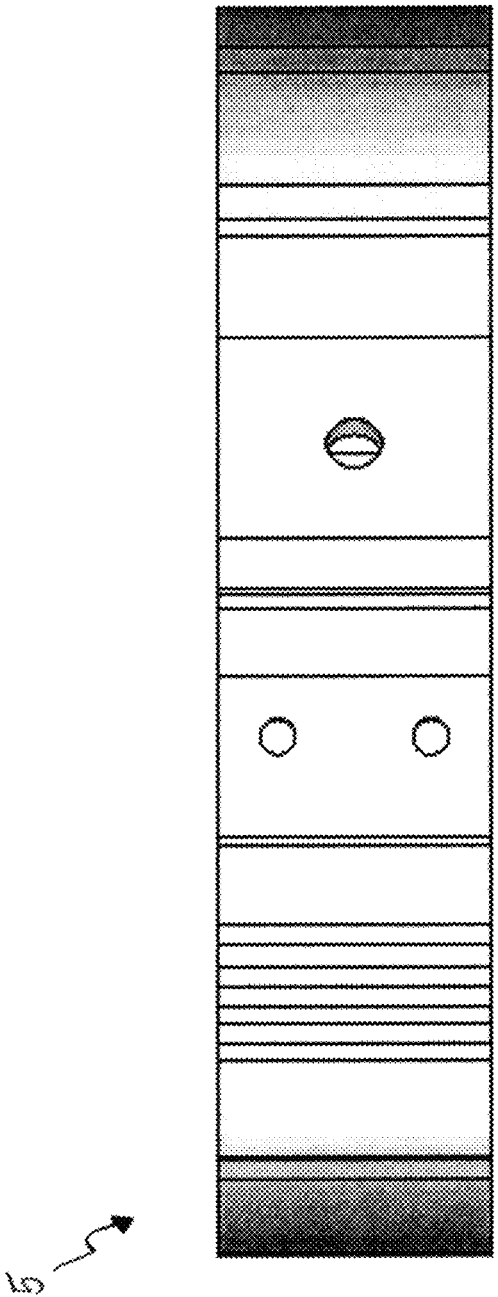
Figure 8:
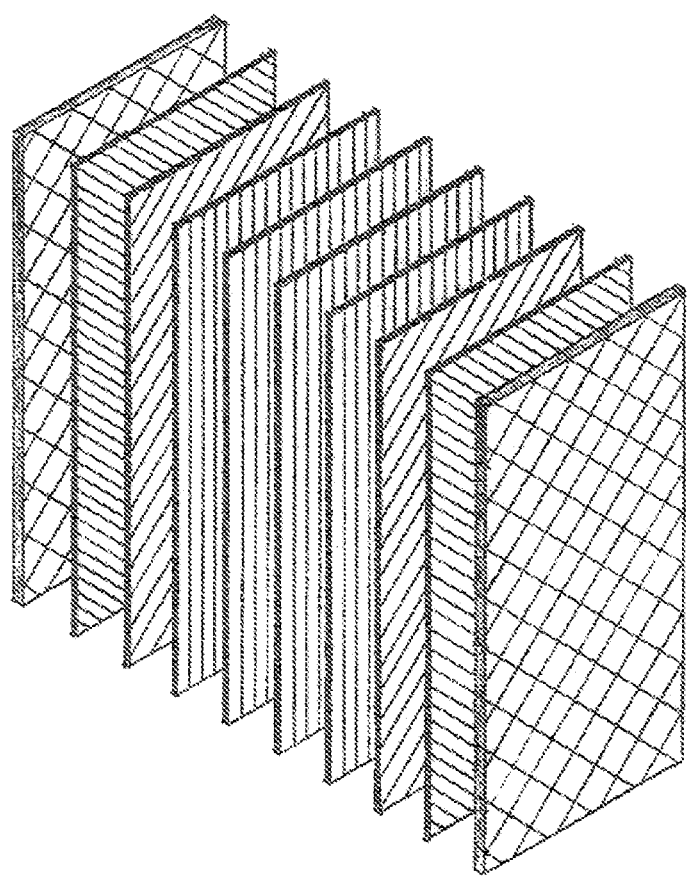
FIG. 8 is a perspective view of composite laminate layers in accordance with the present invention.

FIGS. 5b and 5c are elevation views of another alternative embodiment of the present invention having a single elongated curved energy-storing/releasing member operably attached to the footplate, having "diving board" lines to illustrate the benefits of moving forward the connection point between the C-shaped spring element and the Z-bar member. As described further herein, locating that connection point at or around line B would provide very little, if any, leverage to the patient to be able to vertically compress the C-shaped spring. By moving that connection out toward to toe of the prosthesis, including to and/or beyond line A, the "diving board" is lengthened, allowing the patient to more easily compress the C spring and other elements (and enjoy the soft transitions provided thereby) in the vertical direction."

These benefits of moving forward that pivot point are illustrated in FIGS. 5a, 5b, and 5c. At midstance, the patient's weight is directed straight down, as indicated by weight line C. To illustrate this analogy, two "diving board" diagrams are shown on top of the Single-C embodiment of the invention. Persons of ordinary skill in the art will understand that these diving board diagrams are for illustration only, and are not part of the actual embodiments of the invention that are being described.

In this analogy, arrow C shows the patient standing at the end of the swimming pool diving board(s) A and B. He/she is ready to jump into the pool, which is located to the left side of line/arrow C (although the prosthesis is shown with the patient facing to the right, this swimming pool diving board analogy involves the patient jumping off the "diving board" toward the left side of the drawings). The fixed end of the respective "diving boards" A and B (where the steps to climb up onto the diving board would be located) are to the right side of line C. To visually represent the effects of relocating the pivot point from A to B (or vice versa), the Figures show a preferred location for the lower end of the Single Spring member (shown as just the end of that Single Spring member, in the area of line A), and also shows that same Single Spring member if it were pivoted to be "directly connected" to the middle area of the footplate (this configuration is fully illustrated, with the end of that Single Spring member, in the area of line B). Preferably, Single Spring embodiments locate the pivot point at the lower end of the C-shape rightward (toward the prosthetic toe) sufficiently to enable the patient to readily generate and experience desirable vertical compression within the C-shape. Using the example illustrated in the drawing, the effect of moving that pivot point to location A from location B is to lengthen the "diving board" leverage provided to the patient. As reflected in a comparison of the two "diving boards" A and B, the patient has a much improved springiness and overall experience on the longer "diving board" A (i.e., when the pivot point for the C-shaped spring member is located near A rather than near B).

For any of these single-C spring embodiments, preferably the toe loading characteristics (on the toe portion of the footplate) are identical or substantially the same in midstance, regardless of the length of the "diving board". By providing the longer "diving board" (moving the pivot point to the right), however, the vertical compression of the prosthetic apparatus is greatly improved. The patient can more easily store/release vertical energy (in the main body of the C-shaped element) when provided that longer lever arm of the longer "diving board".

Such a "directly connected" C-shaped spring that was sufficiently stiff to handle a full toe load that the patient could be expected to experience (in the toe-off position, for example) would provide little, if any, vertical compression at mid-stance. Estimating the actual dimensional differences within a relatively standard-sized embodiment of the invention, the "diving board" if the pivot is at location B would be shorter than the location A diving board, by around two inches. This not only would substantially reduce the effective "springiness" experienced by the patient, but because the effective toe lever also would be longer, the toe portion of the footplate would have to be thickened/stiffened to preserve proper toe stiffness. Consequently, the footplate would be heavier (generally a negative for lower leg prostheses) and would be less able to provide the "soft" spring responses that could be achieved with a less thick toe portion.

Extension Support (Swept Back/Z-Bar/Other)

This desirable "forward positioning" of the prosthesis' spring pivot point can be accomplished in any suitable manner. Two of the many alternative ways to "extend" the pivot point toward the prosthetic toe area are illustrated in the drawings, as a "swept-back" portion integrally formed at the lower end of the C-shaped spring, and as a separate "Z-bar" member connecting the Single Spring to the footplate. Both of these approaches preferably provide a relatively stiff connection between the "forward" pivot axis location and the footplate, to enable the patient to control the footplate. Also preferably, both approaches also provide at least some additional energy storing/releasing action within their respective "swept-back" and "Z-bar" structures, and therefore are able to provide additional opportunities to a prosthetist to fine-tune or adjust the dynamic performance of the prosthesis.

By way of comparison, in the Double C-spring approach described above (using Spring 1 and Spring 2 in a single prosthetic assembly), the attachment points (for both the upper and the lower ends of Spring 1 and Spring 2) do not have to be as far forward as with Single Spring embodiments. The multi-spring embodiments instead preferably provide the desired vertical performance by simply making Spring 1 less stiff and more flexible (and relatively "thinner" and lighter), and preferably providing the desired toe action and footplate control, etc. via Spring 2.

Figure 3A:
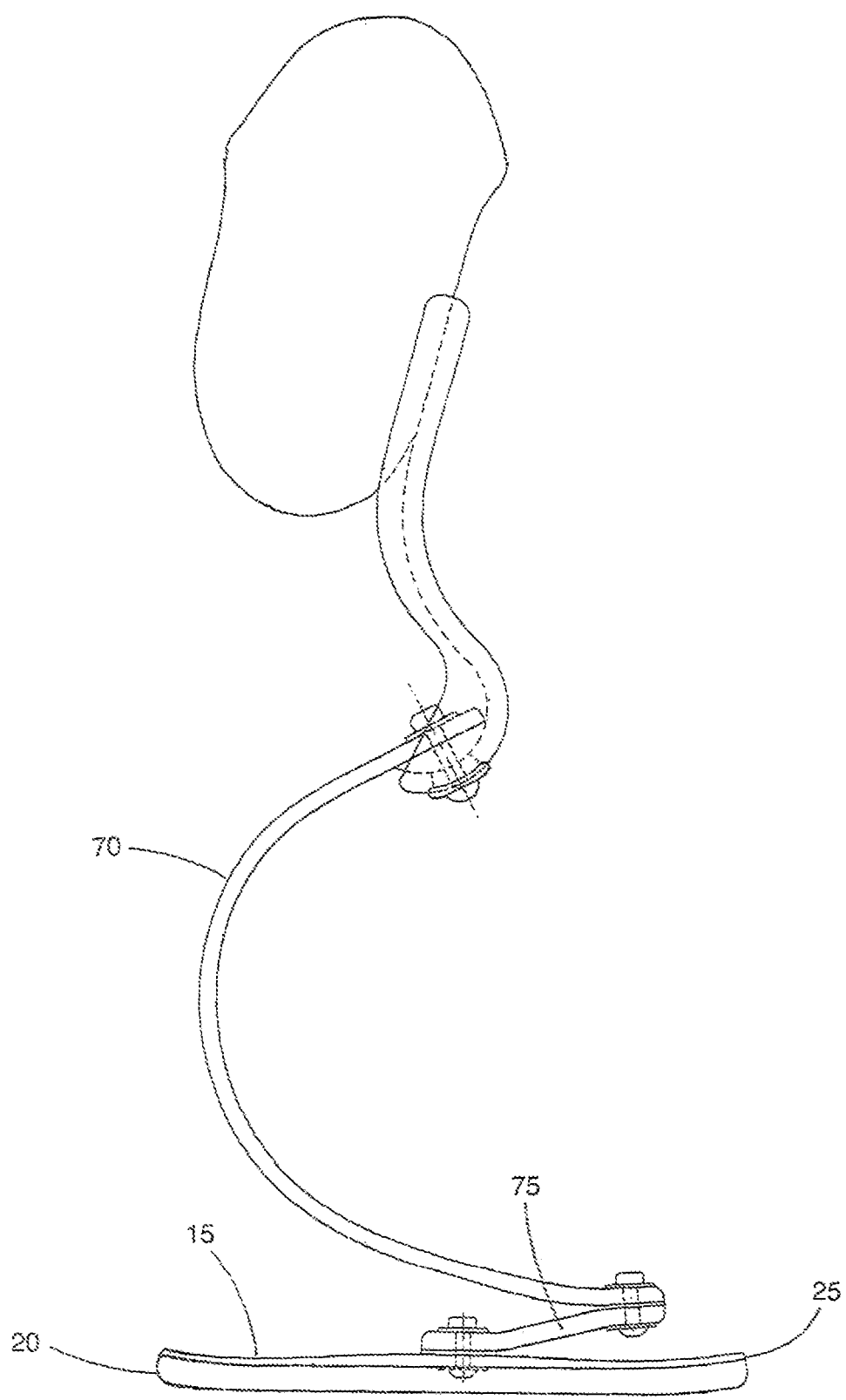
FIG. 3a is an elevation view of an alternative embodiment of the present invention having a single elongated curved energy-storing/releasing member and a Z-bar extension portion.
Figure 3B:
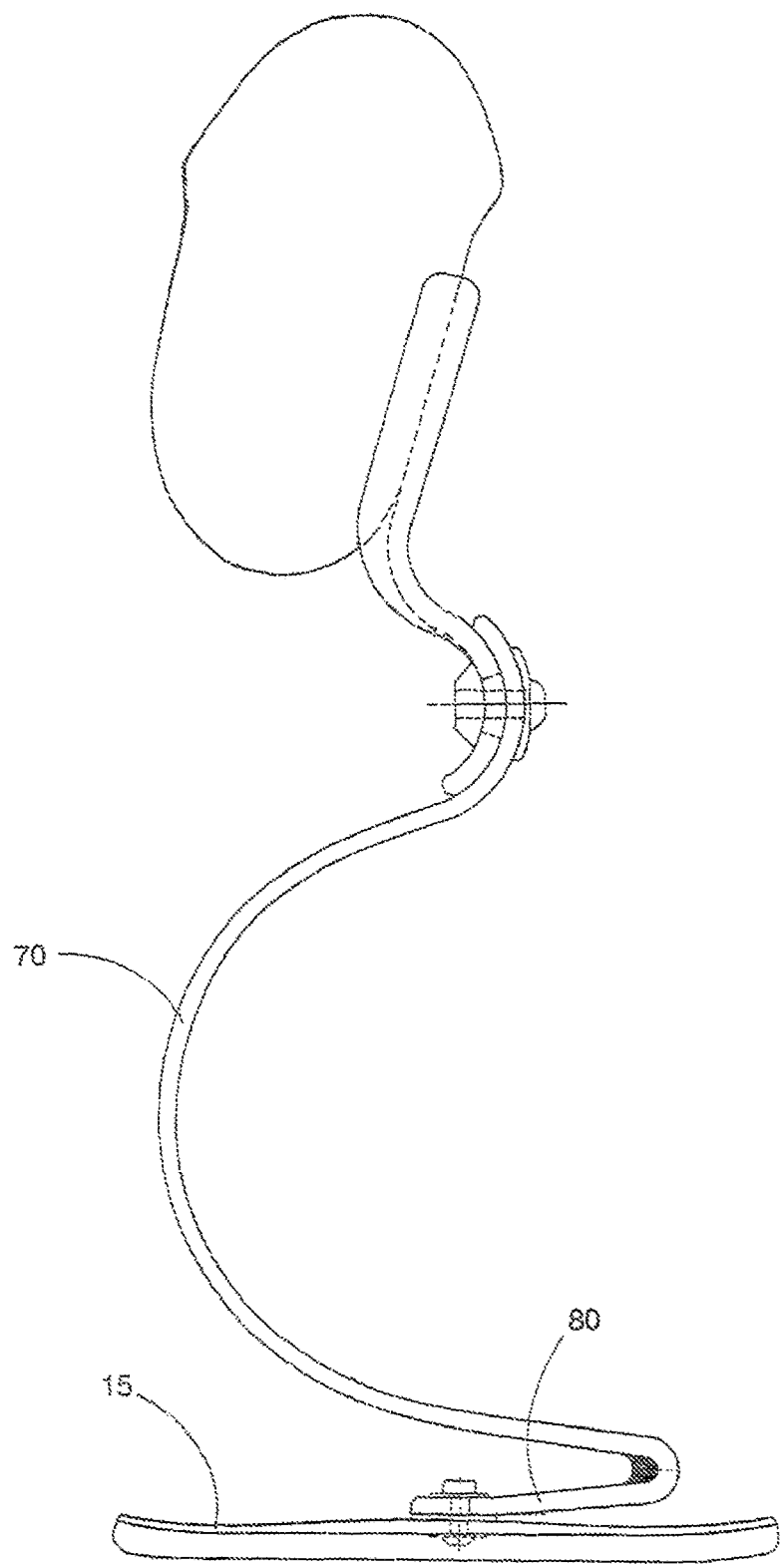
FIG. 3b is an elevation view of an alternative embodiment of the present invention having a single elongated curved energy-storing/releasing member with a swept-back extension portion.
Figure 3C:
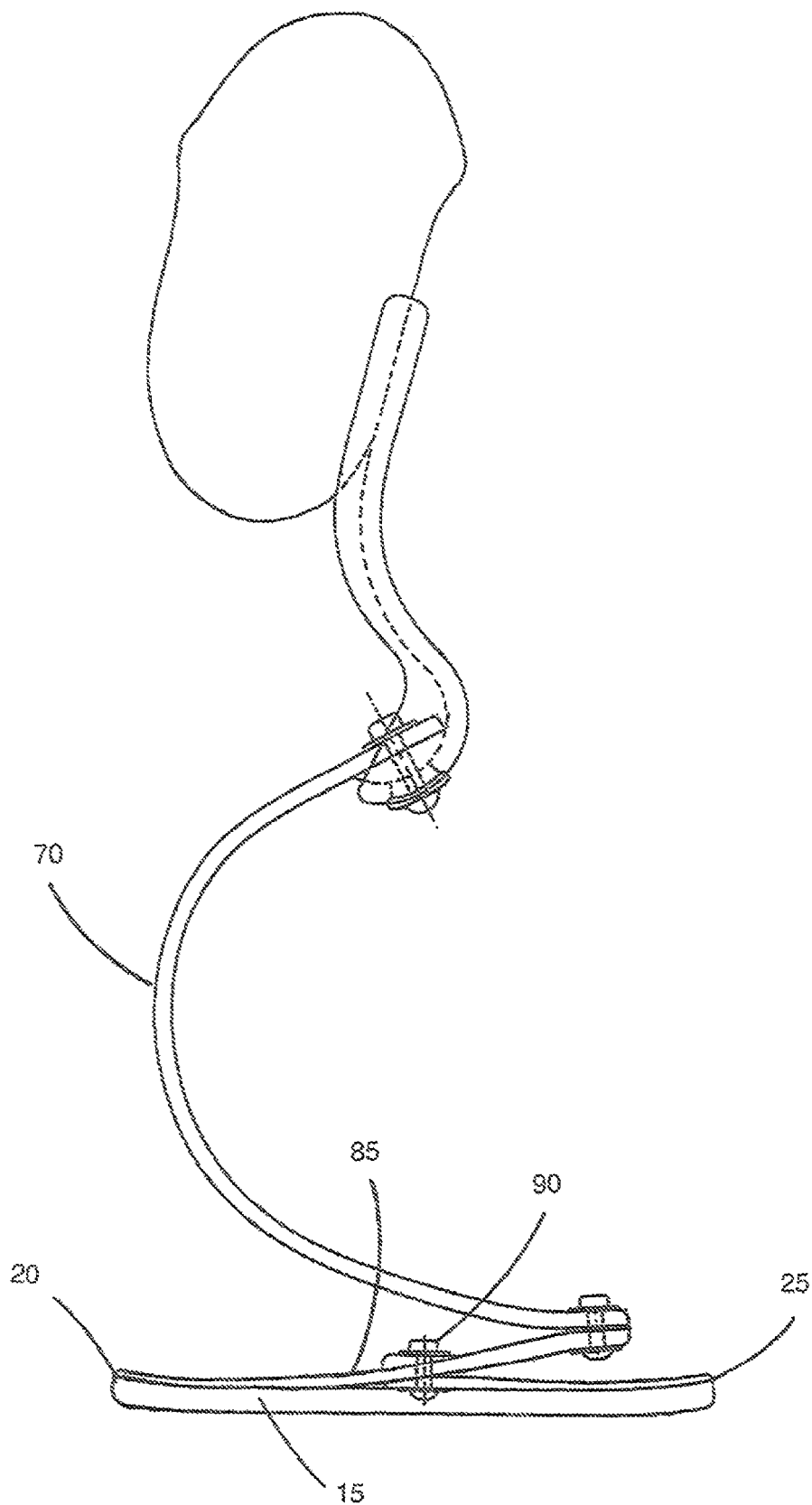
FIG. 3c is an elevation view of an alternative embodiment of the present invention having a single elongated curved energy-storing/releasing member and a toe extension portion of the footplate operably connected thereto.
Figure 3D:
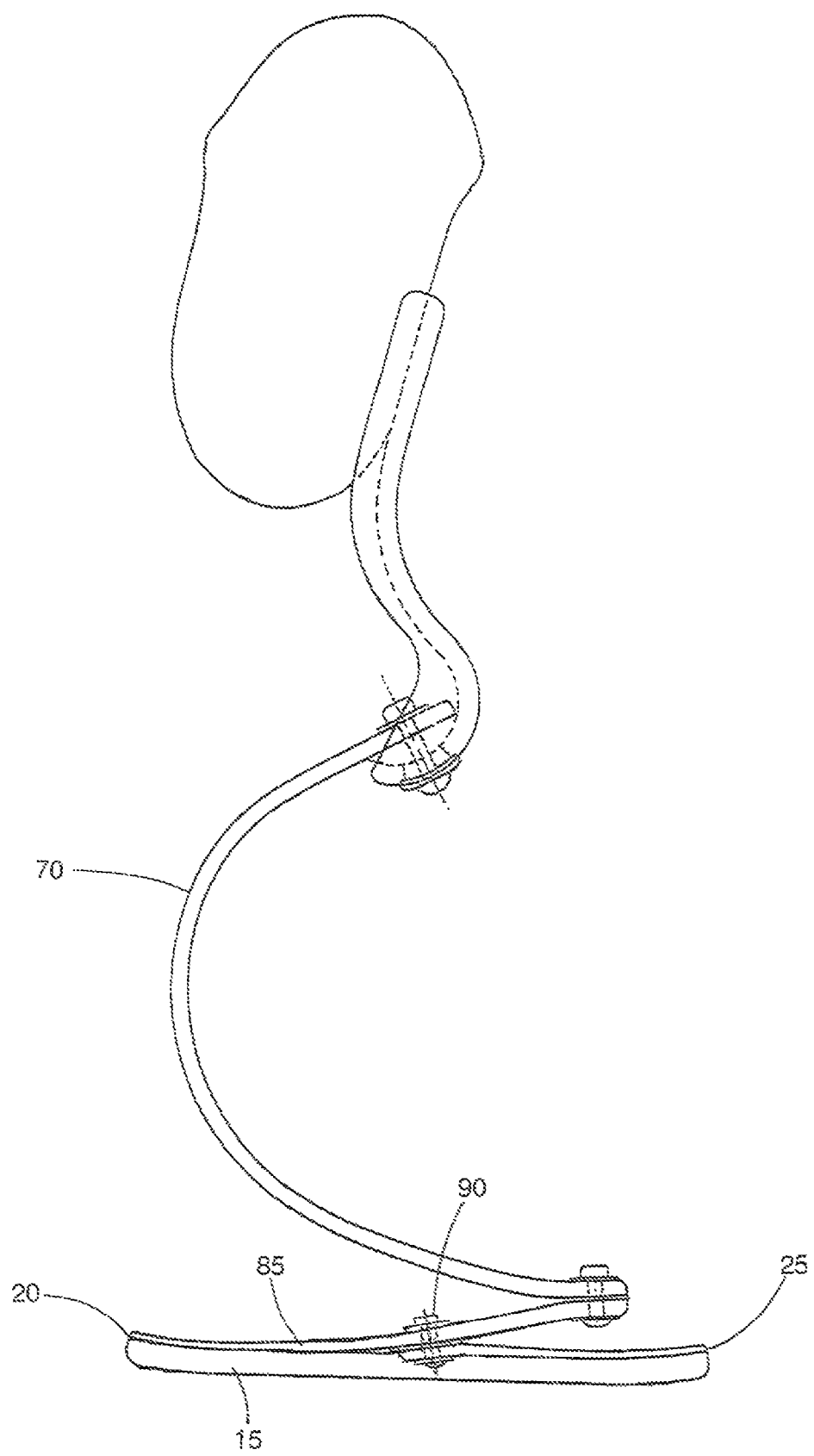
FIG. 3d is similar to FIG. 3g, but having an angled bolt for connecting the toe extension portion to the footplate.

The "swept back" structure is illustrated in FIG. 3f as a relatively tight backwards C curve or downward bend formed near the lower front end of the main body of the C-spring element. From that nearly 180-degree bend, the "swept-back" portion extends back and downwardly to attach to the middle area of the footplate. As with the other components of the invention, the "swept-back" and "Z-bar" structures can be fabricated from any suitable material and via any suitable process. Preferably, the "swept-back" portion is fabricated as an integral part of the Single C Spring, from the same types of materials and processes, and therefore generally possesses the same or similar energy storing/returning functionality as the rest of the "C" member.

The "Z-bar" structure is illustrated as a relatively flat member extending between approximately the middle of the footplate forwardly and upwardly to the area of the front pivot point for the C-shaped spring. In the embodiments shown in the drawings, the ends of the Z-bar are slightly angled with respect to the body portion of the Z-bar, to help align those ends with the respecting confronting surfaces to which they are to be attached.

Persons of ordinary skill in the art will understand that precise shapes, sizes, orientations, and performance characteristics of the "swept back" and/or Z-bar or similar structures/extensions can vary widely depending on the application and the desired performance of the C-spring element and the overall prosthetic assembly. Further, persons of ordinary skill in the art will understand that the connections to the footplate (and to the Single C-Spring in the case of a Z-bar type extension) can be accomplished by one or more bolts (as shown), by glue or adhesive, or by any of a wide range of alternative methods and/or apparatus.

Preferably, the Swept-back or Z-bar portion of this type of Single C embodiment is relatively stiff, but has some flexibility. In certain embodiments, these portions of the prosthesis or prosthetic assembly can be stiffened (relative to other parts of the prosthesis) by adding fiber (e.g., 3-4 plies) at those locations prior to impregnating the fibers and molding the part(s), although other embodiments may have no such "extra" plies. Persons of ordinary skill in the art will understand that any other suitable method of adjusting or affecting the spring characteristics of the extension components (and/or the overall prosthesis) may be used.

In embodiments of this type, the effective pivot or loading length of the "heel" (for at least certain aspects of the prosthesis' dynamic loading and performance, etc.) is longer than just from its preferred connection point near the middle of the footplate back to the rear-most portion of the footplate. Because these embodiments preferably move the effective pivot point forward (ahead of the point at which the extension element is actually attached to the footplate), the effective length of the "heel" preferably is likewise extended, so that it runs from near or at the forward-most portion of the Swept-back or Z-bar extension element to the farthest-back portion of the footplate. That extra lever arm length provides many benefits in comfort and performance and ease-of-use of the prosthesis, but it also makes it much easier for the patient to compress the heel (the patient has increased leverage to bend the heel portion). Accordingly, in order to prevent excessive heel compression, the overall stiffness of that lever arm (and the components of it, such as the Swept-back or Z-bar and the rear portion of the footplate) preferably is designed and selected to provide the desired range of compression for the patient, but to not be so flexible as to make the heel too soft. Persons of ordinary skill in the art will understand that this stiffness can be customized to meet a variety of factors, including the patient's weight and activity level, and others, and that the invention lends itself to a modular approach that allows ready interchange of components having different characteristics, dimensions, etc.

Generally, in this type of embodiment of the invention, the further forward the pivot point for the main vertical spring, the more of the main body of the C-shape is available to provide the desired energy function for vertical and other loads and the more leverage the wearer has to smoothly load and unload that Single Spring. For example, connecting the lower end of the C Spring directly to or near the forward-most end of the footplate's toe portion would provide the maximum vertical spring action for a given set of prosthetic elements.

However, such embodiments would have several drawbacks. Among other things, the further that the pivot point is moved toward the toe, the thicker and heavier the associated forward footplate portions and the connecting bolts or other hardware would have to be (to withstand the greater forces imposed by the loading on those effectively longer lever arms). This weight increase would not only make the prosthesis less comfortable for the wearer, the concentration of that weight toward the prosthetic toe might impose on the wearer some uncomfortable bending forces (such as via the wearer's socket, for example). In addition, that increased size and component position would make it more difficult or even impossible to fit the prosthesis into a shoe.

In addition, the further forward the pivot point, the less the effective lever arm for any toe flexing. This can be desirable to a certain extent, including because the less leverage that the toe portion of the footplate has (in front of that pivot point), the less strong and less massive the toe portion of the footplate needs to be. However, if the pivot point reached or extended past the end of the toe, there would be no desirable toe roll-up or other desired toe action.

Accordingly, in preferred embodiments, including those that use either the swept-back and Z-bar approaches, the pivot point is sufficiently rearward of the toe end that it allows the toe portion of the footplate to function properly, such as by allowing the toe portion to roll-up during toe load/toe off. Preferably, the toe portion of the footplate is tapered and can "curl up" as the toe load increases, and that curling movement shortens even further the effective length of the toe's lever arm (with respect to the pivot point), but still provides at least some desirable degree of toe roll-up.

Persons of ordinary skill in the art will understand that much of the discussion above regarding heel strike, mid-stance, and toe-off also applies to single C-spring and other embodiments of the invention. Below are some additional comments specific to such single C-spring embodiments. Exemplary drawings of each of these positions are shown in FIGS. 4a, 4b, and 4c.

Heel Strike

Figure 4A:
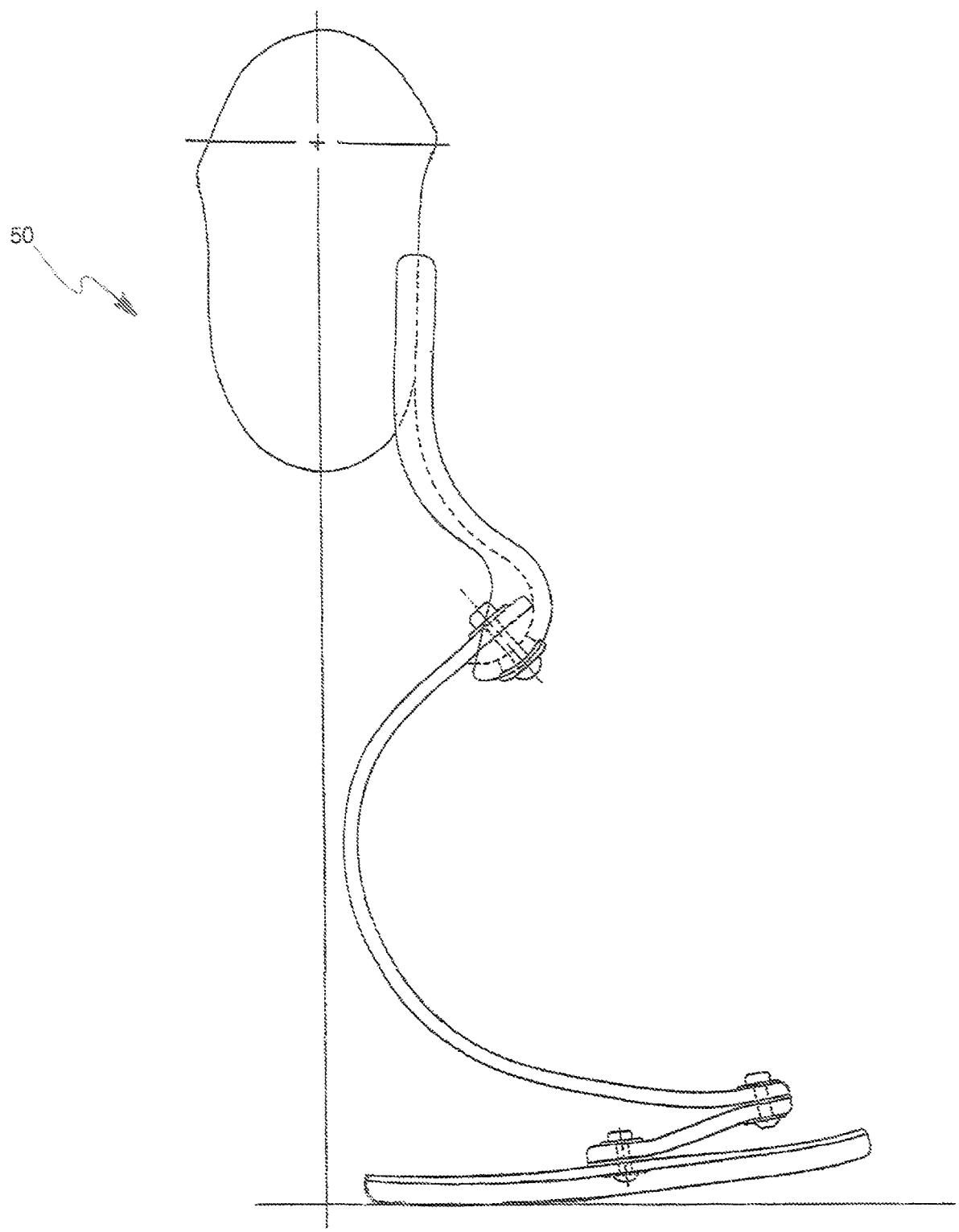
FIGS. 4a, 4b, and 4c show the device of FIG. 3a in roughly heel-strike (FIG. 4a), mid-stance (FIG. 4b), and toe-off (FIG. 4c) positions (the precise curvature and the smoothness of the curved spring elements may vary from that shown in this drawing). A vertical line indicates the vertical load as the patient passes through these positions of his/her stride. In the toe-off position, the toe portion of the footplate, the C spring, and the Z-bar have all been compressed somewhat from that loading.
Figure 4B:
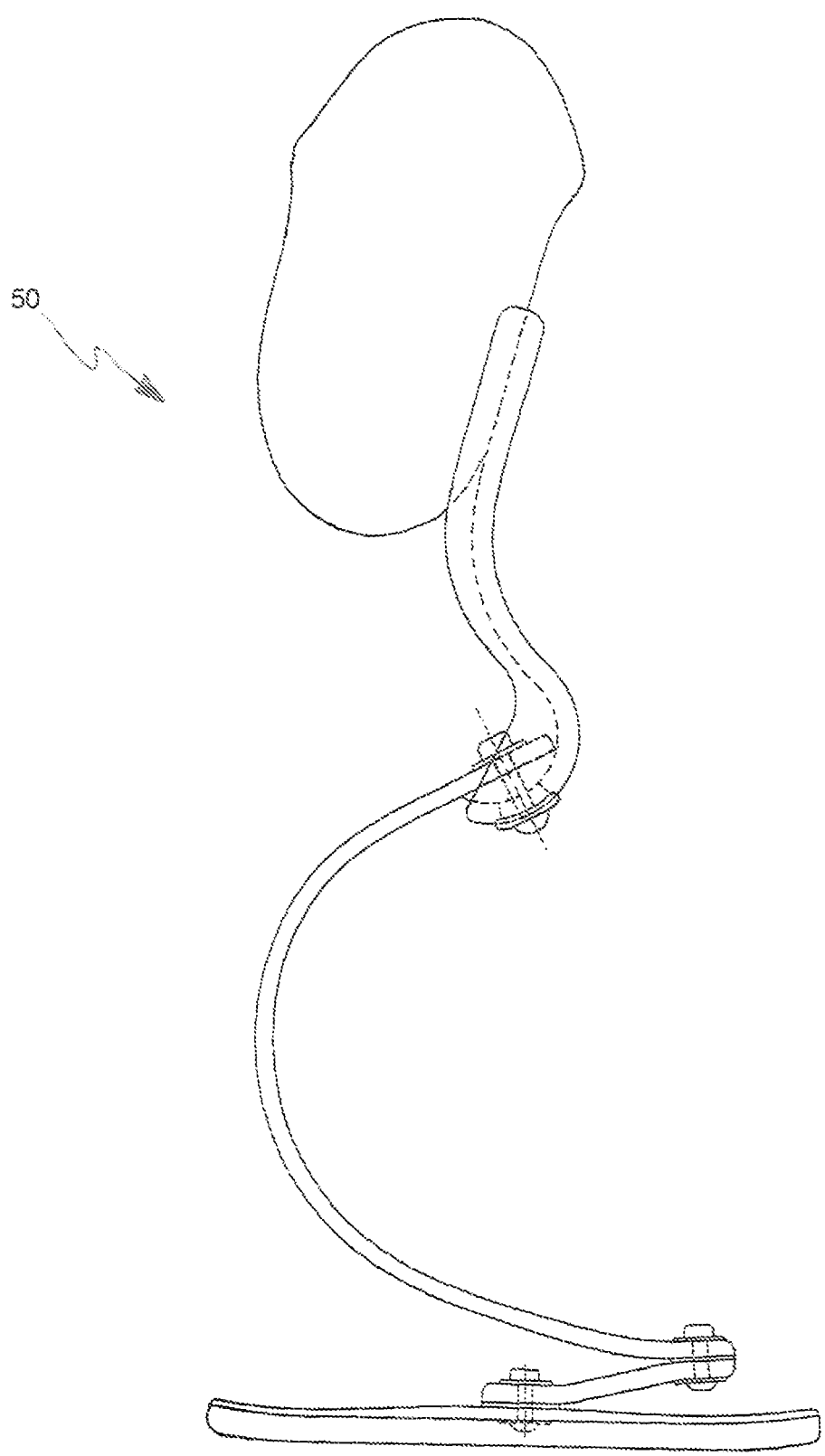
Figure 4C:
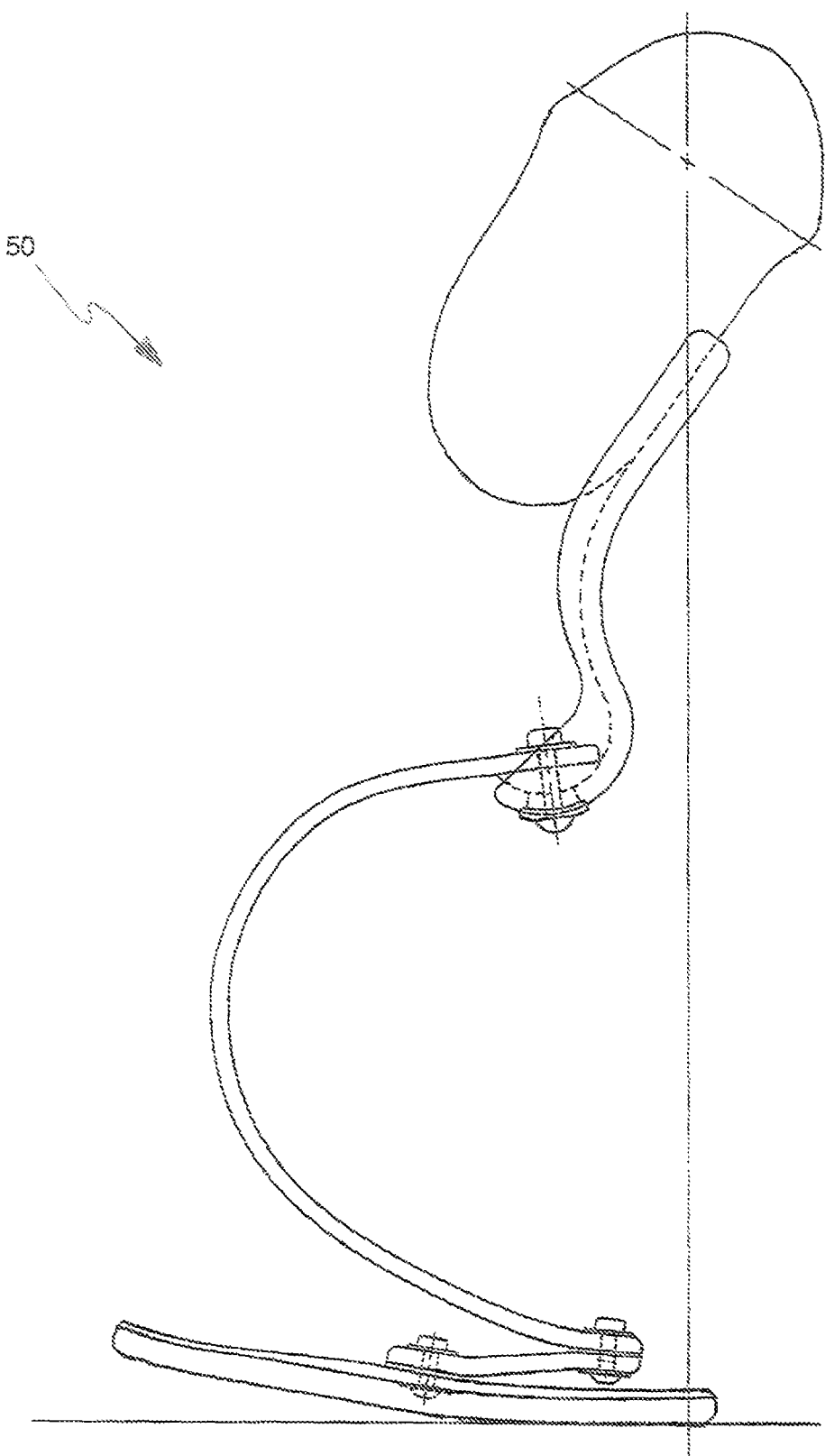

FIG. 4a shows a conceptual view of a Single C Spring embodiment as it may be positioned during a heel strike condition. The more-forward pivot axis and the relatively stiff lever arm between the heel and that pivot axis allows the Single C Spring to help slow and/or limit the plantar-flexion that otherwise would occur as a result of the heel portion of the footplate being pushed upwardly. As the toe portion is pulled downwardly (because of the heel contacting the ground), the stiff linkage between the footplate and that more-forward pivot point tends to "open" the Single C Spring (much like Spring 2 above is "opened" during heel strike).

Mid-Stance

FIG. 4b shows a conceptual view of a Single C Spring embodiment as it may be positioned during a mid-stance condition. As indicated above, by moving forward the pivot point for the lower front lip of the C-shaped spring element, the prosthesis preferably provides spring action/absorption of vertical loading even at midstance, and preferably does so with a gentle and gradual spring action within the main body of the C-shaped spring and otherwise. As explained above, unlike prostheses that align the spring pivot at or near the patient's midstance weight line, the preferred more forward location of the invention provides to the patient additional "diving board" leverage, making it easier for the patient to manipulate and use the prosthesis.

Toe-Off

FIG. 4c shows a conceptual view of a Single C Spring embodiment as it may be positioned during a toe-off condition. In some single-C embodiments of the invention, the toe portion of the footplate preferably is relatively soft, so that during toe-off, that toe portion "rolls up" toward the forward-most portion of the Swept-back or Z-bar. Preferably, this mimics the ball of a normal foot, in that the end of the toe plate bends upwardly (like a normal big toe during toe-off). As it does so, and especially if the toe portion collapses all the way into contact with the lower front lip of the C-shaped spring element, the effective "pivot" point between the toe and the ground or other surface can move away from the front end of the footplate and back towards the center of the footplate. In certain preferred embodiments, this can generally move that "pivot point" into approximate vertical alignment with the forward-most portion of the Swept-back or Z-bar. The resulting sensation and performance in this position mimics that of a normal foot, in that the patient's sensation that the vertical load line is at or near the "ball" of the foot, and the C-shaped element preferably is also able to provide a desired amount of vertical compression (as would a normal human ankle).

Thus, these types of embodiments of the invention preferably move the C member's main pivot point forward, and preferably also better allow the prosthesis to provide vertical compression and related energy storage/return in many situations. One example is when a patient steps off a curb and onto the street on the patient's prosthesis. In such situations, the patient's weight can be imposed on the prosthesis in a substantially vertical, downward direction. If both the heel and toe of the prosthesis contact the street at generally the same time, any plantar flexion and/or dorsiflexion forces tend to offset each other, so that the preferred flexible spring action of the heel/toe portions of the footplate are inoperable—the entire footplate stays relatively flat. This leaves vertical weight loading (such as the patient's weight as he/she steps down onto the street) to be absorbed or cushioned (if at all) by other parts of the prosthesis. By moving the pivot point forward, these embodiments of the invention allow the main body of the "C" shaped element to compress and cushion the impact from that vertical loading.

Said another way, the invention preferably avoids "locking" the C-shaped spring into a stationary position over the flat toe/heel footplate at midstance. Instead, these embodiments of the invention pivot from the front pivot location (toward the toe), and thus provides some vertical "give" even if the toe/heel of the foot portion are relatively "fixed". On a related point, the Swept-back or Z-bar or other extension members not only provide a longer "diving board" (for energy storage/release within the main body of the C member), those members also preferably provide some desirable amount of vertical give and/or flex within the members themselves, allowing further fine-tuning and improvement of the performance of the prosthesis and the experience of the patient.

Persons of ordinary skill in the art also will understand that moving forward the pivot point allows the main body of the C-shaped spring to be longer and larger than it otherwise would be. This aids in providing a much gentler and more gradual (and natural) spring action under vertical loading.

FIGS. 17, 17A, 17B, and 18 through 25 are elevation views illustrating some of the many other various combinations and permutations that can be used to practice the invention. Among other things, they generally show the use of more completely circular embodiments of spring elements. This use of more completely curved springs can be accomplished in a wide variety of ways; as shown, the adapters that connect the upper and/or lower ends of the spring elements are configured to include a matingly curved contact surface that at least approximates the relevant curvature of the spring element. They also show the use of supplementary spring elements, energy storing/releasing foot and/or toe elements to further refine and enhance the performance of the prosthesis, straps/restraints to limit the deformation of the prosthesis, and cushion/bladder elements to smooth the transition of energy loading and release.

The aforementioned single spring embodiment with the separate toe section preferably includes a non-tapered relatively thin toe plate. Also preferably, and as shown for example in FIG. 25, the toe plate extends behind the lower/heel bolts (or other connection between the upper C spring and the heel/foot plate) and has a restraining strap or other restraining means at its heelward end, which provides ample operational/bending length for the desired toe action. This preferred bending assembly thus combines the performance of a long "diving board" (a long forward attachment position for the main C spring, as discussed elsewhere herein) with a desirable operational bending energy storing spring as a toe element.

Connector

Figure 9:
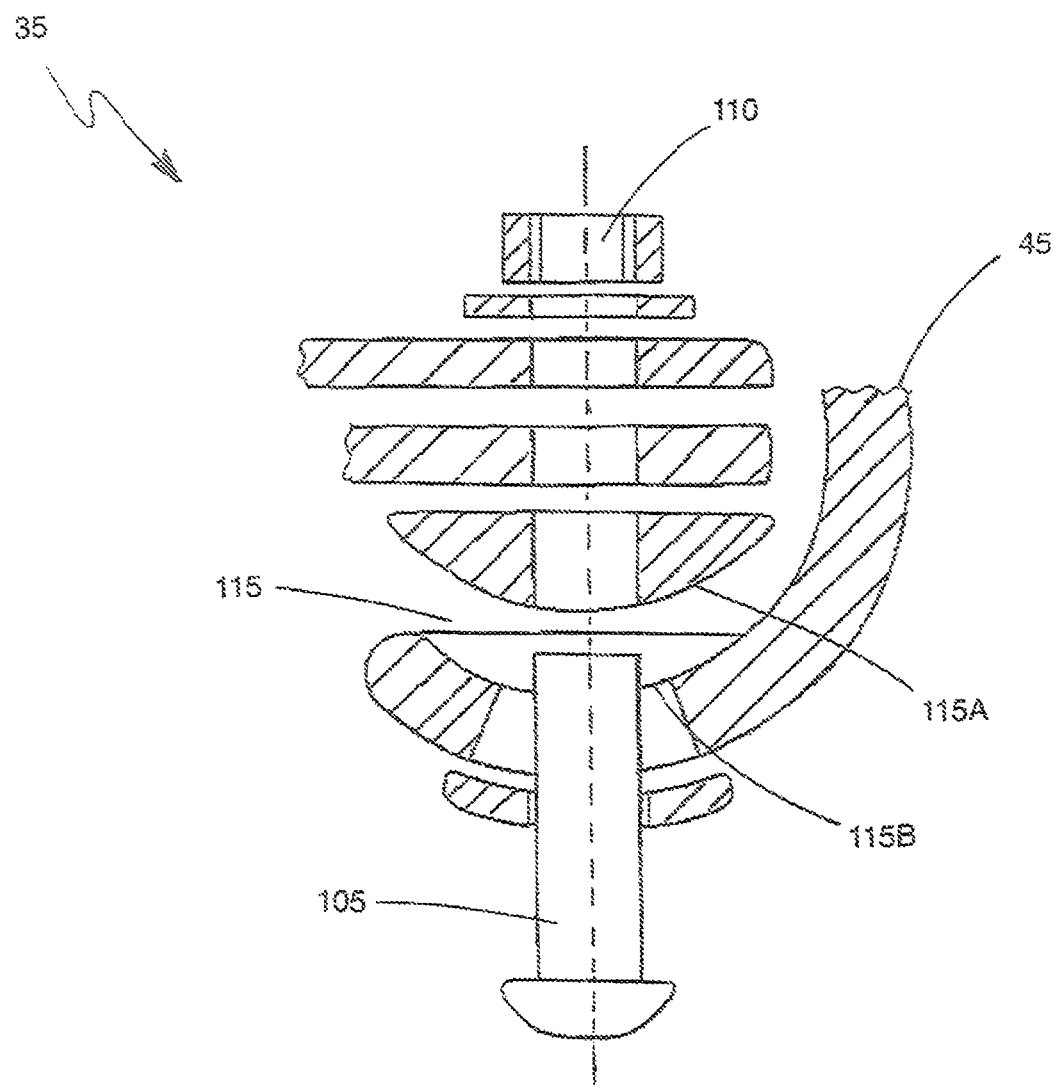
FIG. 9 is a section view of an upper connector in accordance with the present invention.
Figure 10A:
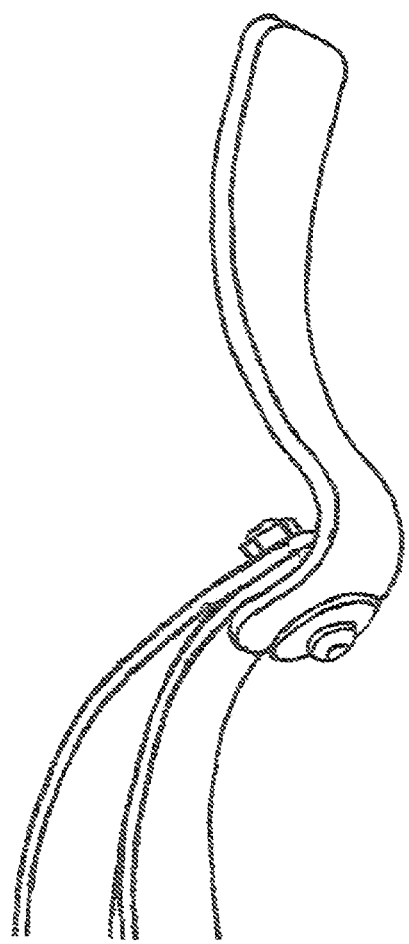
FIGS. 10a, 10b, 10c, 10d, and 10e are front, back and side perspective views of a connector element having swivel features assembled with a double C-spring device in accordance with an embodiment of the present invention.
Figure 10B:
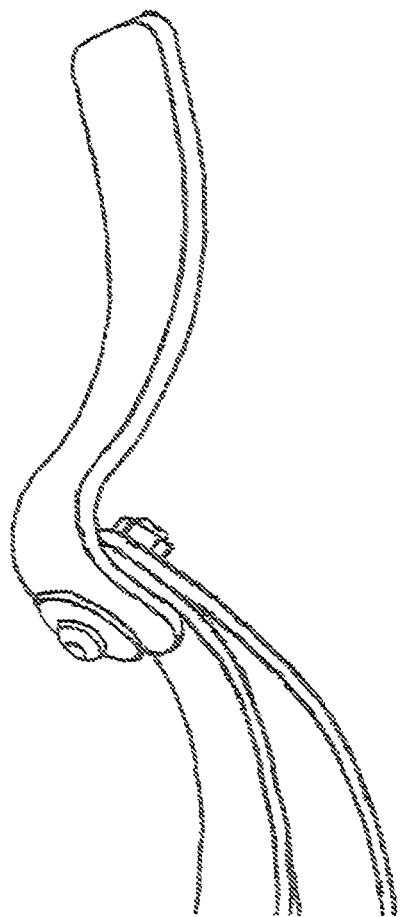
Figure 10C:
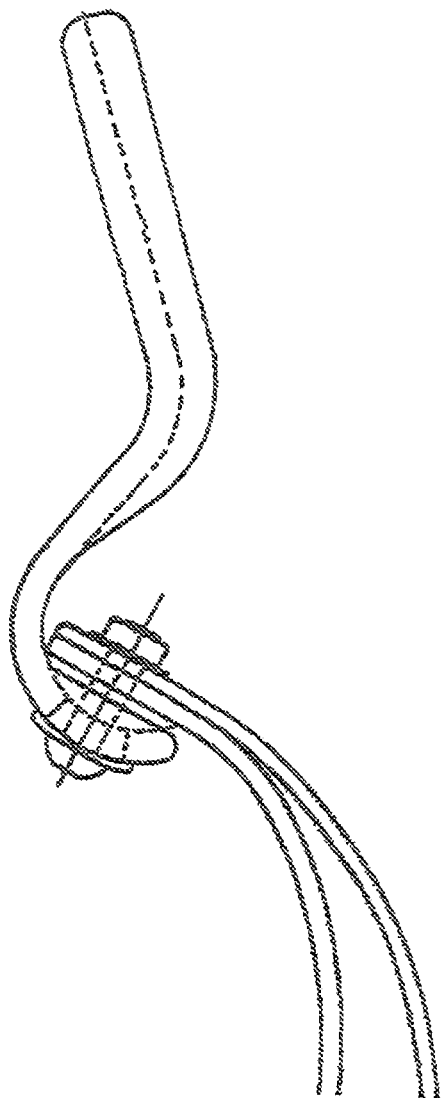
Figure 10D:
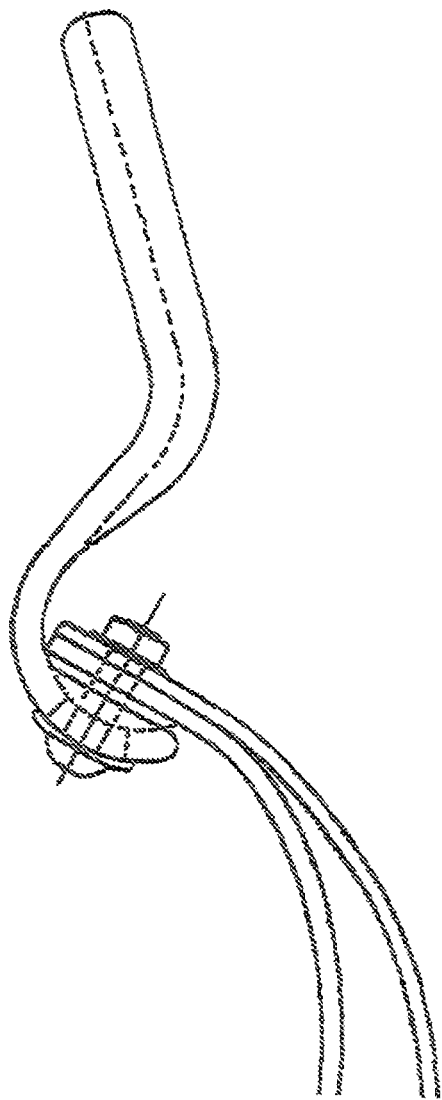
Figure 10E:
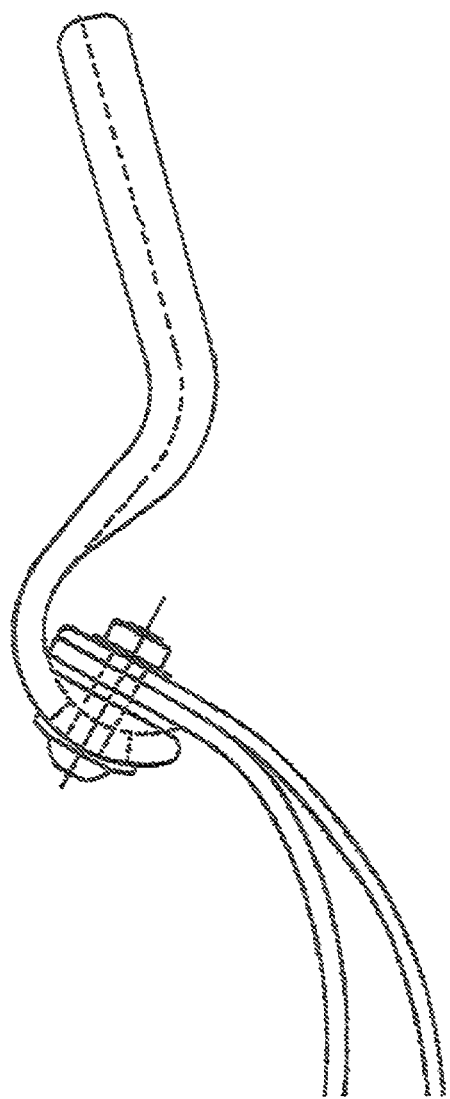
Figure 10F:
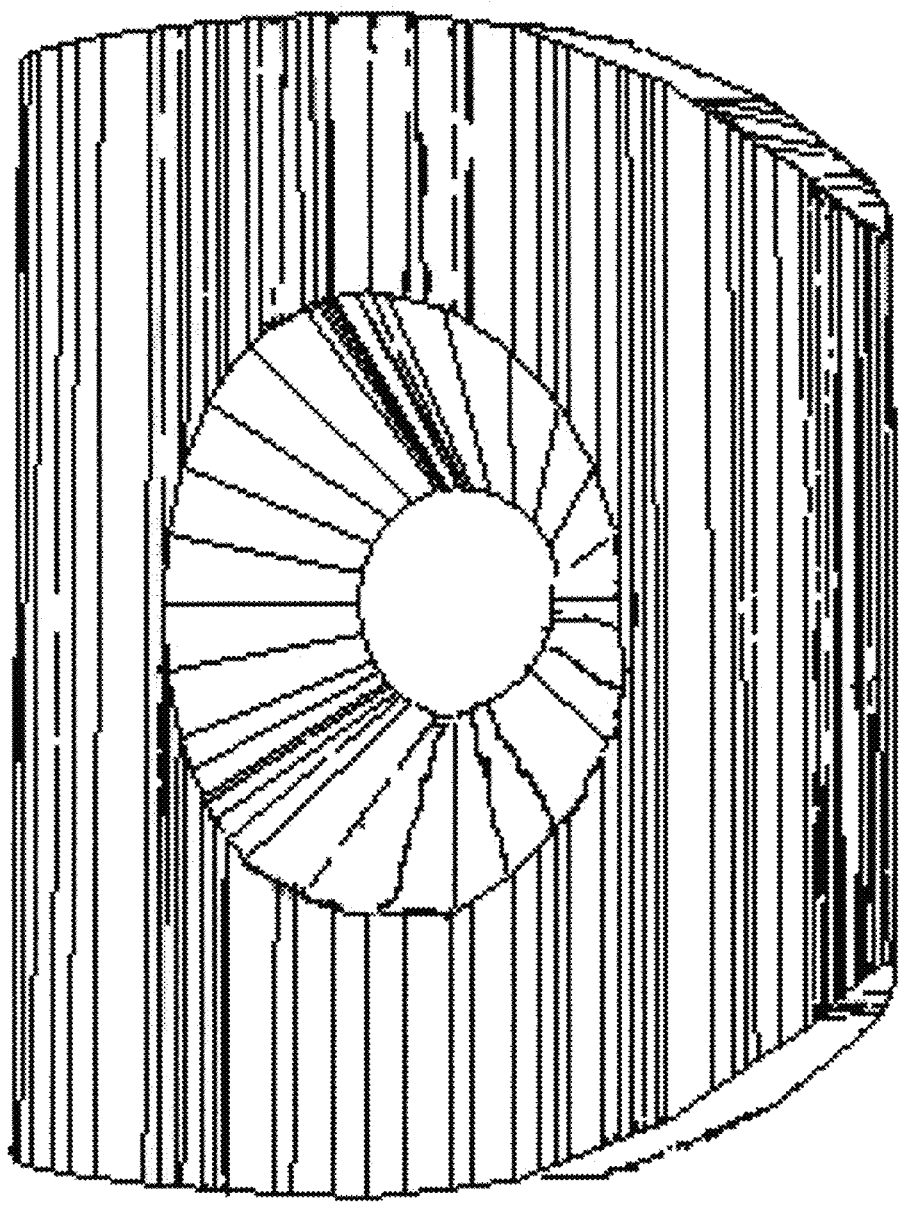
FIGS. 10f and 10g are perspective views from below and above of a shortened and unassembled connector element having swivel features in accordance with an embodiment of the present invention.
Figure 10G:
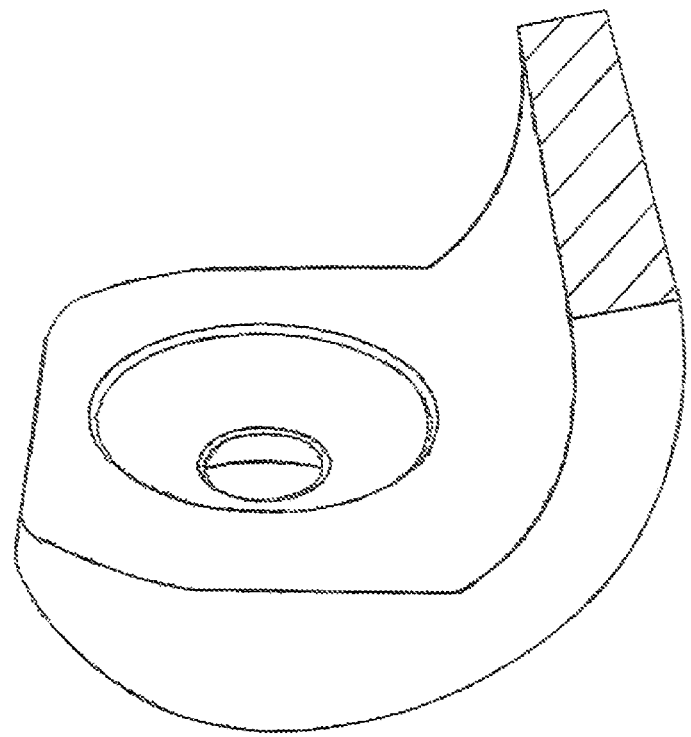
Figure 10H:
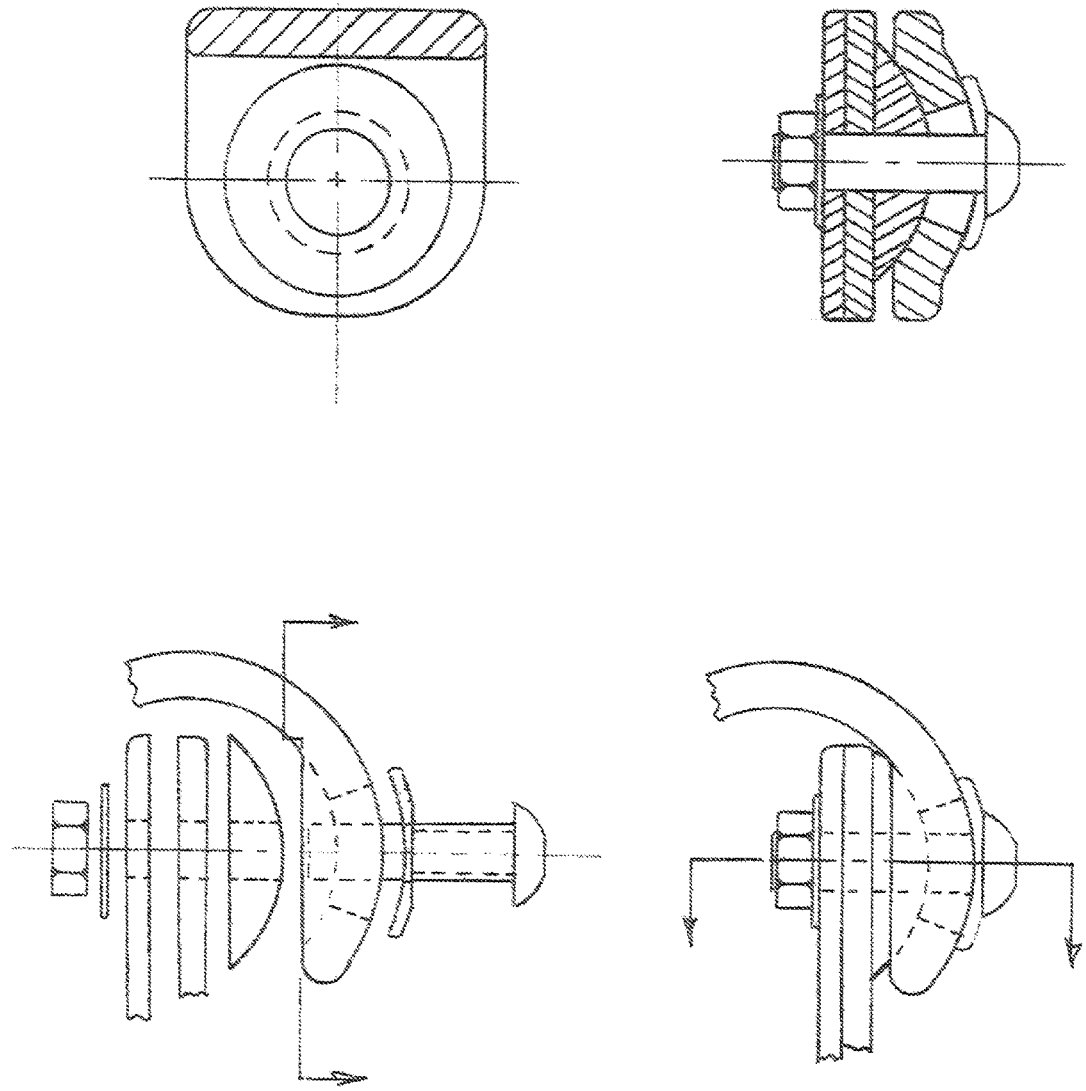
FIG. 10h shows standard views of a connector element having swivel features in accordance with an embodiment of the present invention.

Persons of ordinary skill in the art will understand that the prosthetic inventions described herein can be operably connected to a wearer's stump/socket via any suitable means. Further, while a number of different connector element variations/versions are shown throughout the drawings, these are not delimiting, and at least generally may be used with single or multiple C-Spring assemblies. FIG. 9 illustrates a preferred embodiment of the invention using an Upper Connector 35 to connect the preferred elongated energy storing and releasing elements with a prosthetic socket or other similar structure, in which the Upper Connector preferably includes one or more of the following features:

a swivel dome Lower Interface 115 between the Upper Connector 35 and the one or more generally C-Shaped Spring elements: Preferably, this interface is fully articulating and provides convenient adjustment in substantially any direction (including rotating the prosthetic toe to the wearer's left or right). The swivel dome structure preferably functions as a partial ball and socket connection. The interfitting domed interfaces 115a, 115b (one concave and one convex) can be formed and assembled in any suitable manner. Among other approaches, the domed shapes can be formed integrally with the Upper Connector and the generally C-Shaped Spring elements, or can be formed separately and affixed/attached to those components. Incorporating the interface integrally into the Upper Connector may be less expensive and easier to assemble than making and using separate parts to form the interface. The Lower Interface elements (the ball/socket parts) could be reversed from the arrangement shown in the drawings (with the socket positioned on the Spring element, instead of on the Upper Connector). Preferably, this allows easy multi-axis adjustment and positioning of the prosthesis.

alternatively, instead of a multi-axis dome adjustment, a single plane (forward/back, or Flex/Extend) curved interface: This would provide adjustment of only the forward-back alignment of the prosthesis with respect to the socket.

a Socket Interface 45 having a trough-like shape that conforms at least generally to the anterior surface of a wearer's socket. Preferably, the "trough" portion of the Socket Interface allows it to be positioned vertically at any of a wide range of vertical positions on the generally front surface of the socket, thereby providing an independent height adjustment for the prosthesis with respect to the patient. The trough is shaped to allow the wearer's main socket to be positioned up or down as needed. Preferably, the lower end of the vertical socket position is when it nears contact with the C-Spring member during compression of that Spring.

especially for Single Spring embodiments, the Lower Interface of the Upper Connector is positioned relatively forward of the wearer's "weight line" and/or near the lateral position of the prosthesis' toe (consistent with the "further forward" pivot axis discussed above). For example, through the use of such an upper connector, the spring element or elements may be connected at their upper end(s) to a patient's socket, at a connection point which is at or anterior of where a ball of the wearer's natural foot would be located, when the wearer is standing with legs together in a static position.

It is modular, and can be readily used for one spring member, two, or more

Preferably, the Upper Connector can be filament wound, and/or hand layup of resin-impregnated graphite fiber. Alternatively, it can be fabricated from aluminum or other suitable material.

preferably a single bolt 105 and nut 110 combination holds together the Lower Interface elements in a desired position. Consequently, the joint preferably can be readily adjusted by loosening and tightening a single bolt. Persons of ordinary skill in the art will appreciate that the number of bolts (or other connecting elements) at each of the various locations (footplate to Spring 1, for example) can be one, two, or more. For the preferred swivel connector joint at the upper ends of the C-shaped spring elements, a single bolt allows the desired adjustability.

Filament Winding Fabrication of Spring Members and/or Other Elements

Although the energy storing and releasing C-shaped spring element(s) of the invention can be fabricated using any suitable method, they preferably include one or more of the following features that enable them to be manufactured using filament winding or other automated processes (which can be much less labor-intensive than manual layup or other processes):

1. A substantially continuous curve. Preferably, the element has a generally C-shaped profile in elevation, with no substantial flat spots or areas.
2. At least a substantially constant thickness (no significant tapers), over at least substantially most or all of the element's length. This feature can be important for maximizing the value of using a filament winding method of fabrication, but is not so critical in hand layup, because hand layup allows easy addition of fiber/plies at desired locations, making it relatively easy to taper/change the thickness of the spring at one or more selected locations along the C-curve. Preferably, the C spring also has a substantially constant width, but the invention can be practiced without any such constant widths.
3. No tight or sharp corners within the curve. The curve can be a substantially constant radius or not, and can be symmetrical or not.
4. No undercuts or indentations along the curve. Instead, it is substantially continuously concave (or convex, depending on your perspective). Filament winding typically is not able to force the filament down into a "low spot"; instead, the fibers will be stretched tautly across that low spot, and consequently the "low spot" will NOT be part of the piece being formed. A similar concept applies to sharp corners: even though the corner may NOT technically be an undercut, filament winding likely would pull the filament at those corners more tightly than in the areas between such corners. As a consequence, the finished part would have thicker side areas as compared to those "more taut" corners.

The foregoing features (alone and/or in combination) provide several advantages to the invention, including facilitating fabrication of the preferred C-spring element(s) using an automated process such as filament winding. However, as noted elsewhere the elements can be made via any suitable process, including conventional hand layup processes.

One benefit of using filament-winding or similar automated processes is reducing the costs and time needed for fabricating the element(s). Among other things, such machine processes avoid the labor- and time-intensive process required for hand layup of such parts. Such automated processes also can provide good quality control in the resulting energy-storing/releasing members.

Any suitable filament-winding technique(s) can be used to fabricate the energy-storing/releasing members 5 of the invention. FIGS. 6*a*-6*l* illustrate one example of how filament winding might be used in practicing the present invention. Filament winding of resin-impregnated fiber parts commonly uses a hollow mandrel that is spun on its axis. Mandrels can be provided in a wide range of sizes and shapes, including ones suitable for fabricating the C-shaped spring energy storing and releasing elements of the invention. Mandrels for filament winding commonly are about two feet or more along the spinning axis. Accordingly, and as described herein, a single mandrel can be used to fabricate one or many energy storing and releasing elements during a single filament-winding process cycle.

The energy-storing/releasing C-spring members of the invention can be provided in a wide range of shapes and sizes. Depending on their precise configuration and other factors, filament winding can be used to fabricate them individually or "in bulk". As an example, it can be convenient and economical to filament-wind them on a generally cylindrical mandrel, forming a corresponding cylinder around most or all of the length of the mandrel. After the wound cylindrical piece has hardened, the individual C-spring elements can be cut from it. For example, the cylinder can be cut into separate hoops of a desired width (e.g., two-inches wide). From each such hoop, preferably at least two separate energy-storing/releasing members of the invention can be cut (if the energy-storing/releasing C-spring member is to have an arc of more than 180 degrees, only one C-spring can be cut from each ring). At some appropriate stage of the process, some or all of the part can be further custom-shaped, if desired. For example, the ends of the C-shaped spring elements can be smoothed and rounded, to avoid poking or damaging nearby persons.

As indicated, the preferred energy-storing/releasing C-spring members of the invention do not have any specially "thickened" portions or areas, but instead have a relatively constant thickness along the entire arcuate length of the member. This provides a number of benefits, in addition to enabling the part to be fabricated more efficiently. For example, the preferred relatively constant thickness helps ensure a substantially smooth "load/unload" action during use of the prosthesis or other device in which the energy-storing/releasing member is used. In other words, the energy that is required to compress or expand or otherwise deform the generally C-shaped element(s) from its resting position preferably is gradual and smooth, and has no sudden or sharp changes, through the full range of the intended compression/expansion movement of the member. Similarly, the return forces and motion (as the load is released from the member) preferably is gradual and smooth. Thus, the energy-storing/releasing element itself preferably imposes very little, if any, sudden stress/loading changes on the patient or the rest of the assembly as it is deformed and as it springs back to its resting position.

Said another way, the bending forces and characteristics preferably are relatively consistent and/or dispersed along most or even the entire length of the energy-storing/releasing element(s). The preferred thickness and shape of the energy-storing/releasing members of the invention helps distribute the energy storing and releasing action over most or substantially all of the element (rather than loading some portions of the member more heavily than other portions).

For the purpose of summarizing the invention, certain objects and advantages have been described herein. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The apparatus and methods of the invention have been described with some particularity, but the specific designs, constructions, and steps disclosed are not to be taken as delimiting of the invention. A wide range of modifications and alternative structures and steps for practicing the invention will make themselves apparent to those of ordinary skill in the art, all of which will not depart from the essence of the invention, and all such changes and modifications are intended to be encompassed within the appended claims.

The invention claimed is:

1. A prosthetic lower leg including:
at least two C-shaped spring elements, each having an upper end and a lower end, each spring element having a respective open portion where the C-shapes face forward with respect to an intended patient, said spring elements configured to cooperate with each other as the only elements, at least between said respective upper ends and said respective lower ends, for transmitting mechanical forces between a patient's socket and a ground contact point of the lower limb device, said spring elements operatively connected at their upper ends to said socket at a location that is both (a) anterior of a patient's weight line and (b) at a position at or anterior of a portion of said upper ends of the C-shape that corresponds laterally to a ball of a natural human foot.

2. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device,
said upper end of said C-shaped spring element or elements operatively connected to the socket at a location (a) at or anterior of a ball of a natural foot when a patient is standing with legs together in a static position and (b) anterior of a plumb weight line descending from the socket.

3. A prosthetic lower leg assembly including:
at least one C-shaped spring element having an upper end and a lower end,
said spring element configured to function at least between said upper end and said lower end as the only element for transmitting mechanical forces between a patient's socket and a ground contact point of the lower limb device, a connection point located at said upper end of said C-shaped spring element for operatively connecting said upper end to the socket at a location which is both (a) anterior of a patient's weight line descending from the socket and (b) at or anterior of a portion of the C-shape that corresponds to a ball of a natural human foot.

4. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket including said lower end of said C-shaped spring element operatively connected to a prosthetic footplate at a location anterior of the plumb weight line descending from the socket.

5. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket including said lower end of said C-shaped spring element operatively connected to a prosthetic footplate at a location at or anterior of the portion of the C-shape that corresponds with said ball of a normal human foot when the patient is standing with legs together in the static position.

6. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket in which said at least one C-shaped spring element has a continuous curve and a constant thickness over at least a C-shaped portion of the spring element.

7. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket including a separate connector element providing said operative connection between said upper end of said C-shaped spring element and the socket.

8. A prosthetic lower leg including:
at least one C-shaped spring element having an upper end and a lower end, both said upper end and said lower end terminating within the C-shape and defining the spring element as discrete from all other prosthetic elements forming the prosthetic lower leg, said C-shaped element including an open portion of the C-shape facing forward with respect to an intended patient, said spring element connected at said upper end to a patient's socket at a connection point which is at or anterior of a portion of the C-shape that corresponds to a ball of a natural foot, and said spring element connected at said lower end to a prosthetic foot plate, said spring element providing the only structure for transmitting mechanical forces between the patient's socket and the prosthetic footplate, said spring element further configured to provide both (a) vertical spring action in a midstance position and (b) control over the prosthetic footplate that is attached to said lower end, wherein said connection point is anterior of a distal end of the socket.

9. A prosthetic lower leg including:
at least one C-shaped spring element having an upper end and a lower end, both said upper end and said lower end terminating within the C-shape and defining the spring element as discrete from all other prosthetic elements forming the prosthetic lower leg, said C-shaped element including an open portion of the C-shape facing forward with respect to an intended patient, said spring element connected at said upper end to a patient's socket at a connection point which is at or anterior of a portion of the C-shape that corresponds to a ball of a natural foot, and said spring element connected at said lower end to a prosthetic foot plate, said spring element providing the only structure for transmitting mechanical forces between the patient's socket and the prosthetic footplate, said spring element further configured to provide both (a) vertical spring action in a midstance position and (b) control over the prosthetic footplate that is attached to said lower end, wherein said connection point is anterior of a distal end of the socket wherein said connection point is configured to hold a pant leg forward with respect to a patient's ankle area.

10. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket including an attachment element extending in an anterior direction from the patient's socket to said location at which it connects to said upper end of said at least one C-shaped spring element.

11. A prosthetic lower leg including:
at least two C-shaped spring elements, each having an upper end and a lower end, each spring element having a respective open portion where the C-shapes face forward with respect to an intended patient, said spring elements configured to cooperate with each other as the only elements, at least between said respective upper ends and said respective lower ends, for transmitting mechanical forces between a patient's socket and a ground contact point of the lower limb device, said spring elements operatively connected at their upper ends to said socket at a location that is both (a) anterior of a patient's weight line and (b) at a position at or anterior of a portion of said upper ends of the C-shape that corresponds laterally to a ball of a natural human foot including an attachment element extending in an anterior direction from the patient's socket to said location at which it connects said socket to said upper ends of said at least two C-shaped spring elements.

12. A prosthetic lower leg including:
at least two C-shaped spring elements, each having an upper end and a lower end, each spring element having a respective open portion where the C-shapes face forward with respect to an intended patient, said spring elements configured to cooperate with each other as the only elements, at least between said respective upper ends and said respective lower ends, for transmitting mechanical forces between a patient's socket and a ground contact point of the lower limb device, said spring elements operatively connected at their upper ends to said socket at a location that is both (a) anterior of a patient's weight line and (b) at a position at or anterior of a portion of said upper ends of the C-shape that corresponds laterally to a ball of a natural human foot in which said C-shaped spring element or elements are manufactured from integral portions of a tubular element having a cross-section that is generally circular, and in which said C-shaped spring element or elements are cut as a hoop from a selected length of the tubular element.

13. A prosthetic lower leg including:
at least two C-shaped spring elements, each having an upper end and a lower end, each spring element having a respective open portion where the C-shapes face forward with respect to an intended patient, said spring elements configured to cooperate with each other as the only elements, at least between said respective upper ends and said respective lower ends, for transmitting mechanical forces between a patient's socket and a ground contact point of the lower limb device, said spring elements operatively connected at their upper ends to said socket at a location that is both (a) anterior of a patient's weight line and (b) at a position at or anterior of a portion of said upper ends of the C-shape that corresponds laterally to a ball of a natural human foot in which said C-shaped spring element or elements are manufactured from integral portions of a tubular element having a cross-section that is generally circular, and in which said C-shaped spring element or elements are cut as a hoop from a selected length of the tubular element in which said C-shaped spring element or elements are further cut from said hoop by cutting said hoop into two similarly-shaped C-shaped spring elements.

14. A prosthetic lower leg including:
at least two C-shaped spring elements, each having an upper end and a lower end, each spring element having a respective open portion where the C-shapes face forward with respect to an intended patient, said spring elements configured to cooperate with each other as the only elements, at least between said respective upper ends and said respective lower ends, for transmitting mechanical forces between a patient's socket and a ground contact point of the lower limb device, said spring elements operatively connected at their upper ends to said socket at a location that is both (a) anterior of a patient's weight line and (b) at a position at or anterior of a portion of said upper ends of the C-shape that corresponds laterally to a ball of a natural human foot wherein said lower end of one of said at least two spring elements is connected to a prosthetic footplate at a middle portion of said footplate and said lower end of said at least two spring elements is connected to said footplate at a location anterior of said middle portion of the footplate.

15. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket in which said lower end of said spring element or elements is connected to a prosthetic footplate at a portion of the C-shape which approximately corresponds with said ball of the normal human foot.

16. A prosthetic lower leg including:
at least two C-shaped spring elements, each having an upper end and a lower end, each spring element having a respective open portion where the C-shapes face forward with respect to an intended patient, said spring elements configured to cooperate with each other as the only elements, at least between said respective upper ends and said respective lower ends, for transmitting mechanical forces between a patient's socket and a ground contact point of the lower limb device, said spring elements operatively connected at their upper ends to said socket at a location that is both (a) anterior of a patient's weight line and (b) at a position at or anterior of a portion of said upper ends of the C-shape that corresponds laterally to a ball of a natural human foot in which said C-shaped spring element or elements are manufactured from integral portions a cross-section that is generally circular, and in which said C-shaped spring element or elements are cut as a hoop from a selected length of the tubular element, in which said C-shaped spring element or elements are further cut from said hoop by cutting said hoop into two similarly-shaped C-shaped spring elements in which said C-shaped spring element or elements formed from said hoop are further processed using filament winding.

17. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket in which said ground contact point of the lower limb device includes a toe-bearing plate.

18. A prosthetic lower leg assembly including:
at least one C-shaped spring element having an upper end and a lower end,
said spring element or elements configured to function at least between said upper end and said lower end as the only element or elements for transmitting mechanical forces between a patient's socket and a ground contact point of the lower limb device, said upper end of said C-shaped spring element or elements operatively connected to the socket at a location (a) at or anterior of a ball of a natural foot when a patient is standing with legs together in a static position and (b) anterior of a plumb weight line descending from the socket in which said ground contact point of the lower limb device includes a heel-to-toe bearing plate.

* * * * *